US009439862B2

(12) United States Patent
Weers et al.

(10) Patent No.: US 9,439,862 B2
(45) Date of Patent: Sep. 13, 2016

(54) PHOSPHOLIPID-BASED POWDERS FOR DRUG DELIVERY

(71) Applicants: Jeffry G Weers, Belmont, CA (US); Thomas E Tarara, Burlingame, CA (US); Luis A Dellamary, San Marcos, CA (US); Ernest G Schutt, San Diego, CA (US)

(72) Inventors: Jeffry G Weers, Belmont, CA (US); Thomas E Tarara, Burlingame, CA (US); Luis A Dellamary, San Marcos, CA (US); Jean G Riess, Falicon (FR); Ernest G Schutt, San Diego, CA (US)

(73) Assignee: Novartis AG, Basel (CH)

(*) Notice: Subject to any disclaimer, the term of this patent is extended or adjusted under 35 U.S.C. 154(b) by 19 days.

(21) Appl. No.: 14/243,639

(22) Filed: Apr. 2, 2014

(65) Prior Publication Data
US 2014/0212504 A1 Jul. 31, 2014

Related U.S. Application Data

(60) Continuation of application No. 12/258,163, filed on Oct. 24, 2008, now Pat. No. 8,709,484, which is a division of application No. 09/851,226, filed on May 8, 2001, now Pat. No. 7,442,388, which is a continuation-in-part of application No. 09/568,818, filed on May 10, 2000, now Pat. No. 7,871,598, said application No. 12/258,163 is a continuation of application No. 10/141,219, filed on May 7, 2002, now abandoned.

(60) Provisional application No. 60/208,896, filed on Jun. 2, 2000, provisional application No. 60/216,621, filed on Jul. 7, 2000.

(51) Int. Cl.
| A61K 9/14 | (2006.01) |
| A61K 9/16 | (2006.01) |
| A61K 9/00 | (2006.01) |
| A61K 47/24 | (2006.01) |
| A61K 31/465 | (2006.01) |
| A61K 31/496 | (2006.01) |
| A61K 31/58 | (2006.01) |
| A61K 31/7036 | (2006.01) |
| A61K 31/7048 | (2006.01) |
| A61K 38/29 | (2006.01) |
| A61K 45/06 | (2006.01) |
| A61K 47/02 | (2006.01) |
| A61K 9/10 | (2006.01) |
| A61M 15/00 | (2006.01) |

(52) U.S. Cl.
CPC .......... *A61K 9/1617* (2013.01); *A61K 9/008* (2013.01); *A61K 9/0075* (2013.01); *A61K 9/0082* (2013.01); *A61K 9/14* (2013.01); *A61K 9/1611* (2013.01); *A61K 31/465* (2013.01); *A61K 31/496* (2013.01); *A61K 31/58* (2013.01); *A61K 31/7036* (2013.01); *A61K 31/7048* (2013.01); *A61K 38/29* (2013.01); *A61K 45/06* (2013.01); *A61K 47/24* (2013.01); *A61K 9/10* (2013.01); *A61K 9/1694* (2013.01); *A61K 47/02* (2013.01); *A61M 15/0065* (2013.01); *A61M 2205/3306* (2013.01)

(58) Field of Classification Search
CPC ....................................................... A61K 9/14
See application file for complete search history.

(56) References Cited

U.S. PATENT DOCUMENTS

| 979,993 A | 10/1910 | O'Byrne et al. |
| 1,855,591 A | 4/1932 | Wallerstein |
| 2,457,036 A | 12/1948 | Epstein |
| 2,797,201 A | 6/1957 | Veatch et al. |
| 3,014,844 A | 12/1961 | Thiel et al. |
| 3,362,405 A | 1/1968 | Hazel |
| 3,555,717 A | 1/1971 | Chivers |
| 3,619,294 A | 11/1971 | Black et al. |
| 3,632,357 A | 1/1972 | Childs |
| 3,655,442 A | 4/1972 | Schwar et al. |
| 3,745,682 A | 7/1973 | Waldeisen |
| 3,812,854 A | 5/1974 | Michaels et al. |
| 3,948,263 A | 4/1976 | Drake, Jr. et al. |
| 3,957,964 A | 5/1976 | Grimm, III |
| 3,964,483 A | 6/1976 | Mathes |
| 3,975,512 A | 8/1976 | Long, Jr. |
| 4,009,280 A | 2/1977 | Macarthur et al. |
| 4,036,223 A | 7/1977 | Obert |
| 4,089,120 A | 5/1978 | Kozishek |
| 4,098,273 A | 7/1978 | Glenn |

(Continued)

FOREIGN PATENT DOCUMENTS

| AU | 731671 | 9/1996 |
| AU | 714998 | 1/1997 |

(Continued)

OTHER PUBLICATIONS

Dellamary et al., "Hollow Porous Particles in Metered Dose Inhalers," (2000) Pharm. Res., vol. 17(2), p. 168-174.

(Continued)

*Primary Examiner* — Samira Jean-Louis
(74) *Attorney, Agent, or Firm* — Guy V. Tucker

(57) ABSTRACT

Phospholipid based powders for drug delivery applications are disclosed. The powders comprise a polyvalent cation in an amount effective to increase the gel-to-liquid crystal transition temperature of the particle compared to particles without the polyvalent cation. The powders are hollow and porous and are preferably administered via inhalation.

19 Claims, 3 Drawing Sheets

(56) References Cited

U.S. PATENT DOCUMENTS

| | | |
|---|---|---|
| 4,102,999 A | 7/1978 | Umezawa et al. |
| 4,127,502 A | 11/1978 | Li Mutti et al. |
| 4,127,622 A | 11/1978 | Watanabe et al. |
| 4,158,544 A | 6/1979 | Louderback |
| 4,159,319 A | 6/1979 | Bachmann et al. |
| 4,161,516 A | 7/1979 | Bell |
| 4,180,593 A | 12/1979 | Cohan |
| 4,201,774 A | 5/1980 | Igarashi et al. |
| 4,211,769 A | 7/1980 | Okada et al. |
| 4,244,949 A | 1/1981 | Gupta |
| 4,253,468 A | 3/1981 | Lehmbeck |
| 4,281,031 A | 7/1981 | Hillman |
| 4,326,524 A | 4/1982 | Drake, Jr. et al. |
| 4,327,076 A | 4/1982 | Puglia et al. |
| 4,327,077 A | 4/1982 | Puglia et al. |
| 4,358,442 A | 11/1982 | Wirtz-Peitz |
| 4,371,557 A | 2/1983 | Oppy et al. |
| 4,397,799 A | 8/1983 | Edgren et al. |
| 4,404,228 A | 9/1983 | Cloosterman et al. |
| 4,407,786 A | 10/1983 | Drake et al. |
| 4,452,239 A | 6/1984 | Malem |
| 4,484,577 A | 11/1984 | Sackner et al. |
| 4,524,769 A | 6/1985 | Wetterlin |
| 4,534,343 A | 8/1985 | Nowacki et al. |
| 4,571,334 A | 2/1986 | Yoshida et al. |
| 4,588,744 A | 5/1986 | McHugh |
| 4,590,206 A | 5/1986 | Forrester et al. |
| 4,591,552 A | 5/1986 | Neurath |
| 4,613,500 A | 9/1986 | Suzuki et al. |
| 4,617,272 A | 10/1986 | Kirkwood et al. |
| 4,620,847 A | 11/1986 | Shishov et al. |
| 4,659,696 A | 4/1987 | Hirai et al. |
| 4,680,027 A | 7/1987 | Parsons et al. |
| 4,684,719 A | 8/1987 | Nishikawa et al. |
| 4,701,417 A | 10/1987 | Portenhauser et al. |
| 4,713,249 A | 12/1987 | Schröder |
| 4,721,709 A | 1/1988 | Seth et al. |
| 4,739,754 A | 4/1988 | Shaner |
| 4,758,583 A | 7/1988 | Cerami et al. |
| 4,761,400 A | 8/1988 | Doat et al. |
| 4,762,857 A | 8/1988 | Bollin, Jr. et al. |
| 4,765,987 A | 8/1988 | Bonte et al. |
| 4,790,824 A | 12/1988 | Morrow et al. |
| 4,793,997 A | 12/1988 | Drake et al. |
| 4,812,444 A | 3/1989 | Mitsuhashi et al. |
| 4,814,436 A | 3/1989 | Shibata et al. |
| 4,818,542 A | 4/1989 | DeLuca et al. |
| 4,819,629 A | 4/1989 | Jonson |
| 4,824,938 A | 4/1989 | Koyama et al. |
| 4,830,858 A | 5/1989 | Payne et al. |
| 4,847,079 A | 7/1989 | Kwan |
| 4,851,211 A | 7/1989 | Adjei et al. |
| 4,855,326 A | 8/1989 | Fuisz |
| 4,861,627 A | 8/1989 | Mathiowitz et al. |
| 4,865,871 A | 9/1989 | Livesey et al. |
| 4,866,051 A | 9/1989 | Hunt |
| 4,883,762 A | 11/1989 | Hoskins |
| 4,891,319 A | 1/1990 | Roser |
| 4,904,479 A | 2/1990 | Illum |
| 4,906,463 A | 3/1990 | Cleary et al. |
| 4,907,583 A | 3/1990 | Wetterlin et al. |
| 4,942,544 A | 7/1990 | McIntosh et al. |
| 4,950,477 A | 8/1990 | Schmitt et al. |
| 4,952,402 A | 8/1990 | Sparks et al. |
| 4,955,371 A | 9/1990 | Zamba |
| 4,971,787 A | 11/1990 | Cherukuri et al. |
| 4,984,158 A | 1/1991 | Hillsman |
| 4,988,683 A | 1/1991 | Corbiere |
| 4,995,385 A | 2/1991 | Valentini et al. |
| 4,999,384 A | 3/1991 | Roberts et al. |
| 5,006,343 A | 4/1991 | Benson et al. |
| 5,011,678 A | 4/1991 | Wang et al. |
| 5,013,557 A | 5/1991 | Tai |
| 5,017,372 A | 5/1991 | Hastings |
| 5,026,566 A | 6/1991 | Roser |
| 5,026,772 A | 6/1991 | Kobayashi et al. |
| 5,032,585 A | 7/1991 | Lichtenberger |
| 5,033,463 A | 7/1991 | Cocozza |
| 5,043,158 A | 8/1991 | Sleytr |
| 5,043,165 A | 8/1991 | Radhakrishnan |
| 5,049,388 A | 9/1991 | Knight et al. |
| 5,049,389 A | 9/1991 | Radhakrishnan |
| 5,069,936 A | 12/1991 | Yen |
| 5,089,181 A | 2/1992 | Hauser |
| 5,098,893 A | 3/1992 | Franks et al. |
| 5,100,591 A | 3/1992 | Leclef |
| 5,112,596 A | 5/1992 | Malfroy-Camine |
| 5,112,598 A | 5/1992 | Biesalski |
| 5,118,494 A | 6/1992 | Schultz et al. |
| 5,126,123 A | 6/1992 | Johnson |
| 5,145,684 A | 9/1992 | Liversidge et al. |
| 5,149,543 A | 9/1992 | Cohen et al. |
| 5,149,653 A | 9/1992 | Roser |
| 5,160,745 A | 11/1992 | De Luca et al. |
| 5,173,298 A | 12/1992 | Meadows |
| 5,182,097 A | 1/1993 | Byron et al. |
| 5,190,029 A | 3/1993 | Byron et al. |
| 5,200,399 A | 4/1993 | Wettlaufer et al. |
| 5,202,159 A | 4/1993 | Chen et al. |
| 5,202,333 A | 4/1993 | Berger et al. |
| 5,204,108 A | 4/1993 | Illum |
| 5,208,226 A | 5/1993 | Palmer |
| 5,215,079 A | 6/1993 | Fine et al. |
| 5,225,183 A | 7/1993 | Purewal |
| 5,230,884 A | 7/1993 | Evans et al. |
| 5,239,993 A | 8/1993 | Evans |
| 5,240,712 A | 8/1993 | Smith et al. |
| 5,240,843 A | 8/1993 | Gibson et al. |
| 5,240,846 A | 8/1993 | Collins et al. |
| 5,254,330 A | 10/1993 | Ganderton et al. |
| 5,260,306 A | 11/1993 | Boardman et al. |
| 5,262,405 A | 11/1993 | Girod-Vaquez et al. |
| 5,270,048 A | 12/1993 | Drake |
| 5,284,656 A | 2/1994 | Platz et al. |
| 5,290,765 A | 3/1994 | Wettlaufer et al. |
| 5,299,566 A | 4/1994 | Davis et al. |
| 5,304,125 A | 4/1994 | Leith |
| 5,306,483 A | 4/1994 | Mautone |
| 5,306,506 A | 4/1994 | Zema et al. |
| 5,308,620 A | 5/1994 | Yen |
| 5,309,900 A | 5/1994 | Knoch et al. |
| 5,312,335 A | 5/1994 | McKinnon et al. |
| 5,312,909 A | 5/1994 | Driessen et al. |
| 5,342,625 A | 8/1994 | Hauer et al. |
| 5,348,730 A | 9/1994 | Greenleaf et al. |
| 5,348,852 A | 9/1994 | Bonderman |
| 5,354,562 A | 10/1994 | Platz et al. |
| 5,354,934 A | 10/1994 | Pitt et al. |
| 5,366,734 A | 11/1994 | Hutchinson |
| 5,376,359 A | 12/1994 | Johnson |
| 5,380,473 A | 1/1995 | Bogue et al. |
| 5,380,519 A | 1/1995 | Schneider et al. |
| 5,384,345 A | 1/1995 | Naton |
| 5,387,431 A | 2/1995 | Fuisz |
| 5,403,861 A | 4/1995 | Goldwin et al. |
| 5,404,871 A | 4/1995 | Goodman et al. |
| 5,422,360 A | 6/1995 | Miyajima et al. |
| 5,422,384 A | 6/1995 | Samuels et al. |
| 5,425,951 A | 6/1995 | Goodrich, Jr. et al. |
| 5,437,272 A | 8/1995 | Fuhrman |
| 5,437,274 A | 8/1995 | Khoobehi |
| 5,451,569 A | 9/1995 | Wong et al. |
| 5,453,514 A | 9/1995 | Niigata et al. |
| 5,458,135 A | 10/1995 | Patton et al. |
| 5,470,885 A | 11/1995 | Fuhrman et al. |
| 5,474,059 A | 12/1995 | Cooper |
| 5,474,759 A | 12/1995 | Fassberg et al. |
| 5,482,927 A | 1/1996 | Maniar et al. |
| 5,490,498 A | 2/1996 | Faithfull et al. |
| 5,492,688 A | 2/1996 | Byron et al. |
| 5,506,203 A | 4/1996 | Backstrom et al. |
| 5,507,277 A | 4/1996 | Rubsamen |
| 5,508,269 A | 4/1996 | Smith |
| 5,512,547 A | 4/1996 | Johnson et al. |

(56) References Cited

U.S. PATENT DOCUMENTS

| | | |
|---|---|---|
| 5,518,709 A | 5/1996 | Sutton et al. |
| 5,518,731 A | 5/1996 | Meadows |
| 5,518,998 A | 5/1996 | Backstrom et al. |
| 5,527,521 A | 6/1996 | Unger |
| 5,540,225 A | 7/1996 | Schutt |
| 5,542,935 A | 8/1996 | Unger et al. |
| 5,547,656 A | 8/1996 | Unger |
| 5,547,696 A | 8/1996 | Sorensen |
| 5,552,160 A | 9/1996 | Liversidge et al. |
| 5,562,608 A | 10/1996 | Sekins et al. |
| 5,567,439 A | 10/1996 | Mters et al. |
| 5,569,448 A | 10/1996 | Wong et al. |
| 5,569,450 A | 10/1996 | Duan et al. |
| 5,571,499 A | 11/1996 | Hafler et al. |
| 5,577,497 A | 11/1996 | Mecikalski et al. |
| 5,580,575 A | 12/1996 | Unger et al. |
| 5,580,859 A | 12/1996 | Felgner et al. |
| 5,589,167 A | 12/1996 | Cleland et al. |
| 5,591,453 A | 1/1997 | Ducheyne et al. |
| 5,605,673 A | 2/1997 | Schutt et al. |
| 5,605,674 A | 2/1997 | Purewal et al. |
| 5,607,915 A | 3/1997 | Patton et al. |
| 5,611,344 A | 3/1997 | Bernstein et al. |
| 5,612,053 A | 3/1997 | Baichwal et al. |
| 5,616,311 A | 4/1997 | Yen |
| 5,618,786 A | 4/1997 | Roosdorp et al. |
| 5,621,094 A | 4/1997 | Roser et al. |
| 5,631,225 A | 5/1997 | Sorensen |
| 5,635,159 A | 6/1997 | Fu Lu et al. |
| 5,635,161 A | 6/1997 | Adjei et al. |
| 5,642,728 A | 7/1997 | Andersson et al. |
| 5,648,095 A | 7/1997 | Illum et al. |
| 5,653,961 A | 8/1997 | McNally et al. |
| 5,653,962 A | 8/1997 | Akehurst et al. |
| 5,654,007 A | 8/1997 | Johnson et al. |
| 5,654,278 A | 8/1997 | Sorensen |
| 5,655,521 A | 8/1997 | Faithfull et al. |
| 5,656,297 A | 8/1997 | Bernstein et al. |
| 5,658,549 A | 8/1997 | Akehurst et al. |
| 5,659,297 A | 8/1997 | Tatavoosian |
| 5,667,808 A | 9/1997 | Johnson et al. |
| 5,667,809 A | 9/1997 | Trevino et al. |
| 5,673,686 A | 10/1997 | Villax et al. |
| 5,674,471 A | 10/1997 | Akehurst et al. |
| 5,674,472 A | 10/1997 | Akehurst et al. |
| 5,674,473 A | 10/1997 | Purewal et al. |
| 5,676,929 A | 10/1997 | Akehurst et al. |
| 5,676,931 A | 10/1997 | Adjei et al. |
| 5,681,545 A | 10/1997 | Purewal et al. |
| 5,681,746 A | 10/1997 | Bodner et al. |
| 5,683,676 A | 11/1997 | Akehurst et al. |
| 5,683,677 A | 11/1997 | Purewal et al. |
| 5,688,782 A | 11/1997 | Neale et al. |
| 5,690,954 A | 11/1997 | Illum |
| 5,694,919 A | 12/1997 | Rubsamen |
| 5,695,743 A | 12/1997 | Purewal et al. |
| 5,695,744 A | 12/1997 | Neale et al. |
| 5,698,537 A | 12/1997 | Pruss |
| 5,705,482 A | 1/1998 | Christensen et al. |
| 5,707,352 A | 1/1998 | Sekins et al. |
| 5,707,644 A | 1/1998 | Illum |
| 5,714,141 A | 2/1998 | Ho |
| 5,718,222 A | 2/1998 | Lloyd et al. |
| 5,718,921 A | 2/1998 | Mathiowitz et al. |
| 5,720,940 A | 2/1998 | Purewal et al. |
| 5,724,957 A | 3/1998 | Rubsamen et al. |
| 5,725,841 A | 3/1998 | Duan et al. |
| 5,725,871 A | 3/1998 | Illum |
| 5,727,546 A | 3/1998 | Clarke et al. |
| 5,728,574 A | 3/1998 | Legg |
| 5,733,555 A | 3/1998 | Chu |
| 5,735,263 A | 4/1998 | Rubsamen et al. |
| 5,736,124 A | 4/1998 | Akehurst et al. |
| 5,740,064 A | 4/1998 | Witte |
| 5,740,794 A | 4/1998 | Smith et al. |
| 5,741,478 A | 4/1998 | Osborne et al. |
| 5,741,522 A | 4/1998 | Violante et al. |
| 5,742,352 A | 4/1998 | Tsukagoshi |
| 5,743,250 A | 4/1998 | Gonda et al. |
| 5,743,252 A | 4/1998 | Rubsamen et al. |
| 5,744,123 A | 4/1998 | Akehurst et al. |
| 5,744,166 A | 4/1998 | Illum |
| 5,747,001 A | 5/1998 | Wiedmann et al. |
| 5,747,445 A | 5/1998 | Backstrom et al. |
| 5,755,218 A | 5/1998 | Johansson et al. |
| 5,756,104 A | 5/1998 | de Haan et al. |
| 5,759,572 A | 6/1998 | Sugimoto |
| 5,766,520 A | 6/1998 | Bronshtein |
| 5,766,573 A | 6/1998 | Purewal et al. |
| 5,770,187 A | 6/1998 | Hasebe et al. |
| 5,770,222 A | 6/1998 | Unger et al. |
| 5,770,234 A | 6/1998 | Gristina |
| 5,770,559 A | 6/1998 | Manning et al. |
| 5,770,585 A | 6/1998 | Kaufman et al. |
| 5,775,320 A | 7/1998 | Patton et al. |
| 5,776,496 A | 7/1998 | Violante et al. |
| 5,780,014 A | 7/1998 | Eljamal et al. |
| 5,780,295 A | 7/1998 | Livesey et al. |
| 5,785,049 A | 7/1998 | Smith et al. |
| 5,804,212 A | 9/1998 | Illum |
| 5,807,552 A | 9/1998 | Stanton |
| 5,811,406 A | 9/1998 | Szoka, Jr. et al. |
| 5,814,607 A | 9/1998 | Patton |
| 5,817,293 A | 10/1998 | Akehurst et al. |
| 5,820,883 A | 10/1998 | Tice et al. |
| 5,824,133 A | 10/1998 | Tranquilla |
| 5,829,435 A | 11/1998 | Rubsamen et al. |
| 5,830,430 A | 11/1998 | Unger et al. |
| 5,830,853 A | 11/1998 | Backstrom et al. |
| 5,849,700 A | 12/1998 | Sorensen et al. |
| 5,851,453 A | 12/1998 | Hanna et al. |
| 5,853,698 A | 12/1998 | Straub et al. |
| 5,853,740 A | 12/1998 | Lu et al. |
| 5,853,752 A | 12/1998 | Unger et al. |
| 5,853,763 A | 12/1998 | Tice et al. |
| 5,855,913 A | 1/1999 | Hanes et al. |
| 5,856,367 A | 1/1999 | Barrows et al. |
| 5,858,784 A | 1/1999 | Debs et al. |
| 5,861,175 A | 1/1999 | Walters |
| 5,863,554 A | 1/1999 | Illum |
| 5,873,360 A | 2/1999 | Davies et al. |
| 5,874,063 A | 2/1999 | Briggner et al. |
| 5,874,064 A | 2/1999 | Edwards et al. |
| 5,875,776 A | 3/1999 | Vaghefi |
| 5,891,844 A | 4/1999 | Hafner |
| 5,891,873 A | 4/1999 | Colaco et al. |
| 5,898,028 A | 4/1999 | Jensen et al. |
| 5,910,301 A | 6/1999 | Farr |
| 5,921,447 A | 7/1999 | Barger et al. |
| 5,925,334 A | 7/1999 | Rubin et al. |
| 5,925,337 A | 7/1999 | Arraudeau |
| 5,928,469 A | 7/1999 | Franks et al. |
| 5,928,647 A | 7/1999 | Rock |
| 5,934,273 A | 8/1999 | Andersson |
| 5,948,411 A | 9/1999 | Koyama et al. |
| 5,955,143 A | 9/1999 | Wheatley |
| 5,955,448 A | 9/1999 | Colaco et al. |
| 5,962,424 A | 10/1999 | Hallahan |
| 5,972,366 A | 10/1999 | Haynes et al. |
| 5,972,388 A | 10/1999 | Sakon |
| 5,976,436 A | 11/1999 | Livesley et al. |
| 5,976,574 A | 11/1999 | Gordon |
| 5,977,081 A | 11/1999 | Marciani |
| 5,985,248 A | 11/1999 | Gordon et al. |
| 5,985,309 A | 11/1999 | Edwards et al. |
| 5,993,783 A | 11/1999 | Eljamal et al. |
| 5,993,805 A | 11/1999 | Sutton et al. |
| 5,994,314 A | 11/1999 | Eljamal et al. |
| 5,994,318 A | 11/1999 | Gould-Fogerite et al. |
| 5,997,848 A | 12/1999 | Patton |
| 6,001,336 A | 12/1999 | Gordon |
| 6,013,638 A | 1/2000 | Crystal et al. |
| 6,017,310 A | 1/2000 | Johnson et al. |
| 6,019,968 A | 2/2000 | Platz et al. |

(56) References Cited

U.S. PATENT DOCUMENTS

| | | |
|---|---|---|
| 6,032,666 A | 3/2000 | Davies et al. |
| 6,034,080 A | 3/2000 | Colaco et al. |
| 6,041,777 A | 3/2000 | Faithfull |
| 6,048,546 A | 4/2000 | Sasaki |
| 6,051,256 A | 4/2000 | Platz et al. |
| 6,051,259 A | 4/2000 | Johnson et al. |
| 6,051,566 A | 4/2000 | Bianco |
| 6,060,069 A | 5/2000 | Hill et al. |
| 6,068,600 A | 5/2000 | Johnson et al. |
| 6,071,428 A | 6/2000 | Franks et al. |
| 6,071,497 A | 6/2000 | Steiner |
| 6,077,543 A | 6/2000 | Gordon et al. |
| 6,089,228 A | 7/2000 | Smith |
| 6,113,948 A | 9/2000 | Heath et al. |
| 6,116,237 A | 9/2000 | Schultz et al. |
| 6,117,455 A | 9/2000 | Takada |
| 6,120,751 A | 9/2000 | Ungar |
| 6,123,924 A | 9/2000 | Mistry et al. |
| 6,123,936 A | 9/2000 | Platz et al. |
| 6,129,934 A | 10/2000 | Egan et al. |
| 6,136,295 A | 10/2000 | Edwards et al. |
| 6,136,346 A | 10/2000 | Eljamal et al. |
| 6,138,668 A | 10/2000 | Patton et al. |
| 6,139,819 A | 10/2000 | Unger et al. |
| 6,142,216 A | 11/2000 | Lannes |
| 6,143,276 A | 11/2000 | Unger |
| 6,165,463 A | 12/2000 | Platz et al. |
| 6,165,508 A | 12/2000 | Tracy et al. |
| 6,165,597 A | 12/2000 | Williams |
| RE37,053 E | 2/2001 | Hanes et al. |
| 6,187,344 B1 | 2/2001 | Eljamal et al. |
| 6,190,859 B1 | 2/2001 | Putnak et al. |
| 6,207,135 B1 | 3/2001 | Rossling et al. |
| 6,230,707 B1 | 5/2001 | Horlin |
| 6,231,851 B1 | 5/2001 | Platz et al. |
| 6,248,720 B1 | 6/2001 | Mathiowitz et al. |
| 6,254,854 B1 | 7/2001 | Edwards et al. |
| 6,257,233 B1 | 7/2001 | Burr |
| 6,258,341 B1 | 7/2001 | Foster et al. |
| 6,284,282 B1 | 9/2001 | Maa et al. |
| 6,290,991 B1 | 9/2001 | Roser et al. |
| 6,303,581 B2 | 10/2001 | Pearlman |
| 6,303,582 B1 | 10/2001 | Eljamal et al. |
| 6,309,623 B1 | 10/2001 | Weers et al. |
| 6,309,671 B1 | 10/2001 | Foster et al. |
| 6,313,102 B1 | 11/2001 | Colaco et al. |
| 6,315,983 B1 | 11/2001 | Eistetter |
| 6,331,310 B1 | 12/2001 | Roser et al. |
| 6,334,182 B2 | 12/2001 | Merchant et al. |
| 6,358,530 B1 | 3/2002 | Eljamal et al. |
| 6,365,190 B1 | 4/2002 | Gordon et al. |
| 6,372,258 B1 | 4/2002 | Platz et al. |
| 6,387,886 B1 | 5/2002 | Montgomery |
| 6,416,739 B1 | 7/2002 | Rogerson et al. |
| 6,423,334 B1 | 7/2002 | Brayden et al. |
| 6,423,344 B1 | 7/2002 | Platz et al. |
| 6,426,210 B1 | 7/2002 | Franks et al. |
| 6,433,040 B1 | 8/2002 | Dellamary et al. |
| 6,468,782 B1 | 10/2002 | Tunnacliffe et al. |
| 6,475,468 B2 | 11/2002 | Zhu et al. |
| 6,479,049 B1 | 11/2002 | Platz et al. |
| 6,503,411 B1 | 1/2003 | Franks et al. |
| 6,503,480 B1 | 1/2003 | Edwards et al. |
| 6,509,006 B1 | 1/2003 | Platz et al. |
| 6,514,482 B1 | 2/2003 | Bartus |
| 6,514,496 B1 | 2/2003 | Platz et al. |
| 6,518,239 B1 | 2/2003 | Kuo et al. |
| 6,551,578 B2 | 4/2003 | Adjei et al. |
| 6,565,871 B2 | 5/2003 | Roser et al. |
| 6,565,885 B1 | 5/2003 | Tarara et al. |
| 6,569,406 B2 | 5/2003 | Stevenson et al. |
| 6,569,458 B1 | 5/2003 | Gombotz et al. |
| 6,572,893 B2 | 6/2003 | Gordon et al. |
| 6,582,728 B1 | 6/2003 | Platz et al. |
| 6,586,006 B2 | 7/2003 | Roser et al. |
| 6,589,560 B2 | 7/2003 | Foster et al. |
| 6,592,904 B2 | 7/2003 | Platz et al. |
| 6,630,169 B1 | 10/2003 | Bot et al. |
| 6,638,495 B2 | 10/2003 | Weers |
| 6,649,911 B2 | 11/2003 | Kawato |
| 6,652,837 B1 | 11/2003 | Edwards et al. |
| 6,655,379 B2 | 12/2003 | Clark et al. |
| 6,673,335 B1 | 1/2004 | Platz et al. |
| 6,681,767 B1 | 1/2004 | Patton et al. |
| 6,685,967 B1 | 2/2004 | Patton et al. |
| 6,737,045 B2 | 5/2004 | Patton et al. |
| 6,737,066 B1 | 5/2004 | Moss |
| 6,752,893 B2 | 6/2004 | Frieder et al. |
| 6,797,258 B2 | 9/2004 | Platz et al. |
| 6,811,792 B2 | 11/2004 | Roser et al. |
| 6,825,031 B2 | 11/2004 | Franks et al. |
| 6,893,657 B2 | 5/2005 | Roser et al. |
| 6,921,527 B2 | 7/2005 | Platz et al. |
| 6,946,117 B1 | 9/2005 | Schutt |
| 7,052,678 B2 | 5/2006 | Vanbever |
| 7,056,495 B2 | 6/2006 | Roser |
| 7,097,827 B2 | 8/2006 | Platz |
| 7,101,576 B2 | 9/2006 | Hovey |
| 7,138,141 B2 | 11/2006 | Platz |
| 7,192,919 B2 | 3/2007 | Tzannis |
| 7,300,919 B2 | 11/2007 | Patton |
| 7,306,787 B2 | 12/2007 | Tarara |
| 7,393,544 B2 | 7/2008 | Dellamary |
| 7,442,388 B2 | 10/2008 | Weers |
| 7,521,069 B2 | 4/2009 | Patton |
| 7,628,978 B2 | 12/2009 | Weers |
| 2001/0035184 A1 | 11/2001 | Schuler et al. ......... 128/203.15 |
| 2002/0017295 A1 | 2/2002 | Weers |
| 2002/0052310 A1 | 5/2002 | Edwards |
| 2002/0127188 A1 | 9/2002 | Platz |
| 2002/0132787 A1 | 9/2002 | Eljamal |
| 2002/0168322 A1 | 11/2002 | Clark |
| 2002/0187106 A1 | 12/2002 | Weers |
| 2002/0192164 A1 | 12/2002 | Patton |
| 2003/0035778 A1 | 2/2003 | Platz |
| 2003/0072718 A1 | 4/2003 | Platz |
| 2003/0086877 A1 | 5/2003 | Platz |
| 2003/0092666 A1 | 5/2003 | Eljamal |
| 2003/0096744 A1 | 5/2003 | Ashkenazi |
| 2003/0113273 A1 | 6/2003 | Patton |
| 2003/0113900 A1 | 6/2003 | Tunnacliffe |
| 2003/0185765 A1 | 10/2003 | Platz |
| 2003/0198601 A1 | 10/2003 | Platz |
| 2003/0203036 A1 | 10/2003 | Gordon |
| 2003/0215512 A1 | 11/2003 | Foster |
| 2004/0096401 A1 | 5/2004 | Patton |
| 2004/0105820 A1 | 6/2004 | Weers |
| 2004/0156792 A1 | 8/2004 | Tarara |
| 2004/0219206 A1 | 11/2004 | Roser |
| 2005/0074449 A1 | 4/2005 | Bot |
| 2005/0147566 A1 | 7/2005 | Fleming |
| 2005/0186143 A1 | 8/2005 | Stevenson |
| 2005/0214224 A1 | 9/2005 | Weers |
| 2006/0159625 A1 | 7/2006 | Tarara et al. ............ 424/45 |
| 2006/0159629 A1 | 7/2006 | Tarara |
| 2006/0165606 A1 | 7/2006 | Tarara |

FOREIGN PATENT DOCUMENTS

| | | |
|---|---|---|
| AU | 714998 | 8/1997 |
| AU | 757337 | 4/1999 |
| AU | 714998 | 1/2000 |
| BE | 902257 | 8/1985 |
| CA | 2036844 | 8/1991 |
| CA | 2126034 | 1/1995 |
| CA | 2136704 | 5/1995 |
| DE | 161072 | 6/1905 |
| DE | 471490 | 8/1931 |
| DE | 1080265 | 4/1960 |
| DE | 3141498 | 4/1983 |
| DE | 3713326 | 3/1996 |
| EP | 0015123 | 12/1982 |
| EP | 0111216 | 6/1984 |
| EP | 0072046 | 1/1986 |

(56) References Cited

FOREIGN PATENT DOCUMENTS

| | | |
|---|---|---|
| EP | 0257956 | 8/1986 |
| EP | 0090356 | 7/1987 |
| EP | 0136030 | 7/1988 |
| EP | 0140489 | 4/1989 |
| EP | 0325936 | 8/1989 |
| EP | 0380340 | 3/1990 |
| EP | 0372777 | 6/1990 |
| EP | 0415567 | 3/1991 |
| EP | 0174759 | 4/1991 |
| EP | 0139286 | 8/1991 |
| EP | 0229610 | 10/1991 |
| EP | 0520748 | 12/1992 |
| EP | 0372777 | 1/1993 |
| EP | 0391896 | 3/1994 |
| EP | 0536204 | 4/1994 |
| EP | 0363569 | 5/1994 |
| EP | 0611567 | 8/1994 |
| EP | 0222313 | 9/1994 |
| EP | 0553298 | 11/1994 |
| EP | 0463653 | 1/1995 |
| EP | 0640347 | 3/1995 |
| EP | 0282179 | 5/1995 |
| EP | 0430045 | 5/1995 |
| EP | 0653205 | 5/1995 |
| EP | 0653237 | 5/1995 |
| EP | 0655237 | 5/1995 |
| EP | 0656205 | 6/1995 |
| EP | 0658101 | 6/1995 |
| EP | 0513127 | 7/1995 |
| EP | 0493437 | 8/1995 |
| EP | 05562556 | 8/1995 |
| EP | 0616525 | 9/1995 |
| EP | 0474874 | 10/1995 |
| EP | 0499344 | 10/1995 |
| EP | 0366303 | 12/1995 |
| EP | 0587790 | 1/1996 |
| EP | 0605578 | 1/1996 |
| EP | 0588897 | 2/1996 |
| EP | 05365235 | 1/1997 |
| EP | 0356154 | 4/1997 |
| EP | 0433679 | 5/1997 |
| EP | 0274431 | 7/1998 |
| EP | 0616524 | 10/1998 |
| EP | 0539522 | 12/1998 |
| EP | 0656203 | 5/1999 |
| EP | 0600730 | 10/1999 |
| EP | 0656206 | 8/2001 |
| EP | 0714905 | 4/2002 |
| EP | 0743860 | 4/2002 |
| EP | 1019022 | 4/2003 |
| EP | 0681843 | 6/2003 |
| EP | 0773781 | 10/2003 |
| EP | 0904056 | 10/2003 |
| EP | 0663840 | 12/2003 |
| ES | 8403520 | 6/1984 |
| FR | 2238476 | 2/1975 |
| GB | 1265615 | 3/1972 |
| GB | 1288094 | 9/1972 |
| GB | 1381566 | 1/1975 |
| GB | 1477775 | 6/1977 |
| GB | 1518843 | 7/1978 |
| GB | 1533012 | 11/1978 |
| GB | 2065659 | 12/1979 |
| GB | 2105189 | 3/1983 |
| GB | 2126586 | 3/1984 |
| GB | 2187191 | 9/1987 |
| GB | 2237510 | 5/1991 |
| JP | 52139789 | 11/1977 |
| JP | 58215695 | 12/1983 |
| JP | 59095885 | 6/1984 |
| JP | 60244286 | 12/1985 |
| JP | 62228272 | 10/1987 |
| JP | 62255434 | 11/1987 |
| JP | 03038592 | 2/1991 |
| JP | 6100464 | 4/1994 |
| JP | 3264537 | 12/2001 |
| RU | 93008753 | 5/1993 |
| SU | 91263780 | 12/1991 |
| SU | 9205196 | 6/1992 |
| WO | WO 8604095 | 7/1986 |
| WO | WO 8700196 | 1/1987 |
| WO | WO 8702038 | 4/1987 |
| WO | WO 8705300 | 9/1987 |
| WO | WO 8801862 | 3/1988 |
| WO | WO 8808298 | 11/1988 |
| WO | WO 8905632 | 6/1989 |
| WO | WO 8906976 | 8/1989 |
| WO | WO 8908449 | 9/1989 |
| WO | WO 9005182 | 5/1990 |
| WO | WO 9011758 | 10/1990 |
| WO | WO 9013285 | 11/1990 |
| WO | WO 9015635 | 12/1990 |
| WO | WO 9015653 | 12/1990 |
| WO | WO 9104011 | 4/1991 |
| WO | WO 9104715 | 4/1991 |
| WO | WO 9108282 | 5/1991 |
| WO | WO 9111173 | 8/1991 |
| WO | WO 9112823 | 9/1991 |
| WO | WO 91/16444 | 10/1991 |
| WO | WO 9116038 | 10/1991 |
| WO | WO 9116862 | 11/1991 |
| WO | WO 9116882 | 11/1991 |
| WO | WO 9118091 | 11/1991 |
| WO | WO 9200107 | 1/1992 |
| WO | WO 9202133 | 2/1992 |
| WO | WO 9211050 | 7/1992 |
| WO | WO 9214444 | 9/1992 |
| WO | WO 9218110 | 10/1992 |
| WO | WO 9218164 | 10/1992 |
| WO | WO 9219243 | 11/1992 |
| WO | WO 9300951 | 1/1993 |
| WO | WO 9302834 | 2/1993 |
| WO | WO 9309832 | 5/1993 |
| WO | WO 9310758 | 6/1993 |
| WO | WO 9311743 | 6/1993 |
| WO | WO 9311744 | 6/1993 |
| WO | WO 9311745 | 6/1993 |
| WO | WO 9311746 | 6/1993 |
| WO | WO 9312240 | 6/1993 |
| WO | WO 9313752 | 7/1993 |
| WO | WO 9314172 | 7/1993 |
| WO | WO 9317663 | 9/1993 |
| WO | WO 9323065 | 11/1993 |
| WO | WO 9323110 | 11/1993 |
| WO | WO 9404133 | 3/1994 |
| WO | WO 9407514 | 4/1994 |
| WO | WO 9408552 | 4/1994 |
| WO | WO 9408627 | 4/1994 |
| WO | WO 9413271 | 6/1994 |
| WO | WO 9422423 | 10/1994 |
| WO | WO 9424263 | 10/1994 |
| WO | WO 9500127 | 1/1995 |
| WO | WO 9500128 | 1/1995 |
| WO | WO 9501324 | 1/1995 |
| WO | WO 9505194 | 2/1995 |
| WO | WO 9506126 | 3/1995 |
| WO | WO 9515118 | 6/1995 |
| WO | WO 9517195 | 6/1995 |
| WO | WO 9520979 | 6/1995 |
| WO | WO 9523613 | 9/1995 |
| WO | WO 9524183 | 9/1995 |
| WO | WO 9524892 | 9/1995 |
| WO | WO 9527476 | 10/1995 |
| WO | WO 95/31479 | 11/1995 |
| WO | WO 9528944 | 11/1995 |
| WO | WO 9531182 | 11/1995 |
| WO | WO 9531964 | 11/1995 |
| WO | WO 9533488 | 12/1995 |
| WO | WO 9603116 | 2/1996 |
| WO | WO 9603978 | 2/1996 |
| WO | WO 9607399 | 3/1996 |
| WO | WO 9637399 | 3/1996 |
| WO | WO 9809085 | 3/1996 |
| WO | WO 96/09814 | 4/1996 |

(56) References Cited

FOREIGN PATENT DOCUMENTS

| | | |
|---|---|---|
| WO | WO 9609814 | 4/1996 |
| WO | WO 9611745 | 4/1996 |
| WO | WO 9615814 | 5/1996 |
| WO | WO 9618388 | 6/1996 |
| WO | WO 9619197 | 6/1996 |
| WO | WO 9619198 | 6/1996 |
| WO | WO 9619199 | 6/1996 |
| WO | WO 9619968 | 7/1996 |
| WO | WO 9626746 | 9/1996 |
| WO | WO 9627393 | 9/1996 |
| WO | WO 96/32096 | 10/1996 |
| WO | WO 96/32149 | 10/1996 |
| WO | WO 9632096 | 10/1996 |
| WO | WO 9632116 | 10/1996 |
| WO | WO 9632149 | 10/1996 |
| WO | WO 9636314 | 11/1996 |
| WO | WO 9640049 | 12/1996 |
| WO | WO 9640068 | 12/1996 |
| WO | WO 9640077 | 12/1996 |
| WO | WO 9640277 | 12/1996 |
| WO | WO 9640285 | 12/1996 |
| WO | WO 9703649 | 2/1997 |
| WO | WO 9713503 | 4/1997 |
| WO | WO 97/25086 | 7/1997 |
| WO | WO 9725086 | 7/1997 |
| WO | WO 9726863 | 7/1997 |
| WO | WO 9732609 | 9/1997 |
| WO | WO 9734689 | 9/1997 |
| WO | WO 9735562 | 10/1997 |
| WO | WO 9736574 | 10/1997 |
| WO | WO 9736578 | 10/1997 |
| WO | WO 9740819 | 11/1997 |
| WO | WO 9741833 | 11/1997 |
| WO | WO 9744012 | 11/1997 |
| WO | WO 9744013 | 11/1997 |
| WO | WO 9800111 | 1/1998 |
| WO | WO 9801161 | 1/1998 |
| WO | WO 9805302 | 2/1998 |
| WO | WO 9807414 | 2/1998 |
| WO | WO 9808519 | 3/1998 |
| WO | WO 9813031 | 4/1998 |
| WO | WO 9816205 | 4/1998 |
| WO | WO 9817257 | 4/1998 |
| WO | WO 9824882 | 6/1998 |
| WO | WO 98/31346 | 7/1998 |
| WO | WO 9825098 | 7/1998 |
| WO | WO 9829096 | 7/1998 |
| WO | WO 9829097 | 7/1998 |
| WO | WO 9829099 | 7/1998 |
| WO | WO 9829140 | 7/1998 |
| WO | WO 9830207 | 7/1998 |
| WO | WO 9831346 | 7/1998 |
| WO | WO 9833480 | 8/1998 |
| WO | WO 9833487 | 8/1998 |
| WO | WO 9841186 | 9/1998 |
| WO | WO 9851282 | 11/1998 |
| WO | WO 9858989 | 12/1998 |
| WO | WO 9906026 | 2/1999 |
| WO | WO 9909956 | 3/1999 |
| WO | WO 99/16419 | 4/1999 |
| WO | WO 9916419 | 4/1999 |
| WO | WO 9916420 | 4/1999 |
| WO | WO 9916421 | 4/1999 |
| WO | WO 9916422 | 4/1999 |
| WO | WO 9945987 | 6/1999 |
| WO | WO 9725863 | 7/1999 |
| WO | WO 9932083 | 7/1999 |
| WO | WO 9932098 | 7/1999 |
| WO | WO 99/38493 | 8/1999 |
| WO | WO 99/45986 | 9/1999 |
| WO | WO 99/45987 | 9/1999 |
| WO | WO 99/47196 | 9/1999 |
| WO | WO 9944583 | 9/1999 |
| WO | WO 9945986 | 9/1999 |
| WO | WO 9947196 | 9/1999 |
| WO | WO 99/66903 | 12/1999 |
| WO | WO 9966903 | 12/1999 |
| WO | 0000176 | 1/2000 |
| WO | WO 00/10541 | 3/2000 |
| WO | WO 0010541 | 3/2000 |
| WO | WO 00/21594 | 4/2000 |
| WO | WO 0021594 | 4/2000 |
| WO | WO 0027360 | 5/2000 |
| WO | 0000215 | 6/2000 |
| WO | WO 0056282 | 9/2000 |
| WO | WO 0061157 | 10/2000 |
| WO | WO 0072904 | 12/2000 |
| WO | WO 01/00263 | 1/2001 |
| WO | 0113892 | 3/2001 |
| WO | WO 01/13892 | 3/2001 |
| WO | WO 0113891 | 3/2001 |
| WO | WO 0113892 | 3/2001 |
| WO | WO 0126683 | 4/2001 |
| WO | WO 0132144 | 5/2001 |
| WO | WO 0164254 | 9/2001 |
| WO | WO 01/85136 | 11/2001 |
| WO | WO 01/85137 | 11/2001 |
| WO | WO 0185136 | 11/2001 |
| WO | WO 0185137 | 11/2001 |
| WO | WO 0187278 | 11/2001 |
| WO | WO0195874 | 12/2001 |
| WO | WO 0209674 | 2/2002 |
| WO | WO 02067542 | 11/2002 |
| WO | WO 03002834 | 1/2003 |
| WO | WO 2006002140 | 1/2006 |

OTHER PUBLICATIONS

Ben-Jebria et al., "Large Porous Particles for Sustained Protection for Carbuchol-Induced Bronchoconstriction in Guinea Pigs." (1999) Pharm. Res., vol. 16(4), pp. 556-561.

Hauser et al., "Interactions of Divalent Cations with Phosphatidylserine Bilayer Membranes." (1984) Biochemistry, vol. 23(1), pp. 34-41.

Zarif et al., "Amphotericin B Chocleates as a Novel Oral Delivery System for the Treatment of Fungal Infections," (1999) Proceed. Int'l. Symp. Control. Rel. Bioact. Mater., Controlled Release Society Inc.: p. 964-965 (ISSN: 1022-0178).

A. Adjei and J. Garren, "Pulmonary Delivery of Peptide Drugs: Effect of Particle Size on Bioavailability of Leuprolide Acetate in Healthy Male Volunteers," Pharmaceutical Research 1990, vol. 7(6): pp. 565-569.

C. Roth et al., "Production of Hollow Spheres," Pargamon Press, vol. 19 (No. 7), p. 939-942, 1988.

Abdellaziz Ben-Jebria et al., "Large Porous Particles for Sustained Protection from Carbachol-Induced Brachoconstriction in Guinea Pigs," Pharm Res. vol. 16 (No. 4), pp. 555-561.

Zarif et al., "Amphotericin B Cochleates as a Novel Oral Delivery System," International Symposium, p. 964-965.

Hauser et al., "Interactions of Divalent Cations with Phosphatidylserine Bilayer Membranes." Biochem. p. 34-41.

Franks Felix et al "Materials Science and the Production of Shelf-Stable Biologicals" Pharm Technol 24:24 (1991).

Franks Felix "Separation, Improved Freeze-Drying, An Analysis of the Basic Scientific Principles" Process Biochem 24(1):iii-viii (1989).

Franks Felix "Accelerated stability testing of bioproducts: attractions and pitfalls" TIBTECH 12:114 (1994).

French Donna L et al "The Influence of Formulation on Emission, Deaggregation and Deposition of Dry Powders for Inhalation" J Aerosol Sci 27(5):769-783 (1996).

Fukuoka Eihel et al "Glassy State of Pharmaceuticals. V. Relaxation during Cooling and Heating of Glass by Differential Scanning Calorimetry" Chem Pharm Bull 39(8):2087-2090 (1991).

Garrett et al "Membrane Phase Transitions" Biochemistry, Saunders College Pub, p. 301-305 (1995).

Goldbach P et al "Spray-Drying of Liposomes for a Pulmonary Administration. I. Chemical Stability of Phospholipds" Drug Dev Ind Pharm 19(19):2611-2622 (1993).

(56) References Cited

OTHER PUBLICATIONS

Goldman JM et al "Inhaled micronised gentamicin powder: a new delivery system" Thorax 45:939-940 (1990).
Gonda I et al "Characterisation of Hygroscopic Inhalation Aerosols" Particle Size Analysis 1981, NG Stanley-Wood ed, Wiley Heyden Ltd, p. 31 (1982).
Gordon Manfred et al "Ideal Copolymers and the Second-Order Transitions of Synthetic Rubbers. I. Non-Crystalline Copolymers" J Appl Chem 2:493 (1952).
Green JL et al "Phase Relations and Vitrification in Saccharide-Water Solutions and the Trehalose Anomaly" J Phys Chem 93:2880-2882 (1989).
Green JL et al "The Protein-Glass Analogy: Some Insights from Homopeptide Comparisons" J Phys Chem 98:13780-13790 (1994).
Gupta A et al "Single virus particle mass detection using microresonators with nanoscale thickness" Appl Phys Lett 84(11):1976 (2004).
Hahn Lorenz et al "Solid Surfactant Solutions of Active Ingredients in Sugar Esters" Pharm Res 6(11):958 (1989).
Haitsma Jack J et al "Exogenous surfactant as a drug delivery agent" Adv Drug Del Rev 47:197-207 (2001).
Hancock Bruno C et al "The Effect of Temperature on Water Vapor Sorption by Some Amorphous Pharmaceutical Sugars" Pharm Dev Technol 4(1):125-134 (1999).
Hancock Bruno C et al "The Use of Solution Theories for Predicting Water Vapor Absorption by Amorphous Pharmaceutical Solids: A Test of the Flory-Huggins and Vrentas Models" Pharm Res 10(9):1262 (1993).
Hancock Bruno C et al "The Relationship Between the Glass Transition Temperature and the Water Content of Amorphous Pharmaceutical Solids" Pharm Res 11(4):471 (1994).
Hancock Bruno C et al "Molecular Mobility of Amorphous Pharmaceutical Solids Below Their Glass Transition Temperatures" Pharm Res 12(6):799 (1995).
Hancock Bruno C et al "A Pragmatic Test of a Simple Calorimetric Method for Determining the Fragility of Some Amorphous Pharmaceutical Materials" Pharm Res 15(5):762 (1998).
Hancock Bruno C et al "Characteristics and Significance of the Amorphous State in Pharmaceutical Systems" J Pharm Sci 86(1):1-12 (1997).
Hanes Justin "Polymer Microspheres for Vaccine Delivery" Thesis (PhD) archived by Massachusetts Institute of Technology Library Jul. 31, 1997 and catalogued Dec. 5, 1997 (1996).
Hanes J et al "Porous Dry-Powder PLGA Microspheres Coated with Lung Surfactant for Systemic Insulin Delivery Via the Lung" Controlled Release Society, Proc Intl Symp Control Rel Bioact Mater 24 #229 p. 57 (1997).
Harwood Colin F "Compaction Effect on Flow Property Indexes for Powders" J Pharm Sci 60(1):161 (1971).
Hatley Ross H et al "Stabilization of Labile Materials by Amorphous Carbohydrates Glass Fragility and the Physicochemical Properties that Make Trehalose a Superior Excipient" Pharm Res 13(9 Suppl):S-274, Abstract PDD 7165 (1996).
Hauser Helmut et al "Comparative structural aspects of cation binding to phosphatidylserine bilayers" Biochim Biophys Acta 813:343-348 (1985).
Heitefuss Rudolf et al "The Stabilization of Extracts of Cabbage Leaf Proteins by Polyhydroxy Compounds for the Electrophoretic and Immunological Studies" Arch Biochem Biophys 85:200-208 (1959).
Heller Martin C "Protein Formulation and Lyophilization Cycle Design: Prevention of Damage Due to Freeze-Concentration Induced Phase Separation" Biotechnol Bioeng 63:166 (1999).
Herrington Thelma M et al "Physico-chemical studies on sugar glasses. I. Rates of crystallization" J Food Technol 19:409-425 (1984).
"Method of Aerosol Particle Size Characterization" Pharmaceutical Inhalation Aerosol Technology, Anthony J Hickey ed, Marcel Dekker pub, Ch 8 p. 219 (1992).
Hickey Anthony J et al "Behavior of Hygroscopic Pharmaceutical Aerosols and the Influence of Hydrophobic Additives" Pharm Res 10(1):1 (1993).
Hoener Betty-ann et al "Factors Influencing Drug Absorption and Drug Availability" Modern Pharmaceutics, GS Banker et al ed, Marcel Dekker pub, Ch 4 p. 121-153 (1996).
Hrkach Jeffrey S et al "Synthesis of Poly(L-lactic acid-co-L-lysine) Graft Copolymers" Macromolecules 28:4736-4739 (1995).
Hrkach Jeffey S et al "Poly(L-lactic acid-co-amino acid) Graft Copolymeers: A Class of Functional Biodegradable Biomaterials" Hydrogels and Biodegradable Polymers for Bioapplications, Raphael M Ottenbrite ed, Amn Chem Soc 208$^{th}$ National Meeting, Washington, DC Aug. 21-26, 1994, ACS Symposium Series 627, Ch 8 p. 93 (1996).
Huster Daniel et al "Investigation of Phospholipid Area Compression Induced by Calcium-Mediated Dextran Sulfate Interaction" Biophys J 77:879-887 (1999).
Huster Daniel et al "Strength of $Ca^{2+}$ Binding to Retinal Lipid Membranes: Consequences for Lipid Organization" Biophys J 78:3011-3018 (2000).
Ibrahim AL et al "Spray Vaccination with an Improved F Newcastle Disease Vaccine. A Comparison of Efficacy with the B1 and La Sota Vaccines" Br Vet J 139(3):213 (1983).
Igaki Naoya et al "The Inhibition of Maillard Reaction by L-Lysine in Vitro" J Japan Diab Soc 34(5):403-407 (1991).
Iglesias Héctor A et al "Adsorption Isotherm of Amorphous Trehalose" J Sci Food Agric 75:183-186 (1997).
Product Sheet for INTAL® Inhaler (Rhone-Poulenc Rorer Pharmaceuticals Inc) 6p (2006).
Jacobson Kenneth et al "Phase Transitions and Phase Separations in Phospholipid Membranes Induced by Changes in Temperature, pH, and Concentration of Bivalent Cations" Biochemistry 14(1):182 (1975).
Jameel Feroz et al "Freeze Drying Properties of Some Oligonucleotides" Pharm Dev Technol 6(2):151-157 (2001).
Johansen Påi et al "Technological considerations related to the up-scaling of protein microencapsulation by spray-drying" Eur J Pharm Biopharm 50:413-417 (2000).
Jovanovic-Peterson Lois et al "Jet-Injected Insulin Is Associated with Decreased Antibody Production and Postprandial Glucose Variability when Compared with Needle-Injected Insulin in Gestational Diabetic Women" Diab Care 16(11):1479 (1993).
Kachura VI "Method of drying lactic acid bacteria" Vinodelle I Vinogradarstvo SSSR 2:49-50 (1985), Abstract.
Kanna Koichi et al "Denaturation of Fish Muscle Protein by Dehydration—V. Preventive Effect of Sugars and Sugar-alcohols of Protein Denaturation by Dehydration" Bull Tokai Reg Fish Res Lab 77:69 (1974).
Karmas Ralvo et al "Effect of Glass Transition on Rates of Nonenzymatic Browning in Food Systems" J Agric Food Chem 40:873-879 (1992).
Khan Riaz et al "Cyclic Acetals of 4,1',6'-Trichloro-4,1',6'-Trideoxy-gelacto-Surcrose and Their Conversion into Methyl Ether Derivatives" Cabrohydr Res 198:275-283 (1990).
Khan Riaz "Chemistry and New Uses of Sucrose: How Important?" Pure Appl Chem 56(7):833-844 (1984).
Klein TM et al "High-velocity microprojectiles for delivering nucleic acids into living cells" Nature 327:70 (1987).
Kočova S et al "The failure properties od some "simple" and "complex" powders and the significance of their yield locus parameters" Powder Technol 8:33-55 (1973).
Kumar Vijay et al "Preparation, characterization, and tabletting properties of a new cellulose-based pharmaceutical aid" Intl J Pharm 235:129-140 (2002).
Kwon Kyung Ok et al "Calcium Ion Adsorption on Phospholipid Bilayers. Theoretical Interpretation" J Jpn Oil Chem Soc 43(1):23 (1994).
Labrude P et al "Protective Effect of Sucrose on Spray Drying of Oxyhemoglobin" J Pharm Sci 78(3):223 (1989).
Labuza Ted et al "Glass Transition Temperatures of Food Systems" [on-line] [retrieved Sep. 2005] Retrieved from the Internet <URL: http://www.faculty.che.umn.edu/fscn/TedLebuza/pdf_files/isotherm_folder/Tg%20compilation.pdf> p. 1-31 (1992).

(56) References Cited

OTHER PUBLICATIONS

Lai MC et al "Solid-State Chemical Stability of Proteins and Peptides" J Pharm Sci 88(5):489 (1999).
Laube Beth L et al "Targeting Aerosol Deposition in Patients with Cystic Fibrosis, Effects of Alterations in Particle Size and Inspiratory Flow Rate" Chest 118(4):1069 (2000).
Ledl Franz et al "New Aspects of the Melliard Reaction in Foods and in the Human Body" Angew Chem Int Ed Engl 29(6):565-594 (1990).
Lee CK, Developments in food carbohydrate (Developments series,) Applied Science Pub Ltd, Essex, England, $2^{nd}$ ed, Table of Contents, 4pg (1980).
Lee Geoffrey "Spray-Drying of Proteins, Introduction: Why Spray-Dry a Protein?" Rational Design of Stable Protein Formulations, Carpenter and Manning ed, Kluwer Academic/Plenum Pub NY, Ch 6 p. 135 (2002).
Lehninger Albert L "DNA and the Structure of the Genetic Material" Biochemistry. The Molecular Basis of Cell Structure and Function, Worth Pub. $2^{nd}$ ed, Ch 31 p. 859-890 (1975).
Leslie Samuel B et al "Trehalose and Sucrose Protect Both Membranes and Proteins in Intact Bacteria during Drying" Appl Environ Microbiol 61(10):3592 (1995).
Leuner Christian et al "Improving drug solubility for oral delivery using solid dispersions" Eur J Pharm Biopharm 50:47-60 (2000).
Levine Harry et al "Another View of Trehalose for Drying and Stabilizing Biological Materials" BioPharm p. 36 (1992).
Li Zhili et al "Realistic In Vitro Assessment of Dry Powder Inhalers" Resp Drug Del VIII p. 687 (2002).
Lin Shan-Yang et al "Solid particulates of drug-β-cyclodextrin inclusion complexes directly prepared by a spray-drying technique" Intl J Pharm 56:249-259 (1989).
Lis LJ et al "Adsorption of Divalent Cation to a Variety of Phosphatidylcholine Bilayers" Biochemistry 20:1771-1777 (1981).
Lis LJ et al "Binding of Divalent Cations to Dipalmitoylphosphatidylcholine Bilayers and Its Effect on Bilayer Interaction" Biochemistry 20:1761-1770 (1981).
Liu Jinsong et al "Dynamics of Pharmaceutical Amorphous Solids: The Study of Enthalpy Relaxation by Isothermal Microcalorimetry" J Pharm Sci 91(6):1853 (2002).
Louey Margaret D et al "Controlled Release Products for Respiratory Delivery" APR 7(4):82-87, 11pp (2004) [on-line] [retrieved on Sep. 2005] Retrieved from the Internet <URL: http://www.americanpharmaceuticalreview.com.article.aspx?articlel=77>.
Louis P et al "Survival of *Escherichia coli* during drying and storage in the presence of compatible solutes" Appl Microbiol Biotechnol 41:684-688 (1994).
Lueckel Barbara et al "Effects of Formulation and Process Variables on the Aggregation of Freeze-Dried Interleukin-6 (IL-6) After Lyophilization and on Storage" Pharm Dev Technol 3(3):337-346 (1996).
Mackenzie AP "Collapse during freeze drying—qualitative and quantitative aspects" Freeze Drying and Advanced Food Technology, SA Goldblith et al ed, Academic Press, Ch 19 p. 277 (1975).
Makower Benjamin et al "Sugar Crystallization. Equilibrium Moisture Content and Crystallization of Amorphous Sucrose and Glucose" Agr Food Chem 4(1):72 (1956).
Martin Alfred et al "States of Matter and Phase Equilibria" Physical Pharmacy. Physical Chemical Principles in the Pharmaceutical Sciences, $3^{rd}$ ed, Lea & Febiger, Phila, Ch 4 p. 62 (1983).
Masinde Lwandiko E et al "Aerosolized aqueous suspensions of poly(L-lactic acid) microspheres" Intl J Pharm 100:123-131 (1993).
Masters K "Drying of Droplets/Sprays" Spray Drying Handbook, Longman Scientific & Technical, England, $5^{th}$ ed, Ch 8 p. 309-352 (1991).
Masters K "Applications of Spray Drying" Spray Drying Handbook, Longman Scientific & Technical, England, $5^{th}$ ed, Ch 13 p. 491 (1991).
Masters K "Applications in the Food Industry, Milk Products" Spray Drying Handbook, Longman Scientific & Technical, England, $5^{th}$ ed, Ch 15 p. 587 (1991).

Matsuda Yoshihisa et al "Amorphism and Physicochemical Stability of Spray-dried Frusemide" J Pharm Pharmacol 44:627-633 (1992).
Mattern Markus et al "Formulation of Proteins in Vacuum-Dried Glasses. II. Process and Storage Stability in Sugar-Free Amino Acid Systems" Pharm Dev Technol 4(2):199-208 (1999).
Millqvist-Fureby Anna et al "Spray-drying of trypsin—surface characterisation and activity preservation" Intl J Pharm 188:243-253 (1999).
Millqvist-Fureby Anna et al "Surface characterisation of freeze-dried protein/carbohydrate mixtures" Intl J Pharm 191:103-114 (1999).
Miller Danforth P et al "Stabilization of Lactate Dehydrogenase Following Freeze-Thawing and Vacuum-Drying in the Presence of Trehalose and Borate" Pharm Res 15(8):1215 (1998).
Molina MC et al "The stability of lyophilized lipid/DNA complexes during prolonged storage" J Pharm Sci 93(9):2259-73 (1993), Abstract, 1p [on-line] [retrieved Sep. 2005] Retrieved from the Internet <URL: http://www.ncbi.nlm.nih.gov> (2004).
Monnier Vincent M et al "Mechanisms of Protection against Damage Mediated by the Meillard Reaction in Aging" Gerontology 37:152-165 (1991).
Morel Penelope A et al "Crossregulation Between Th1 and Th2 Cells" Crit Rev Immun 18:275-303 (1998).
Mouradian Robert et al "Degradation of Functional Integrity during Long-Term Storage of a Freeze-Dried Biological Membrane" Cryobiology 22:119-127 (1985).
Moynihan Cornelius T et al "Dependence of the Glass Transition Temperature on Heating and Cooling Rate" J Phys Chem 78(26):2673 (1974).
Muller VM et al "On the Influence of Molecular Forces on the Deformation of an Elastic Sphere and its Sticking to a Rigid Plane" J Colloid Interface Sci 77(1):91 (1980).
Mumenthaler Marco et al "Feasibility Study on Spray-Drying Protein Pharmaceuticals: Recombinant Human Growth Hormone and Tissue-Type Plasminogen Activator" Pharm Res 11(1):12 (1994).
Murphy Brian R et al "Immunization Against Virus Disease. Viral Antigens Recognized by the Immune System" Fields Virology, $3^{rd}$ ed, BN Fields et al ed, Raven Pub, Phila, Ch 16 at p. 468, $1^{st}$ full parag, $1^{st}$ col, line 26-33 (1996).
Murphy Brian R et al "Immunization Against Viruses, Immunity to Virus Infections" Virology, $2^{nd}$ ed. vol. 1, BN Fields et al ed, Raven Press, NY, Ch 19 p. 469 (1990).
Mütterlein R at al "New Technology for Generating Inhalation Aerosols—Preliminary Results with the Piezoelectrical Pocket-Inhaler" J Aerosol Med 1:231 (1988).
Nabel Gary J et al "Clinical Protocol, Immunotherapy of Malignancy by In Vivo Gene Transfer into Tumors" Human Gene Ther 3:399-410 (1992).
Nasel Gary J et al "Direct gene transfer with DNA-liposome complexes in melanoma: Expression, biologic activity, and lack of toxicity in humans" Proc Nat Acad Sci USA 90:11307-11311 (1993).
Nani Venketesh et al "Physicochemical Stability of Crystalline Sugars and Their Spray-Dried Forms: Dependence upon Relative Humidity and Suitability for Use in Powder Inhalers" Drug Dev Ind Pharm 24(10):895-909 (1998).
Naini Venkatesh et al "Particles for Inhalation Produced by Spray Drying and Electrostatic Precipitation of Different Protein-Sugar Solutions" Resp Drug Del V, p. 382 (1996).
Natarajan P "Crystallization Conditions for VIPER Entries" [on-line] [retrieved Nov. 4, 2004] Retrieved from the Internet <URL: http://www.xtai/tsinghua.edu.cn/research/groups/web/material/Virus%20 Crystallization%20Page.htm> 5 pg (last updated Jan. 3, 2002) <.
Niven Ralph W "Delivery of Biotherapeutics by Inhalation Aerosol" Crit Rev Thera Drug Carrier Sys 12(2&3):151-231 (1995).
Niven Ralph W "Delivery of Biotherapeutics by inhalation Aerosols" Pharm Technol p. 72-75, p. 80 (1993).
Norberg Jan et al "Glass transition in DNA from molecular dynamics simulations" Proc Natl Acad Sci USA 93:10173-10176 (1996).

(56) References Cited

OTHER PUBLICATIONS

Notter Robert H "Physical Chemistry and Physiological Activity of Pulmonary Surfactants" Sufactant Replacement Therapy, Shapiro and Notter eds, Alan R Liss pub, Ch 2 p. 19-70 (1989).
Odegard Peggy Soule et al "Inhaled Insulin: Exubera" Ann Pharmacother 39:843 (2005).
Ohtake Satoshi et al "Effect of pH, Counter Ion, and Phosphate Concentration on the Glass Transition Temperature of Freeze-Dried Sugar-Phosphate Mixtures" Pharm Res 21(9):1615 (2004).
Okamoto Hirokazu et al "Dry Powders for Pulmonary Delivery of Peptides and Proteins" KONA Powder and Particle No. 20, p. 71-83 (2002).
Oksanen Cynthia A et al "This Relationship Between the Glass Transition Temperature and Water Vapor Aboorption by Poly(vinylpyrrolidone)" Pharm Res 7(6):657-657, and erratum p. 974 (1990).
Okumura K et al "Intratracheal delivery of calcitonin dry powder in rats and human volunteers" Special issue Pulmonary administration and delivery STP Pharm Sci 4(1), 5p (1994).
Onodera Natsuo et al "Glass Transition in Dehydrated Amorphous Solid" Bull Chem Soc Jpn 41(9):222 (1999).
"Oral Solid Dosage Forms" Remington's Pharmaceutical Sciences, 18$^{th}$ ed, Mack Pub, Ch 89 p. 1646.
Ormrod Douglas J et al "Dietary chitosen inhibits hypercholesterolaemia and atherogenesis in the apolipoprotein E-deficient mouse model of atherosclerosis" Atherosclerosis 138:329-334 (1998).
Owens DR et al "Alternative routes of insulin delivery" Diab Med 20:886-898 (2003).
Palmer KJ et al "Sugar Crystallization, X-Ray Diffractometer and Microscopic Investigation of Crystallization of Amorphous Sucrose" Agric Food Chem 4(1):77-81 (1956).
Papahadjopoulos D et al "Cochleate Lipid Cylinders: Formation by Fusion of Unilamellar Lipid Vesicles" Biochim Biophys Acta 394:483-491 (1975).
Parasassi T et al "Calcium-Induced Phase Separation in Phospholipid Bilayers, A Florescence Anisotropy Study" Cell Mol Biol 32(3):261-266 (1986).
Parks Geroge S et al "Studies on Glass II. The Transition between the Glassy and Liquid States in the Case of Glucose" J Phys Chem 31:1366 (1928).
Patel Mayank M et al "Degradation Kinetics of High Molecular Weight Poly(L-Lactide) Micospheres and Release Mechanism of Lipid:DNA Complexes" J Pharm Sci 93(10):2573 (2004).
Pearlman R et al "Formulation Strategies for Recombinant Proteins: Human Growth Hormone and Tissue Plasminogen Activators" Therapeutic Peptides and Proteins, Formulation, Delivery and Targeting, Cold Spring Harbour, NY p. 23 (1989).
Pekarek Kathleen J et al "Double-walled polymer microspheres for controlled drug release" Nature 387:258 (1994).
Persson G et al "The bronchodilator response from inhaled terbutaline is influenced by the mass of small particles: a study on a dry powder inhaler (Turbuhaler®)" Eur Respir J 2:253-256 (1989).
"Pfizer/inhale Therapeutic Pulmonary Insulin Collaboration" Health News Daily 7(13): p. 4 (Jan. 20, 1995).
"Physical Tests and Determinations. (601) Aerosols, Metered-Dose Inhalers, and Dry Powder Inhalers" Pharmacopeial Forum 22(6):3065 (1996).
Phillips Elaine et al "Size Reduction of Peptides and Proteins by Jet-Milling" Resp Drug Del VI, p. 161 (1998).
Pikal Michael J et al "The Stability of Insulin in Crystalline and Amorphous Solids: Observation of Greater Stability for the Amorphous Form" Pharm Res 14(10):1379 (1997).
Pikal Michael J et al "Errata. The Stability of Insulin in Crystalline and Amorphous Solids: Observation of Greater Stability for the Amorphous Form" Pharm Res 15(2):362 (1998).
Pikal MJ et al "Thermal Decomposition of Amorphous β-Lactam Antibacterials" J Pharm Sci 66(9):1312 (1977).
Pikal Michael J "Freeze-Drying of Proteins. Part II: Formulation Selection" BioPharm 3(6):26-30 (1990).
Pine Stanley H et al "Oligosaccharides and Polysaccharides" Organic Chemistry, 4$^{th}$ ed, McGraw-Hill Intl, 15-3, p. 763 (1980).
Pisecky Jan "Evaporation and Membrane Filtration, 2.1, Basic Principles" Handbook of Milk Powder Manufacture, Niro A/S pub, Denmark, Sec 2 p. 3 (1997).
Pocchiari Maurizio et al "Amphotericin B: A Novel Class of Antiscraple Drugs" J Infect Dis 160(5):795 (1989).
Pestrelski Steven J et al "Separation of Freezing- and Drying-Induced Denaturation of Lyophilized Proteins Using Stress-Specific Stabilization" Arch Biochem Biophys 303(2):465-473 (1993).
Pestrelski Steven J et al "Optimization of Lyophilization Conditions for Recombinant Human Interleukin-2 by Dried-State Conformational Analysis Using Fourier-Transform Infrared Spectroscopy" Pharm Res 12(9):1250 (1995).
Quan Cynthia et al "Maillard Reaction Variant of a Recombinant Protein" Protein Science, Protein Society 9$^{th}$ Symposium, Boston, MA, Jul. 8-12, 1995, 4(Suppl 2):148, Protein Modification Abstract 490-T (1995).
Ramanujam R et al "Ambient-Temperature-Stable Molecular Biology Reagents" BioTechniques 14(3):470 (1993).
Reboiras MD "Activity coefficients of $CaCl_2$ and $MgCl_2$, in the presence of dipalmitoylphosphatidylcholine-phosphatidylinositol vesicles in aqueous media" Bioelectrochem Bioenerg 39:101-108 (1996).
Ringe D et al "The 'glass transition' In protein dynamics: what it is, why it occurs, and how to exploit it" Biophys Chem 105(2-3):667-80 (2003), Abstract [on-line] [retrieved Nov. 19, 2004] Retrieved from the Internet <URL: http://www.ncbi.nlm.nih.gov> 2003.
Roos Yrjöet al "Phase Transitions of Mixtures of Amorphous Polysaccharides and Sugars" Biotechnology Progress, Jerome S Schultz ed, 7(1):49 (1991).
Rosen Milton J "IV.A. The HLB Method" Surfactants and Interfacial Phenomena, 2$^{nd}$ ed, John Wiley pub, p. 326 (1989).
Roser Bruce et al "A sweeter way to fresher food" New Scientist p. 25 (1993).
Roser Bruce "Trehalose Drying: A Novel Replacement for Freeze-Drying" BioPharm 4:47-53 (1991).
Roser Bruce "Trehalose, a new approach to premium dried foods" Trends Food Sci Technol p. 186 (1991).
Royall Paul G et al "Characterisation of moisture uptake effects on the glass transitional behaviour of an amorphous drug using modulated temperature DSC" Intl J Pharm 192:39-46 (1999).
Sacchetti Mark et al "Spray-Drying and Supercritical Fluid Particle Generation Techniques" Inhalation Aerosols. Physical and Biological Basis for Therapy, Anthony J Hickey ed, Marcel Dekker pub, Ch 11 p. 337 (1997).
Saleki-Gerhardt Azita et al "Hydration and Dehydration of Crystalline and Amorphous Forms of Rattinose" J Pharm Sci 84(3):318 (1995).
Saleki-Gerhardt Azita et al "Non-Isothermal and Isothermal Crystallization of Sucrose from the Amorphous State" Pharm Res 11(8):1166 (1994).
Sambrook et al "Concentrating Nucleic Acids, Precipitation with Ethanol or Isopropanol" Molecular Cloning: A Laboratory Manual, 2$^{nd}$ ed, Cold Spring Harbor Lab Press p. E.10-E.17 (1969).
Sanchez J et al "Recombinant system for overexpression of cholera toxin B subunit in *Vibrio cholerae* as a basis for vaccine development" Proc Natl Acad Sci USA 86:481-485 (1989).
Sarkar Nurul et al "Immunization of Mice against Murine Mammary Tumor Virus Infection and Mammary Tumor Development" Cancer Res 36:1468-1472 (1978).
Sasaki S et al "Human Immunodeficiency virus type-1-specific immune responses induced by DNA vaccination are greatly enhanced by mannan-coated dlC14-amidine" Eur J Immunol 27(12):3121-9 (1997) Abstract.
Satoh Koichi "Determination of binding constants of $Ca^{2+}$, $Na^+$, $Cl^-$Ions to liposomal membranes of dipalmitoylphosphatidylcholine at gel phase by particle electrophoresis" Biochim Biophys Acta 1239:239-248 (1995).

(56) References Cited

OTHER PUBLICATIONS

Schebor Carolina et al "Color formation due to non-ezymatic browning in amorphous, glassy, anhydrous, model systems" Food Chem 65:427-432 (1999).
Schramm Laurie L, The Language of Colloid and Interface Science. A Dictionary of Terms, ACS Professional Reference Book p. 157 (1993).
Schröder Kendra et al "Influence of Bulk and Tapped Density of the Determination of the Thermal Conductivity of Powders and Blends" AAPS PharmSciTech 8(3):E1 Article 78 (2007).
Sciarra John J et al "Aerosols" Remington's Pharmaceutical Sciences, $17^{th}$ ed, Mack pub, Alfonso R Gennaro ed, Ch 93 p. 1662 (1985).
Sebhatu Tesfai et al "Assessment of the degree of disorder in crystalline solids by isothermal microcalorimetry" Intl J Pharm 104:135-144 (1994).
Seddon John M "Structure of the inverted hexagonal ($H_2$) phase, and non-lamellar phase transitions of lipids" Biochim Biophys Acta 1031:1-69, in particular p. 43-44 and p. 49-50 (1990).
Seelig Joachim "Metal Ion Interactions with Lipids" Handbook Met-Ligand Interact Biol Fluids:Bioinorg Chem, Pt 3, Ch 2, Sec F, p. 698-706 (1995).
Sellers Scott P et al "Dry Powders of Stable Protein Formulations from Aqueous Solutions Prepared Using Supercritical $CO_2$-Assisted Aerosolization" J Pharm Sci 90(6):785 (2001).
Serajuddin TM et al "Effect of thermal history on the glassy state of indapamide" J Pharm Pharmacol 38:219-220 (1986).
Shah DO et al "The ionic structure of sphingomyelin monolayers" Biochim Biophys Acta 135:164-167 (1957).
Shalaev Evgenyi Yu et al "Structural Glass Transitions and Thermophysical Processes in Amorphous Carbohydrates and their Supersaturated Solutions" J Chem Soc Faraday Trans 91(10):1511-1517 (1995).
Shalaev Evgenyi Yu et al "How Does Residual Water Affect the Solid-State Degradation of Drugs in the Amorphous State?" J Pharm Sci 85(11):1137 (1996).
Shamblin Sheri L et al "Enthalpy Relaxation in Binary Amorphous Mixtures Containing Sucrose" Pharm Res 15(12):1826 (1998).
Sharma Vikas K et al "Effect of Vacuum Drying on Protein-Mannitol Interactions: The Physical State of Mannitol and Protein Structure in the Dried State" AAPS PharmSciTech 5(1) Article 10:1-12 [on-line] [retrieved] Retrieved from the Internet <URL: http:www.aapspharmscitech.org >, 2004.
Shavnin Sergei A et al "Cholesterol effects divalent cation-induced fusion and isothermal phase transitions of phospholipid membranes" Biochim Biophys Acta 946:405-416 (1988).
Shibata Y et al "Chitin particle-induced cell-mediated immunity is inhibited by soluble mannan: mannose receptor-mediated phagocytosis initiates IL-12 production" J Immunol 159(5):2462-2467 (1997).
Simha Robert et al "On a General Relation Involving the Glass Temperature and Coefficients of Expansion of Polymers" J Chem Physics 37(5):1003-1007 (1962).
Singer Mike A et al "Thermotolerance in *Saccharomyces ceravisiae*: the Yin and Yang of trehalose" TibTech 16:460 (1996).
Skrabanja Arno TP et al "Lyophilization of Biotechnology Products" PDA J Phy Sci Technol 48(6):311 (1994).
Slade Louise et al "Non-equillibrium behavior of small carbohydrate-water systems" Pure Appl Chem 80(12):1841-1864 (1988).
Slade Louise et al "The Glassy State Phenomenon in Food Molecules" The Glassy State in Foods, Nottingham Univ Press, Ch 3 p. 35 (1993).
Sokolov AP et al "Glassy dynamics in DNA: Ruled by water of hydration?" J Chem Physics 110(14):7053 (1999).
Sola-Penna Mauro et al "Stabilization against Thermal Inactivation Promoted by Sugars on Enzyme Structure and Function: Why is Trehalose More Effective than Other Sugars?" Arch Biochem Biophys 360(1)10-14 (1998).

Sonner Christine et al "Spray-Freeze-Drying for Protein Powder Preparation: Particle Characterization and a Case Study with Trypsinogen Stability" J Pharm Sci 91(10):2122 (2002).
SPI Polyols "What are Polyols? What do Polyols do? What are Polyols' functionality?" [on-line] [retrieved Jun. 25, 2004] Retrieved from the Internet <URL: http://www.spipolyols.com/whatarepolyols.html> 1p (2003).
Stribling Roscoe et al "Aerosol gene delivery in vivo" Proc Natl Acad Sci USA 89:11277-11281 (1992).
Strickley Robert G et al "Solid-State Stability of Human Insulin II. Effect of Water on Reactive Intermediate Partitioning in Lyophiles from pH 2-5 Solutions: Stabilization against Covalent Dimer Formation" J Pharm Sci 86(6):645 (1997).
Strøm AR et al "Trehalose metabolism in *Escherichia coli*: stress protection and stress regulation of gene expression" Mol Microbiol 8(2):205-210 (1993).
Stubberud Lars et al "The use of gravimetry for the study of the effect of additives on the moisture-induced recrystallisation of amorphous lactose" Intl J Pharm 163:145-156 (1998).
Sugisaki Masayasu et al "Calorimetric Study of the Glassy State. IV. Heat Capacities of Glassy Water and Cubic Ice" Bull Chem Soc Jpn 41:2591-2599 (1968).
Sukenik Chaim N et al "Enhancement of a Chemical Reaction Rate by Proper Orientation of Reacting Molecules in the Solid State" J Amn Chem Soc 97(18):5290 (1975).
Sussich Fabiana et al "Reversible dehydration of trehalose and anhydrobiosis: from solution state of an exotic crystal?" Carbohy Res 334:165-176 (2001).
Takahashi Hidemi et al "Induction of $CD8^+$ cytotoxic T cells by immunization with purified HIV-1 envelope protein in ISCOMs" Nature 344:673 (1990).
Tarara Thomas E et al "Characterization of Suspension-Based Metered Dose Inhaler Formulations Composed of Spray-Dried Budesonide Microcrystals Dispersed in HFA-134a" Pharm Res 21(9):1607 (2004).
Tarelli E et al "Additives to biological substances. III. The moisture content and moisture uptake of commonly used carrier agents undergoing processing conditions similar to those used in the preparation of international biological standards" J Biol Standardization 15:331-340 (1987).
Tatulian Suren A "Binding of alkaline-earth metal cations and some anions to phosphatidylcholine liposomes" Eur J Biochem 170:413-420 (1967).
Tatulian Suren A "Evaluation of Divalent Cation Binding to Phosphatidylserine Membranes by an Analysis of Concentration Dependence of Surface Potential" J Colloid Interface Sci 75:131-137 (1995).
Thatcher E "Virology, Quantitation of Virus" [on-line] [retrieved Sep. 23, 2010] Retrieved from the Internet <URL http://www.sonoma.edu/users/t/thatcher/biol383/lab.htm> 4p, last updated Jan 5, 2002.
Timko Robert J et al "Thermal Analysis Studies of Glass Dispersion Systems" Drug Dev Ind Pharm 10(3):425-451 (1984).
Timsina MP et al "Drug delivery to the respiratory tract using dry powder inhalers" Intl J Pharm 101:1-13 (1994).
To Eddie C et al "'Collapse', a structural transition in freeze dried carbohydrates, II. Effect of solute composition" J Fd Technol 13:567-581 (1978).
Handbook of Natural Products for Food Processing, $9^{th}$ ed, A Toyama ed, Osaka, Japan, p. 384, p. 495 (1986).
Tsourourlis Spyros et al "Loss of Structure in Freeze-dried Carbohydrates Solutions: Effect of Temperature, Moisture Content and Composition" J Sci Fd Agric 27;509-519 (1976).
Ulrich Anne S "Biophysical Aspects of Using Liposomes as Delivery Vehicles. Liposome Composition and Size" Biosci Rep 22(2):129 (2002).
Underwood Stephen L et al "A Novel Technique for the Administration of Bronchodliator Drugs Formulated as Dry Powders to the Anaesthetized Guinea Pig" J Pharmacol Methods 26:203-210 (1991).
Uritani Masslito et al "Protective Effect of Disaccharides on Restriction Endonucleases during Drying under Vacuum" J Biochem 117:774-779 (1995).

(56) References Cited

OTHER PUBLICATIONS

Vain Philippe et al "Development of the Particle Inflow Gun" Plant Cell Tissue Organ Cult 33:237-246 (1993).
Vavelyuk OL et al "Thermostability of DNA and its Association with Vitrification" Tsitologiya 41(11):958-965 (1999).
Verstraeten Sandra V et al "Effects of $Al^{3+}$ and Related Metals on Membrane Phase State and Hydration: Correlation with Lipid oxidation" Arch Biochem Biphys 375(2)340-346 (2000).
VidgréMT et al "Comparison of physical and inhalation properties of spray-dried and mechanically micronized disodium cromoglycate" Int J Pharm 35:139-144 (1987).
Vromans H et al "Studies on tableting properties of lactose. VII. The effects of variations in primary particle size and percentage of amorphous lactose in spray dried lactose products" Int J Pharm 35:29-37 (1987).
Stability and Characterization of Protein and Peptide Drugs, Case Histories, Y. John Wang et al ed, Plenum Press, Table of Contents 6p (1993).
Weers Jeffry G "Colloidal particles in drug delivery" Curr Opin Colloid Interface Sci 3:540-544 (1996).
Welsh David T "The Role of Compatible Solutes in the Adaptation and Survival of *Escherichia coli*", Thesis submitted to Dept of Biological Sciences, Univ of Dundee, Aug. 1992, p. 1-262.
Whipps Scott et al "Growth of calcium oxalate monohydrate at phospholipid Langmuir monolayers" J Cryst Growth 192:243-249 (1998).
Whittier Earle O "Lactose and its Utilization: A Review" J Dairy Sci XXVII(7):505 (1944).
Williams Malcolm L. et al "The Temperature Dependence of Relaxation Mechanisms in Amorphous Polymers and Other Glass-forming Liquids" J Amn Chem Soc 77:3701 (1955).
Williams Robert J et al "The Glassy State in Corn Embryos" Plant Physiol 89:977-981 (1969).
Wolff Jon A et al "Grafting fibroblasts genetically modified to produce L-dopa in a rat model of Parkinson disease" Proc Natl Acad Sci USA 86:9011-9014 (1989).
Xi You Geng et al: Amphotericin B treatment dissociates in vivo replication of the scraple agent from PrP accumulation Nature 356:598 (1992).
Yamaguchi Tetsuo et al "Adsorptionof divalent cations onto the membrane surface of lipid emulsion" Colloids Surf B 5:49-55 (1995).
York Peter "Powdered Raw Materials: Characterizing Batch Uniformity" Resp Drug Del IV, p. 63 (1994).
Yoshida H "Absorption of Insulin Delivered to Rabbit Trachea Using Aerosol Dosage Form" J Pharm Sci 68(5):670 (1979).
Yoshinari Tomohiro et al "Moisture induced polymorphic transition of mannitol and its morphological transformation" Intl J Pharm 247:69-77 (2002).
Yoshioka Minoru et al "Crystallization of Indomethacin from the Amorphous State below and above its Glass Transition Temperature" J Pharm Sci 83(12):1700 (1994).
Zubay Geoffrey "Structure of the Peptide Bond" Biochemistry, $2^{nd}$ ed, Macmillan Pub, Ch 1, Box 1-A, p. 39 (1988).
Zubay Geoffrey "Major Steroid Hormones" Biochemistry, $2^{nd}$ ed, Macmillan Pub, Ch 5, table 5-6, p. 169 (1988).
Office Action in U.S. Appl. No. 09/218,209 (patented as U.S. Pat. No. 6,433,040) dated May 26, 1999.
Office Action in U.S. Appl. No. 09/218,209 (patented as U.S. Pat. No. 6,433,040) dated Feb 15, 2000.
Office Action in U.S. Appl. No. 09/218,209 (patented as U.S. Pat. No. 6,433,040) dated Jan. 29, 2001.
Office Action in U.S. Appl. No. 09/218,212 (patented as U.S. Pat. No. 6,309,623) dated May 17, 1999.
Office Action in U.S. Appl. No. 09/218,212 (patented as U.S. Pat. No. 6,309,623) dated Jul. 28, 2000.
Office Action in U.S. Appl. No. 09/218,212 (patented as U.S. Pat. No. 6,309,623) dated Dec. 20, 2000.
Office Action in U.S. Appl. No. 09/218,213 (patented as U.S. Pat. No. 6,946,117) dated Jun. 29, 1999.
Office Action in U.S. Appl. No. 09/218,213 (patented as U.S. Pat. No. 6,946,117) dated Apr. 28, 2000.
Office Action in U.S. Appl. No. 09/218,213 (patented as U.S. Pat. No. 6,946,117) dated Nov. 16, 2000.
Office Action in U.S. Appl. No. 09/218,213 (patented as U.S. Pat. No. 6,946,117) dated May 19, 2004.
Office Action in U.S. Appl. No. 09/219,736 (patented as U.S. Pat. No. 6,565,885) dated Jun. 29, 1999.
Office Action in U.S. Appl. No. 09/219,736 (patented as U.S. Pat. No. 6,565,885) dated Dec. 20, 2000.
Office Action in U.S. Appl. No. 09/219,736 (patented as U.S. Pat. No. 6,565,885) dated Aug. 29, 2001.
Office Action in U.S. Appl. No. 09/566,818 dated Apr. 10, 2002.
Office Action in U.S. Appl. No. 09/566,818 dated Nov. 5, 2002.
Office Action in U.S. Appl. No. 09/566,818 dated Jul. 29, 2003.
Office Action in U.S. Appl. No. 09/566,818 dated May 5, 2004.
Office Action in U.S. Appl. No. 09/566,818 dated Apr. 7, 2005.
Office Action in U.S. Appl. No. 09/566,818 dated Jan. 24, 2006.
Office Action in U.S. Appl. No. 09/566,818 dated Oct. 6, 2006.
Office Action in U.S. Appl. No. 09/566,818 dated Jun. 4, 2007.
Office Action in U.S. Appl. No. 09/566,818 dated Feb. 26, 2008.
Office Action in U.S. Appl. No. 09/566,818 dated Dec. 8, 2008.
Office Action in U.S. Appl. No. 09/720,536 (patented as U.S. Pat. No. 6,630,169) dated Jul. 15, 2002.
Office Action in U.S. Appl. No. 09/851,226 (patented as U.S. Pat. No. 7,442,388) dated Feb. 11, 2003.
Office Action in U.S. Appl. No. 09/851,226 (patented as U.S. Pat. No. 7,442,388) dated Jul. 24, 2003.
Office Action in U.S. Appl. No. 09/851,226 (patented as U.S. Pat. No. 7,442,388) dated May 5, 2004.
Office Action in U.S. Appl. No. 09/851,226 (patented as U.S. Pat. No. 7,442,388) dated Jun. 24, 2002.
Office Action in U.S. Appl. No. 09/851,226 (patented as U.S. Pat. No. 7,442,388) dated Mar. 22, 2005.
Office Action in U.S. Appl. No. 09/851,226 (patented as U.S. Pat. No. 7,442,388) dated Dec. 21, 2005.
Office Action in U.S. Appl. No. 09/862,764 (patented as U.S. Pat. No. 6,638,495) dated Nov. 1, 2002.
Office Action in U.S. Appl. No. 09/886,296 dated Jun. 19, 2002.
Office Action in U.S. Appl. No. 09/886,296 dated Dec. 11, 2002.
Office Action in U.S. Appl. No. 09/886,296 dated Jul. 21, 2003.
Office Action in U.S. Appl. No. 09/886,296 dated Apr. 16, 2004.
Office Action in U.S. Appl. No. 09/886,296 dated Nov. 2, 2005.
Office Action in U.S. Appl. No. 09/886,296 dated Jun. 6, 2006.
Office Action in U.S. Appl. No. 09/886,296 dated Mar. 28, 2007.
Office Action in U.S. Appl. No. 09/886,296 dated Nov. 9, 2007.
Office Action in U.S. Appl. No. 09/886,296 dated Apr. 22, 2008.
Office Action in U.S. Appl. No. 09/886,296 dated Dec. 5, 2006.
Office Action in U.S. Appl. No. 09/886,296 dated Jun. 22, 2009.
Office Action in U.S. Appl. No. 09/888,311 dated Dec. 5, 2001.
Office Action in U.S. Appl. No. 09/888,311 dated Jun. 25, 2002.
Office Action in U.S. Appl. No. 09/888,311 dated Jan. 8, 2003.
Office Action in U.S. Appl. No. 09/999,071 (patented as U.S. Pat. No. 7,205,343) dated Jun. 17, 2003.
Office Action in U.S. Appl. No. 09/999,071 (patented as U.S. Pat. No. 7,205,343) dated Jan. 23, 2004.
Office Action in U.S. Appl. No. 09/999,071 (patented as U.S. Pat. No. 7,205,343) dated Oct. 7, 2004.
Office Action in U.S. Appl. No. 09/999,071 (patented as U.S. Pat. No. 7,205,343) dated Jun. 12, 2005.
Office Action in U.S. Appl. No. 09/999,071 (patented as U.S. Pat. No. 7,205,343) dated Jan. 18, 2006.
Office Action in U.S. Appl. No. 10/096,780 (patented as U.S. Pat. No. 7,306,787) dated Oct. 2, 2002.
Office Action in U.S. Appl. No. 10/096,780 (patented as U.S. Pat. No. 7,306,787) dated May 20, 2003.
Office Action in U.S. Appl. No. 10/096,780 (patented as U.S. Pat. No. 7,306,787) dated Jun. 17, 2004.
Office Action in U.S. Appl. No. 10/096,780 (patented as U.S. Pat. No. 7,306,787) dated Apr. 19, 2005.
Office Action in U.S. Appl. No. 10/096,780 (patented as U.S. Pat. No. 7,306,787) dated Jan. 25, 2006.
Office Action in U.S. Appl. No. 10/141,032 dated Oct. 23, 2002.

(56) References Cited

OTHER PUBLICATIONS

Office Action in U.S. Appl. No. 10/141,032 dated Jul. 16, 2003.
Office Action in U.S. Appl. No. 10/141,032 dated Aug. 17, 2004.
Office Action in U.S. Appl. No. 10/141,032 dated May 20, 2005.
Office Action in U.S. Appl. No. 10/141,219 dated Oct. 23, 2003.
Office Action in U.S. Appl. No. 10/141,219 dated Nov. 15, 2004.
Office Action in U.S. Appl. No. 10/141,219 dated Jun. 6, 2005.
Office Action in U.S. Appl. No. 10/141,219 dated Mar. 10, 2006.
Office Action in U.S. Appl. No. 10/141,219 dated Nov. 29, 2006.
Office Action in U.S. Appl. No. 10/141,219 dated Jul. 21, 2008.
Office Action in U.S. Appl. No. 10/141,219 dated Jan. 8, 2009.
Office Action in U.S. Appl. No. 10/141,219 dated Aug. 18, 2009.
Office Action in U.S. Appl. No. 10/141,219 dated Mar. 26, 2010.
Office Action in U.S. Appl. No. 10/612,393 dated May 4, 2005.
Office Action in U.S. Appl. No. 10/612,393 dated Aug. 10, 2005.
Office Action in U.S. Appl. No. 10/612,393 dated Feb. 9, 2006.
Office Action in U.S. Appl. No. 10/612,393 dated Aug. 1, 2006.
Office Action in U.S. Appl. No. 10/616,448 dated Oct. 25, 2004.
Office Action in U.S. Appl. No. 10/616,448 dated Aug. 19, 2005.
Office Action in U.S. Appl. No. 10/616,448 dated May 4, 2006.
Office Action in U.S. Appl. No. 10/616,448 dated Apr. 16, 2008.
Office Action in U.S. Appl. No. 10/616,448 dated Nov. 14, 2008.
Office Action in U.S. Appl. No. 10/616,448 dated Sep. 25, 2009.
Office Action in U.S. Appl. No. 10/616,448 dated Feb. 25, 2010.
Office Action in U.S. Appl. No. 10/616,448 dated Jul. 14, 2010.
Office Action in U.S. Appl. No. 10/644,265 (patented as U.S. Pat. No. 7,628,978) dated Oct. 7, 2005.
Office Action in U.S. Appl. No. 10/644,265 (patented as U.S. Pat. No. 7,628,978) dated May 9, 2006.
Office Action in U.S. Appl. No. 10/644,265 (patented as U.S. Pat. No. 7,628,978) dated Feb. 1, 2007.
Office Action in U.S. Appl. No. 10/644,265 (patented as U.S. Pat. No. 7,628,978) dated Mar. 20, 2008.
Office Action in U.S. Appl. No. 11/076,430 dated Nov. 13, 2006.
Office Action in U.S. Appl. No. 11/076,430 dated May 11, 2009.
Office Action in U.S. Appl. No. 11/076,430 dated Mar. 3, 2010.
Office Action in U.S. Appl. No. 11/187,757 dated Mar. 26, 2010.
Office Action in U.S. Appl. No. 11/187,757 dated Oct. 13, 2010.
Office Action in U.S. Appl. No. 11/317,523 dated Sep. 25, 2008.
Office Action in U.S. Appl. No. 11/317,523 dated Apr. 10, 2009.
Office Action in U.S. Appl. No. 11/317,523 dated Oct. 1, 2009.
Office Action in U.S. Appl. No. 11/317,523 dated May 25, 2010.
Office Action in U.S. Appl. No. 11/317,839 dated Sep. 25, 2008.
Office Action in U.S. Appl. No. 11/317,839 dated Apr. 13, 2009.
Office Action in U.S. Appl. No. 11/317,839 dated Dec. 23, 2009.
Office Action in U.S. Appl. No. 11/317,839 dated Aug. 17, 2010.
Office Action in U.S. Appl. No. 10/675,073 (patented as U.S. Pat. No. 7,393,544) dated Sep. 17, 2007.
Office Action in U.S. Appl. No. 12/012,827 (patented as U.S. Pat. No. 7,790,145) dated Oct. 21, 2009.
Cicogna Cristina E et al "Efficacy of Prophylactic Aerosol Amphotericin B Lipid Complex in a Rat Model of Pulmonary Aspergillosis" Antimicrob Agents Chemother 41(2):259-261 (1997).
"Powder-Delivery Systems" Encyclopedia of Pharmaceutical Technology, James Swarbrick et al ed, Marcel Dekker pub, vol. 9 p. 288 ((1994).
English translation of FR 2667072 (Mar. 27, 1992).
English translation of JP 02084401 (Mar. 28, 1990).
English translation of JP H3-264537 (Nov. 25, 1991).
Opposition Papers of European Patent No. EP 1019021 (Application No. 98950826.2) Dated Jun. 3, 2004 through Sep. 9, 2006.
Nektar Notice of Opposition to European Patent No. EP 0939622 (Application No. 97909449.7) dated Dec. 5, 2003.
Roitt et al "Autoimmune diseases. 2—Pathogenesis, diagnosis and treatment" Roitt's Essential Immunology, 10$^{th}$ ed, Blackwell Science, Ch 20, p. 442, p. 449 (2001).
Zubay Geoffrey "Structural Properties of DNA" Biochemistry, 2$^{nd}$ ed, Macmillian Pub, Pt 1, p. 216 (1988).

Office Action in U.S. Appl. No. 08/422,563 (patented as U.S. Pat. No. 5,994,314) dated Apr. 3, 1998.
Nektar U.S. Appl. No. 08/044,358, filed Apr. 7, 1993.
Dellamary et al. Pharmaceutical Research, Feb. 2000, vol. 17, No. 2, pp. 168-174.
U.S. Appl. No. 60/059,004, filed Sep. 15, 1997, Vanbever.
U.S. Appl. No. 60/060,337, filed Sep. 29, 1997, Kalbanov.
Advertisement for Stop 'n Grow Mfr: The Mentolatum Co Ltd, East Kilbride, Scotland.
Adjei Akwete et al "Pulmonary Delivery of Peptide Drugs: Effect of Particle Size on Bioavailability of Leuprolide Acetate in Healthy Male Volunteers" Pharm Res 7(6):565 (1990).
Agrimi U et al "Amyloid, Amyloid-inducers Cytokines and Heavy Metals in Scrapie and Other Human and Animal Subacute Spongiform Encephalopathies: Some Hypotheses" Med Hypotheses 40:113-116 (1993).
Ahlneck Claes et al "The molecular basis of moisture effects on the physical and chemical stability of drugs in the solid state" Intl J Pharm 62:87-95 (1990).
Akers Michael J et al "Glycine Crystallization During Freezing: The Effects of Salt Form, pH, and Ionic Strength" Pharm Res 12(10):1457 (1995).
Akoh Casimir C et al "One-Stage Synthesis of Raffinose Fatty Acids Polyesters" J Food Sci 52(6):1570 (1987).
Alberts B et al "Small Molecules, Energy, and Biosyntheses" Molecular Biology of the Cell, 2$^{nd}$ ed, Garland Pub, Ch 2 p.58 (1989).
"Albuterol" Merck Index, 12$^{th}$ ed, Susan Budeveri ed, monograph 217, p. 40 (1998).
Aldous Barry J et al "The Crystallisation of Hydrates from Amorphous Carbohydrates" Cyro-Letters 16:181-186 (1995).
Allen DJ et al "Determination of the Degree of Crystallinity in Solid-Solid Equilibria" J Pharm Sci 58(10):1190 (1969).
Allison S Dean et al "Mechanisms of Protection of Cationic Lipid—DNA Complexes During Lyophilization" J Pharm Sci 89(5):682 (2000).
Allison S Dean et al "Lyophilization of Nonviral Gene Delivery Systems" Methods In Molecular Med, Mark A Findeis ed, Humana Press, vol. 65: Nonviral Vectors for Gene Therapy, Ch 18 p. 225 (2001).
Altenbach Christian et al "$Ca^{2+}$ Binding to Phosphatidylcholine Bilayers as Studied by Deuterium Magnetic Resonance. Evidence for the Formation of a $Ca^{2+}$ Complex with Two Phospholipid Molecules" Biochem 23:3913-3920 (1984).
Amidon Gregory E et al "Powder Flow Testing in Preformulation and Formulation Development" Pharm Mfg 2:22 (1985).
"Amphotericin B" Merck Index, 12$^{th}$ ed, Susan Budavari et al ed, monograph 627, p. 99 (1996).
Anchordoquy Thomas J et al "Physical stabilization of DNA-based therapeutics" Drug Discovery Today 6(9):463 (2001).
Andronis Viassios et al "The Molecular Mobility of Supercooled Amorphous Indomethacin as a Function of Temperature and Relative Humidity" Pharm Res 15(6):835 (1998).
Anekwe Jerome U et al "Relaxation Constants as a Predictor of Protein Stabilization" Biocalorimetry: Applications of Calorimetry in the Biological Sciences, John E Ladbury ed, John Wiley & Sons Ltd, Ch 17 p. 243 (1998).
Babincová M et al "Dextran Enhances Calcium-Induced Aggregation of Phosphatidylserine Liposomes: Possible Implications for Exocytosis" Physiol Res 48:319-321 (1999).
"Drug Absorption and Availability. Solid-Solid interactions" Modern Pharmaceutics, 3$^{rd}$ ed, Gilbert S. Banker ed, Marcel Dekker, NY p. 145 (1996).
Bandara G et al "Intraarticular expression of biologically active interleukin 1-receptor-antagonist protein by ex vivo gene transfer" Proc Natl Acad Sci USA 90:10764-10768 (1993).
Barnett AH "Exubera Inhaled Insulin: a review" Intl J Clin Pract 58(4):394-401 (2004).
Bell JH et al "Dry Powder Aerosols I: A New Powder Inhalation Device" J Pharm Sci 60(10):1559 (1971).

(56) References Cited

OTHER PUBLICATIONS

Belopolskaya TV et al "The Effect of Water as a Natural Plasticizer on Thermal Properties of Denaturated DNA Studied by Calorimetry" 4 Vestnik Sankt-Petersburgskogo Universiteta Seriya 2(11):16 (1999).
Bigsbee Dabiel B et al "Solid State Stability of Insulin: Comparison of Crystalline and Amorphous Forms" Pharm Res 10(10):S-279, Abstract PDD 7418 (1993).
Blakeley Diane et al "Dry Instant blood typing plate for bedside use" Lancet 336:854 (1990).
Block LH et al "Solubility and Dissolution of Triamcinolone Acetonide" J Pharm Sci 62(4):617 (1973).
Bögelein J et al "Influence of Amorphous Mannitol on Powder Properties of Spray Dried Trehalose/Dextran Mixtures" [on-line] [retrieved Sep. 2005] Retrieved from the Internet <URL:http://www.pharmatech.unierlangen.de/APV_03/bogelein.pdf> 2p (2003).
Bootsma HPR et al "β-Cyclodextrin as an excipient in solid oral dosage forms: In vitro and in vivo evaluation of spray-dried diazepam-β-cyclodextrin products" Intl J Pham 51:213-223 (1989).
Borgström L et al "Lung deposition of budesonide inhaled via Turbuhaler®:a comparison with terbutaline sulphate in normal subjects" Eur Respir J 7:69-73 (1994).
Bosquillon Cynthia et al "Aersolization properties, surface composition and physical state of spray-dried protein powders" J Controlled Release 99:357-367 (2004).
Branca C et al "Destructuring effect of trehalose on the tetrahedral network of water: a Raman and neutron diffraction comparison" Physica A 304:314-318 (2002).
Branchu Sébastien et al "The Effect of Cyclodextrins on Monomeric Protein Unfolding" Biocalorimetry: Applications of Calorimetry in the Biological Sciences, John E Ladbury ed, John Wiley & Sons Ltd, ch 22 p. 297-301 (1998).
Branchu Sébastien et al "Hydroxypropyl β-cyclodextrin Inhibits Spray-Drying Induced Activation of β-Galactosidase" J Pharm Sci 88(9):905 (1999).
Brange Jens et al "Chemical Stability of Insulin. 1. Hydrolytic Degaradation During Storage of Pharmaceutical Preparations" Pharm Res 9(6):715 (1992).
Breitenbach Jörg "Melt extrusion: from process to drug delivery technology" Eur J Pharm Biopharm 54:107-117 (2002).
Broadhead J et al "The Effect of Process and Formulation Variables on the Properties of Spray-dried β-Galactosidase" J Pharm Pharmacol 48:456-467 (1994).
Broadhead J et al "The Spray Drying of Pharmaceuticals" Drug Del Ind Pharm 18 (11&12):1169-1206 (1992).
Brown P "A therapeutic panorama of the spongiform encephalopathies" Antiviral Chem Chemother 1(2):75-83 (1990).
Buckton Graham et al "The use of gravimetric studies to assess the degree of crystallinity of predominantly crystalline powders" Intl J Pharma 123:265-271 (1995).
Buitink Julia et al "High Critical Temperature above $T_6$ May Contribute to the Stability of Biological Systems" Biophys J 79:1119-1126 (2000).
Büldt G et al "Neutron Diffraction Studies on Phosphatidylcholine Model Membranes" J Mol Biol 134:673-691 (1979).
Burvall Anders et al "Storage of lactose-hydrolysed dried milk: effect of water activity on the protein nutritional value" J Dairy Res 45:381-389 (1978).
Bustami Rene T et al "Generation of Micro-Particles of Proteins for Aerosol Delivery Using High Pressure Modified Carbon Dioxide" Pharm Res 17(11):1360 (2000).
Byron Peter R et al "Drug Carrier Selection—Important Physiochemical Characteristics" Respiratory Drug Delivery V, 5th ed, Interpharm Press, p. 103 (1996).
Byström Katarina "Microcalorimetry—A Novel Technique for Characterization of Powders" Respiratory Drug Deilvery IV, p. 297 (1994).
Carpenter John F et al "Rational Design of Stable Lyophilized Protein Formulations: Some Practical Advice" Pharm Res 14(8):969 (1997).
Casselyn M et al "Time-resolved scattering inveatigations of brome mosaic virus microcrystals appearance" Acta Cryst D58:1568-1570 (2002).
Caughey Byron et al "Sulfated Polyanion Inhibition of Scrapie-Associated PrP Accumulation in Cultured Cells" J Virol 67(2):643-650 (1993).
Cevc Gregor "Membrane electronics" Biochem Biophys Acta 1031-3:311-362 (1990), in particular p. 330-338.
Chan Tai Wah et al "Formulation of Vaccine Adjuvant Muramyldipeptides (MDP). 1. Characterization of Amorphous and Crystalline Forms of a Muramyldipeptide Analogue" Pharm Res 5(8):523 (1988).
Chan Hak-Kim et al "Solid State Characterization of Spray-Dried Powders of Recombinant Human Deoxyribonuclease (RhDNase)" J Pharm Sci 87(5):647 (1998).
Chan Hak-Kim et al "Physical Stability of Salmon Calcitonin Spray-Dried Powders for Inhalation" J Pharm Sci 93(3):792 (2004).
Chavan Varsha et al "Effect of Rise In Simulated Inspiratory Flow Rate and Carrier Particle Size on Powder Emptying from Dry Powder Inhalers" AAPS PharmSci 2(2) Article 10 [on-line] Retrieved from the Internet <URL: http://www.pharmsl.org> 7 pg (2000).
Chavan Varsha et al "Novel System to Investigate the Effects of Inhaled Volume and Rates of Rise in Simulated Inspiratory Air Flow on Fine Particle Output from a Dry Powder Inhaler" AAPS PharmSci 4(2) Article 6 [on-line] Retrieved from the Internet <URL: http://www.pharmsci.org> 6 pg (2002).
Chavan VS et al "Effect of Particle Size and Rise in Simulated Inspiratory Flow Rate on Device Emptying in a Dry Powder Inhaler System" [on-line] [retrieved Jan. 7, 2005] Retrieved from the Internet <URL: http://www.aapspharmsci.org/abstracts/AM_1999/1001.htm> 1 pg (1999).
Chawla A et al "Production of spray dried salbutemol sulphate for use in dry powder aerosol formulation" Intl J Pharm 108:233-240 (1994).
Chou Win Loung et al "Pharmaceutical Applications of Solid Dispersion Systems" J Pharm Sci 80(9):1281 (1971).
Christensen KL et al "Preparation of redispersible dry emulsions by spray drying" Intl J Pharm 212:187-194 (2001).
Cleland Jeffrey L et al "The Development of Stable Protein Formulations: A Close Look at Protein Aggregation, Deamidation, and Oxidation" Crit Rev Ther Drug Carrier Sys 10(4):307-377 (1993).
Cline David et al "Predicting the Quality of Powders for Inhalation from Surface Energy and Area" Pharm Res 19(9):1274 (2002).
Cline David et al "Predicting the Quality of Powders for Inhalation" Resp Drug Delivery VIII, p. 683. (2002).
"Coacervate" Wikipedia, 2p (2007).
Colaco Camilo et al Extraondinary Stability of Enzymes Dried in Trehalose: Simplified Molecular Biology Bio/Technol 10():1007-1011 (1992).
Colaco Cals et al "Trehelose Stabilisation of Biological Molecules" Biotechnol Intl p. 345 (1992).
Colaco Cals et al "Chemistry of Protein Stabilization by Trehalose" Amn Chem Soc Symposium Series 567—Formulation of Delivery of Proteins and Peptides, 205th National Meeting, Denver, CO Mar. 28-Apr. 2, 1993, Ch 14 p. 222 (1994).
Considine GD et al, Van Nostrand's Scientific Encyclopedia 9th ed, Wiley-Interscience, John Wiley & Sons Inc, Definition of Vaccines, p. 3591-3592 (2002).
Costantino Henry R et al "Moisture-Induced Aggregation of Lyophilized Insulin" Pharm Res 11(1):21 (1994).
Costantino Henry R et al "Effect of Mannitol Crystallization on the Stability and Aerosol Performance of a Spray-Dried Pharmaceutical Protein, Recombinant Humanized Anti-IgE Monoclonal Antibody" J Pharm Sci 67(11)1406 (1998).
Craig Iain D et al "Maillard Reaction Kinetics in Model Preservation Systems in the Vicinity of the Glass Transition: Experiment and Theory" J Agric Food Chem 49:4706-4712 (2001).

(56) References Cited

OTHER PUBLICATIONS

Crommelin Dean JA et al "Liposomes" Drugs and the Pharmaceutical Analyse—Collioidai Drug Delivery Systems, Jörg Kreuter ed, No. 66 Ch 3 p. 73 (1994).
Crowe John H et al "The Role of Vitrification in Anhydrobiosis" Annu Rev Physiol 90:73-103 (1998).
Crowe John H et al "Interactions of sugars with membranes" Biochim Biophys Acta 947:367-384 (1988).
Crowe John H et al "Are Freezing and Dehydration Similar Stress Vectors? A Comparision of Modes of Interaction of Stabilizing Solutes with Biomolecules" Cryobiology 27:219-231 (1990).
Crowe Lois M et al "Is Trehalose Special for Preserving Dry Biomaterials?" Blophys J 71:2087-2093 (1996).
D'Cruz N et al "Relationship between protein thermal stability and glass transition in gelatin-polyol and gelatin-water mixtures" Proceedings of 2004 Meeting ITF, Jul. 12-16, 2004, Las Vegas, NV, Session 17E, Food Chemistry: Proteins [on-line] [retrieved Nov. 8, 2004] Retrieved from the Internet: <URL: http://www.ift.confex.com.ift/2004/techprogram/paper_23066.htm>, 17E-4 (2004).
D'Hondt Erik "Possible approaches to develop vaccines against hepatitis A" Vaccine 10(Suppl 1):S48 (1992).
Daemen ALH "The destruction of enzymes and bacteria during the spray-drying of milk and whey. 2. The effect of the drying conditions" Neth Milk Dairy J 36:211-229 (1982).
Dahl Karen E et al "Selective induction of Transforming Growth Factor β in Human Monocytes by Lipoarabinomannen of *Mycobacterium tuberculosis*" Infect Immun 64(2):399-405 (1996).
Dalby Richard N et al "Relationship Between Particle Morphology and Drug Release Properties After Hydration Aerosols containing Liposome Forming Ingredients" Pharm Res 5(10):S-94, Abstract PD 866 (1988).
Dalby Richard N et al "Inhalation therapy: technological milestones in asthma treatment" Adv Drug Del Rev 85:779-791 (2003).
Dalby Richard N et al "Droplet Drying and Electrostatic Collection. A Novel Alternative to Conventional Comminution Techniques" J Biopharm Sci 3(1/2):91-99 (1992).
Darrington Richard T et al "Evidence for a Common Intermediate in Insulin Deamidation and Covalent Dimer Formation: Effects of pH and Aniiine Trapping in Dilute Acidic Solutions" J Pharm Sci 84(3):275 (1995).
De Carlo S et al "Unexpected property of trehalose as observed by cryo-electron microscopy" J Microscopy 198(1):40-45 (1999).
De Young Linda R et al "The Aerodose Multidose Inhaler Device Design and Delivery Characteristics" Resp Drug Del VI, p. 91 (1998).

Dose K et al "Survival in Extreme Dryness and DNA-Single-Strand Breaks" Adv Space Res 12(4):221-229 (1992).
Dunbar Craig A et al "Dispersion and Characterization of Pharmaceutical Dry Powder Aerosols" KONA 16:7 (1998).
During Matthew J et al "Long-Term Behavioral Recovery in Parkinsonian Rats by an HSV Vector Expressing Tyrosine Hydroxylase" Science 266:1399 (1994).
Düzgünes Nejat et al "Studies on the Mechanism of Membrane Fusion. Role of Head-Group Composition in Calcium- and Magnesium-Induced Fusion of Mixed Phospholipid Vesicles" Biochim Blophys Acta 642:182-195 (1981).
Ebara Yasuhito et al "Interactions of Calcium Ions with Phospholipid Membranes. Studies on *x*-A isotherms and Elctrochemical and Quartz-Crystal Microbalance Measurements" Langmuir 19:2267-2271 (1994).
Edwards Anthony D et al "Crystallization of Pure Anhydrous Polymorphs of Carbamazepine by Solution Enhanced Dispersion with Supercritical Fluids (SEDS™)" J Pharm Sci 90(8):1115 (2001).
Edwards David A et al "Large Porous Particles for Pulmonary Drug Delivery" Science 276:1868 (1997).
Eisenberg Moisés et al "Adsorption of Monovalent Cations to Bilayer Membranes Containing Negative Phospholipids" Biochemistry 18(23):5213 (1979).
Eleutherio Ells CA et al "Role of the trehalose carrier in dehydration resistance of *Saccharomyces cerevisiae*" Biochim Biophys Acta 1156:263-266 (1993).
Elkordy Amai A "Integrity of crystalline lysozyme exceeds that of a spray-dried form" Intl J Pharm 247:79-90 (2002).
"Estradiol" Merck Index, 12$^{th}$ ed, Susan Budaveri et al ed, monograph 3746, p. 630 (1996).
Fahy GM et al "Vitrification as an Approach to Cryopreservation" Cryobiology 21:407-426 (1984).
Fakes MG et al "Moisture sorption behavior of selected bulking agents used in lyophilized products" PDA J Pharm Sci Technol 54(2):144-9 (2000), Abstract [on-line] [retrieved Sep. 25, 2005] Retrieved from the Internet <URL: http://www.ncbi.nlm.nih.gov>, 2002.
Finar IL, Chemistry. Stereochemistry and the Chemistry of Natural Products, 5$^{th}$ ed, Longman, Section 14, under "Carbohydrate", Organic Chemistry, vol. 2 p. 323.
Forbes Robert T et al "Water Vapor Sorption Studies on the Physical Stability of a Series of Spray-Dried Protein/Sugar Powders for Inhalation" J Pharm Sci 87(11):1316 (1998).
Franks Felix et al "Materials Science and the Production of Shelf-Stable Biologicals" BioPharm, p. 38-42, p. 55 (1991).
Franks Felix "Freeze-Drying: From Empiricism to predictability" Cryo-Letters 11:93-110 (1990).

SEM photomicrographs depicting the effect the of calcium on the morphology of spray-dried DSPC particles; (A) Ca/DSPC = 1; (B) Ca/DSPC = 0.5; (C) Ca/DSPC = 0.25; (D) Ca/DSPC = 0

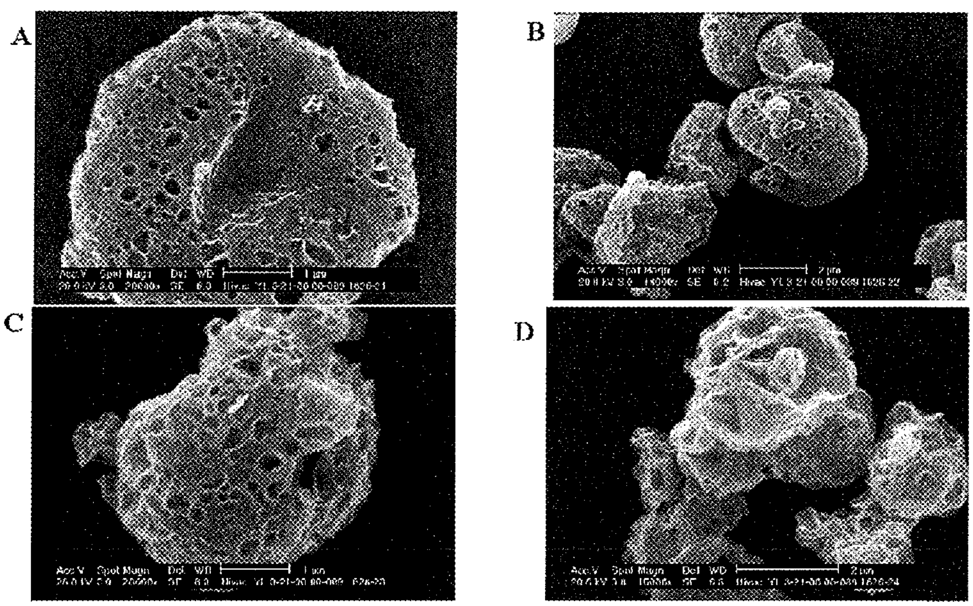

Fig. 2

Spreadability of Dry Phospholipid powders Versus Hydrated Phospholipids

PHOSPHOLIPID-BASED POWDERS FOR DRUG DELIVERY

CROSS REFERENCE TO RELATED APPLICATIONS

This application is a continuation application of pending U.S. patent application Ser. No. 09/851,226, filed on 8 May 2001, and is also a continuation application of U.S. patent application Ser. No. 10/141,219, filed on 7 May 2002, both of which claim benefit of the priority of U.S. Provisional Application Ser. No. 60/208,896 filed Jun. 2, 2000 and U.S. Provisional Application Ser. No. 60/216,621 filed Jul. 7, 2000 and is a continuation-in-part of U.S. patent application Ser. No. 09/568,818, filed May 10, 2000.

FIELD OF THE INVENTION

The present invention relates to particulate compositions suitable for drug delivery, preferably via inhalation. In particular, the present invention provides phospholipid-containing particulate compositions comprising a polyvalent cation. The particulate compositions of the present invention exhibit an increased gel-to-liquid crystal transition temperatures resulting in improved dispersibility and storage stability.

BACKGROUND OF THE INVENTION

Phospholipids are major components of cell and organelle membranes, blood lipoproteins, and lung surfactant. In terms of pulmonary drug delivery, phospholipids have been investigated as therapeutic agents for the treatment of respiratory distress syndrome (i.e. exogenous lung surfactants), and as suitable excipients for the delivery of actives. The interaction of phospholipids with water is critical to the formation, maintenance, and function of each of these important biological complexes (McIntosh and Magid). At low temperatures in the gel phase, the acyl chains are in a conformationally well-ordered state, essentially in the all-trans configuration. At higher temperatures, above the chain melting temperature, this chain order is lost, owing to an increase in gauche conformer content (Seddon and Cevc).

Several exogenous lung surfactants have been marketed and include products derived from bovine lungs (Survanta®, Abbott Laboratories), porcine lungs (CuroSurf®, Dey Laboratories), or completely synthetic surfactants with no apoproteins (e.g. ALEC®, ExoSurf® Glaxo Wellcome). To date, these products have been utilized for the treatment of infant respiratory distress syndrome (IRDS). None have been successful in receiving FDA approval for the treatment of adult respiratory distress syndrome (ARDS). The current infant dose is 100 mg/kg. For a 50 kg adult, this would translate into a dose of 5 g. A dose of this amount can only be administered to ARDS patients by direct instillation into the patient's endotracheal tube, or possibly via nebulization of aqueous dispersions of the surfactant material.

Instillation of surfactants leads to deposition primarily in the central airways, and little of the drug makes it to the alveoli, where it is needed to improve gas exchange in these critically ill patients. Nebulization of surfactant may allow for greater peripheral delivery, but is plagued by the fact that (a) current nebulizers are inefficient devices and only ca. 10% of the drug actually reaches the patients lungs; (b) the surfactant solutions foam during the nebulization process, leading to complications and further loss of drug. It is believed that as much as 99% of the administered surfactant may be wasted due to poor delivery to the patient. If more effective delivery of surfactant could be achieved, it is likely that the administered dose and cost for treatment of ARDS could be dramatically decreased.

Further, lung surfactant has been shown to modulate mucous transport in airways. In this regard, the chronic administration of surfactant for the treatment of patients with chronic obstructive pulmonary disease (COPD) has been suggested. Still other indications with significantly lower doses may be open to treatment if a dry powder form of a lung surfactant were available. The powdered surfactant formulation may be purely synthetic (i.e. with no added apoproteins). Alternatively, the powder formulation could contain the hydrophobic apoproteins SP-B or SP-C or alternative recombinant or synthetic peptide mimetics (e.g. $KL_4$).

Due to its spreading characteristics on lung epithelia, surfactant has been proposed as the ideal carrier for delivery of drugs to the lung, and via the lung to the systemic circulation. Once again, achieving efficient delivery to the lung is important, especially in light of the potential high cost of many of the current products. One potential way to deliver drugs in phospholipids is as a dry powder aerosolized to the lung. Most fine powders (<5 μm) exhibit poor dispersibility. This can be problematic when attempting to deliver, aerosolize, and/or package the powders.

The major forces that control particle-particle interactions can be divided into short and long range forces. Long-range forces include gravitational attractive forces and electrostatics, where the interaction varies as the square of the separation distance. Short-range attractive forces dominate for dry powders and include van der Waals interactions, hydrogen bonding, and liquid bridging. Liquid bridging occurs when water molecules are able to irreversibly bind particles together.

Phospholipids are especially difficult to formulate as dry powders as their low gel to liquid crystal transition temperature (Tm) values and amorphous nature lead to powders which are very sticky and difficult to deaggregate and aerosolize. Phospholipids with Tm values less than 10° C. (e.g. egg PC or any unsaturated lipids) form highly cohesive powders following spray-drying. Inspection of the powders via scanning electron microscopy reveals highly agglomerated particles with surfaces that appear to have been melted/annealed. Formulating phospholipid powders which have low Tm are problematic, especially if one hopes to achieve a certain particle morphology, as in the case of aerosol delivery. Thus, it would be advantageous to find ways to elevate the Tm of these lipids. Examples of particulate compositions incorporating a surfactant are disclosed in PCT publications WO 99/16419, WO 99/38493, WO 99/66903, WO 00/10541, and U.S. Pat. No. 5,855,913, which are hereby incorporated in their entirety by reference.

Currently, lung surfactant is given to patients by intubating them and instilling a suspension of lung surfactant directly into the lungs. This is a highly invasive procedure which generally is not performed on conscious patients, and as do most procedures, carries its own risks. Potential applications for lung surfactant beyond the current indication of respiratory distress syndrome in neonates are greatly limited by this method of administration. For example, lung surfactant may be useful in a variety of disease states that are, in part, due to decreased lung surfactant being present in the lungs. U.S. Pat. Nos. 5,451,569, 5,698,537, and 5,925,337, and PCT publications WO 97/26863 and WO 00/27360, for example, disclose the pulmonary administration of lung surfactant to treat various conditions, the disclosures of which are hereby incorporated in their entirety by reference. Diseases that are thought to be possibly aggravated by lung surfactant deficiency include cystic fibrosis, chronic obstructive pulmonary disease, and asthma, just to name a few. The delivery of exogenous lung surfactant, in a topical fashion, to patients suffering from these diseases may ameliorate certain signs and symptoms of the diseases. For chronic conditions, the regular (once or more times per day on a prolonged basis) delivery of lung surfactant via intubation and instillation to ambulatory patients is impractical. Further, because of their high surface activity, lung surfactant suspensions are not amenable to nebulization due to foaming. The current delivery of phospholipid-based preparations by instillation or nebulization are highly inefficient in delivering material to the peripheral lung. Therefore, the ability to deliver lung surfactant to patients via dry powder inhalation would be a tremendous advantage over the current method, since it would avoid the need for intubation, thereby expanding the potential uses of lung surfactant in the clinical setting.

SUMMARY OF THE INVENTION

The present invention provides for dry powder compositions of phospholipid suitable for drug delivery. According to a preferred embodiment, the phospholipid compositions are efficiently delivered to the deep lung. The phospholipid may be delivered alone, as in the case of lung surfactant or in combination with another active agent and/or excipient. The use of dry powder compositions may also open new indications for use since the patient need not be intubated. According to one embodiment, the compositions of the present invention may be delivered from a simple passive DPI device. The present compositions allow for greater stability on storage, and for more efficient delivery to the lung.

It has been found in the present work that the gel to liquid crystal phase transition of the phospholipid, Tm, is critical in obtaining phospholipid-based dry powders that both flow well, and are readily dispersible from a dry powder inhaler device. The present invention is related to the use of polyvalent cations, preferably divalent cations to dramatically increase the Tm of phospholipids. As used herein, "polyvalent cations" refers to polyvalent salts or their ionic components. Increasing the Tm of the phospholipid leads to the following formulation improvements: (a) Increases in Tm allows the formulator to increase the inlet and outlet temperatures on the spray-drier, or on a vacuum oven during a secondary drying step. Higher temperatures allow the drying phase of the spray-drying to be controllable over a wider temperature range, thereby facilitating removal of trapped blowing agent used in the manufacture of powders according to one aspect of the present invention; (b) Increases in Tm allow for a large difference between Tm and the storage temperature, thereby improving powder stability; (c) Increases in Tm yield phospholipids in the gel state, where they are less prone to taking up water and water bridging phenomena (d) Increases in Tm yield phospholipids which are able to spread more effectively upon contact with lung epithelia than hydrated phospholipids, thereby allowing drugs to be more effectively distributed to the lung periphery; (e) Increases in Tm dramatically improves the dispersibility of the resulting powders, thereby improving the emitted dose and fine particle fraction following pulmonary delivery.

According to a preferred embodiment, the present invention relates to highly dispersible dry powder compositions of phospholipids suitable for pulmonary delivery. The compositions according to the present invention are useful as synthetic lung surfactants for the treatment of local lung conditions (e.g. asthma, COPD), or as carriers for the pulmonary delivery of active agents, including small molecules, peptides, proteins, DNA, and immunologic agents.

One aspect of the present invention is to provide powdered, dispersible compositions having stable dispersibility over time. The compositions exhibit a characteristic gel to liquid crystal phase transition temperature, Tm, which is greater than a recommended storage temperature, Ts, typically room temperature, by at least 20° C. Preferably Tm is at least 40° C. greater than Ts.

It is a further aspect of the present invention that the increases in Tm afforded by addition of divalent cations leads to the ability to dry the powders in a secondary drying step at temperatures (Td) up to the Tm of the lipid. As well, it is possible to increase the inlet and outlet temperatures on a spray-drier should a spray-dry process be employed (Td≈Tm).

It is a further aspect of the present invention to provide a powdered, dispersible form of a lung surfactant having stable dispersibility over time and excellent spreading characteristics on an aqueous subphase.

It is a further aspect of the present invention that the improvements in dispersibility obtained by the present compositions allow for a simple, passive inhaler device to be utilized, in spite of the fact that particles less than 5 μm are contemplated and generally preferred. Present state-of-the-art formulations for fine particles utilize blends with large lactose particles to improve dispersibility. When placed in a passive DPI device such formulations exhibit a strong dependence of emitted dose and lung deposition on the patient's inspiratory flowrate. The present compositions exhibit little flowrate dependence on the emitted dose and lung deposition.

BRIEF DESCRIPTION OF THE DRAWINGS

FIG. 2 are SEM photographs the effect of calcium ion concentration on the morphology of spray-dried particles according to the invention.

DETAILED DESCRIPTION OF THE INVENTION

Definitions

Figure 1:
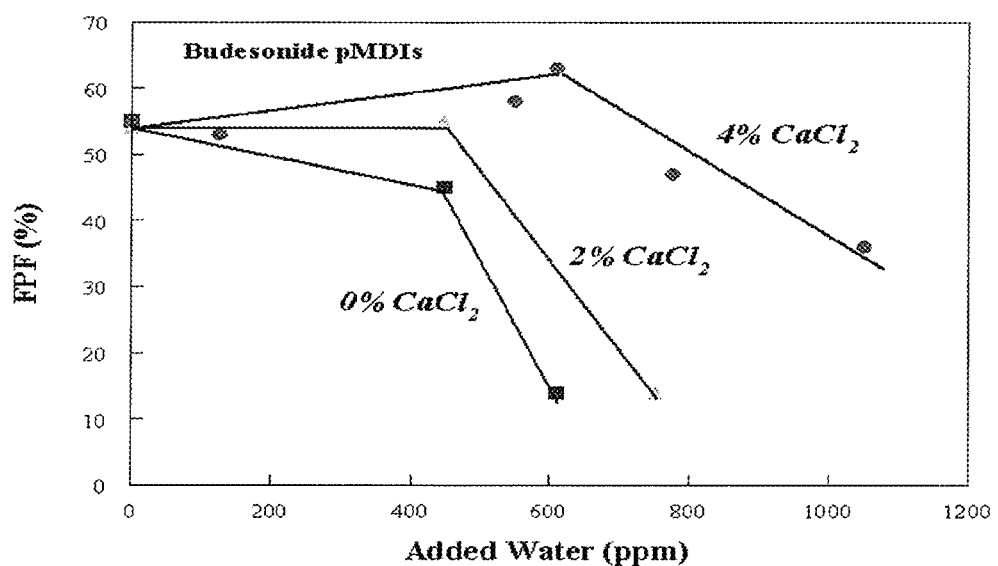
FIG. 1 is a graph depicting the physical stability of budesonide in pMDI.
Figure 3:
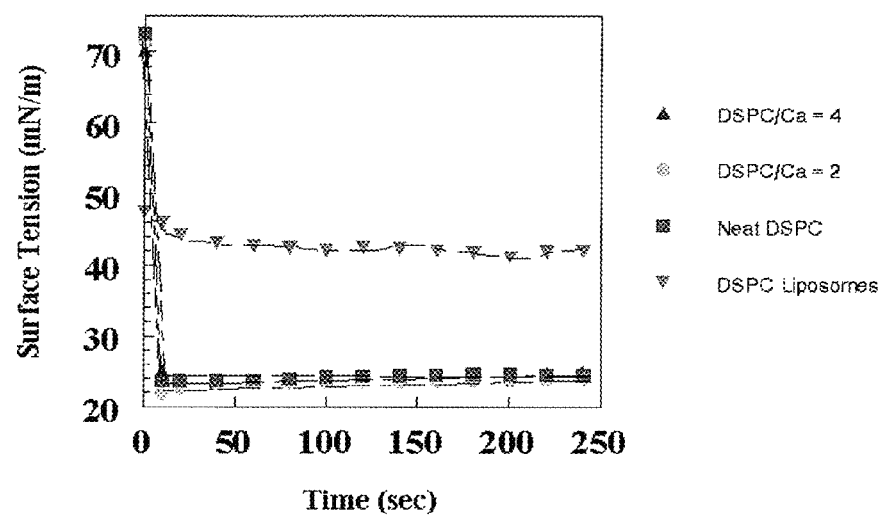
FIG. 3 is a graph depicting the spreading characteristics of powders of the instant invention.

"Active agent" as described herein includes an agent, drug, compound, composition of matter or mixture thereof which provides some diagnostic, prophylactic, or pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. The active agent that can be delivered includes antibiotics, antibodies, antiviral agents, anepileptics, analgesics, anti-inflammatory agents and bronchodilators, and viruses and may be inorganic and organic compounds, including, without limitation, drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

Examples of active agents useful in this invention include but are not limited to insulin, calcitonin, erythropoietin (EPO), Factor VIII, Factor IX, ceredase, cerezyme, cyclosporine, granulocyte colony stimulating factor (GCSF), alpha-1 proteinase inhibitor, elcatonin, granulocyte macrophage colony stimulating factor (GMCSF), growth hormone, human growth hormone (hGH), growth hormone releasing hormone (GHRH), heparin, low molecular weight heparin (LMWH), interferon alpha, interferon beta, interferon gamma, interleukin-2, luteinizing hormone releasing hormone (LHRH), leuprolide, somatostatin, somatostatin analogs including octreotide, vasopressin analog, follicle stimulating hormone (FSH), immunoglobulins, insulin-like growth factor, insulintropin, interleukin-1 receptor antagonist, interleukin-3, interleukin-4, interleukin-6, macrophage colony stimulating factor (M-CSF), nerve growth factor, parathyroid hormone (PTH), thymosin alpha 1, IIb/IIIa inhibitor, alpha-1 antitrypsin, respiratory syncytial virus antibody, cystic fibrosis transmembrane regulator (CFTR) gene, deoxyribonuclease (Dnase), bactericidal/permeability increasing protein (BPI), anti-CMV antibody, interleukin-1 receptor, 13-cis retinoic acid, nicotine, nicotine bitartrate, gentamicin, ciprofloxacin, amphotericin, amikacin, tobramycin, pentamidine isethionate, albuterol sulfate, metaproterenol sulfate, beclomethasone dipropionate, triamcinolone acetamide, budesonide acetonide, ipratropium bromide, flunisolide, fluticasone, fluticasone propionate, salmeterol xinofoate, formeterol fumarate, cromolyn sodium, ergotamine tartrate and the analogues, agonists and antagonists of the above. Active agents may further comprise nucleic acids, present as bare nucleic acid molecules, viral vectors, associated viral particles, nucleic acids associated or incorporated within lipids or a lipid-containing material, plasmid DNA or RNA or other nucleic acid construction of a type suitable for transfection or transformation of cells, particularly cells of the alveolar regions of the lungs. The active agents may be in various forms, such as soluble and insoluble charged or uncharged molecules, components of molecular complexes or pharmacologically acceptable salts. The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines.

As used herein, the term "emitted dose" or "ED" refers to an indication of the delivery of dry powder from a suitable inhaler device after a firing or dispersion event from a powder unit or reservoir. ED is defined as the ratio of the dose delivered by an inhaler device (described in detail below) to the nominal dose (i.e., the mass of powder per unit dose placed into a suitable inhaler device prior to firing). The ED is an experimentally-determined amount, and is typically determined using an in-vitro device set up which mimics patient dosing. To determine an ED value, a nominal dose of dry powder (as defined above) is placed into a suitable dry powder inhaler, which is then actuated, dispersing the powder. The resulting aerosol cloud is then drawn by vacuum from the device, where it is captured on a tared filter attached to the device mouthpiece. The amount of powder that reaches the filter constitutes the delivered dose. For example, for a 5 mg, dry powder-containing blister pack placed into an inhalation device, if dispersion of the powder results in the recovery of 4 mg of powder on a tared filter as described above, then the ED for the dry powder composition is: 4 mg (delivered dose)/5 mg (nominal dose)×100=80%.

"Mass median diameter" or "MMD" is a measure of mean particle size, since the powders of the invention are generally polydisperse (i.e., consist of a range of particle sizes). MMD values as reported herein are deter mined by laser diffraction, although any number of commonly employed techniques can be used for measuring mean particle size.

"Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

The present invention is directed to the formulation of dry phospholipid-polyvalent cation based particulate composition. In particular, the present invention is directed to the use of polyvalent cations in the manufacture of phospholipid-containing, dispersible particulate compositions for pulmonary administration to the respiratory tract for local or systemic therapy via aerosolization, and to the particulate compositions made thereby. The invention is based, at least in part, on the surprising discovery of the beneficial aerosolization and stabilization properties of phospholipid-containing particulate compositions comprising a polyvalent cation. These unexpected benefits include a dramatic increase in the gel-to-liquid crystal phase transition temperature (Tm) of the particulate composition, improved dispersibility of such particulate compositions, improved spreadability of the particulate compositions upon contact with lung epithelia thereby allowing drugs to be more effectively distributed to the lung periphery, and improved storage stability of the particulate compositions.

It is surprisingly unexpected that the addition of a very hygroscopic salt such as calcium chloride would stabilize a dry powder prone to moisture induced destabilization, as one would expect that the calcium chloride would readily pick up water leading to particle aggregation. However, this is not what is observed. In contrast, addition of calcium ions leads to a dramatic improvement in the stability of the dry phospholipid-based powder to humidity. While not being bound to any theory, it is believed that calcium ions are believed to intercalate the phospholipid membrane, thereby interacting directly with the negatively charged portion of the zwitterionic headgroup. The result of this interaction is increased dehydration of the headgroup area and condensation of the acyl-chain packing, all of which leads to increased thermodynamic stability of the phospholipids.

The polyvalent cation for use in the present invention is preferably a divalent cation including calcium, magnesium, zinc, iron, and the like. According to the invention, the polyvalent cation is present in an amount effective to increase the Tm of the phospholipid such that the particulate composition exhibits a Tm which is greater than its storage temperature Ts by at least 20° C., preferably at least 40° C. The molar ratio of polyvalent cation to phospholipid should be at least 0.05, preferably 0.05-2.0, and most preferably 0.25-1.0. A molar ratio of polyvalent cation:phospholipid of about 0.50 is particularly preferred according to the present invention. Calcium is the particularly preferred polyvalent cation of the present invention and is provided as calcium chloride.

In a broad sense, phospholipid suitable for use in the present invention include any of those known in the art.

According to a preferred embodiment, the phospholipid is most preferably a saturated phospholipid. According to a particularly preferred embodiment, saturated phosphatidylcholines are used as the phospholipid of the present invention. Preferred acyl chain lengths are 16:0 and 18:0 (i.e. palmitoyl and stearoyl). According to one embodiment directed to lung surfactant compositions, the phospholipid can make up to 90 to 99.9% w/w of the composition. Suitable phospholipids according to this aspect of the invention include natural or synthetic lung surfactants such as those commercially available under the trademarks ExoSurf, InfaSurf® (Ony, Inc.), Survanta, CuroSurf, and ALEC. For drug delivery purposes wherein an active agent is included with the particulate composition, the phospholipid content will be determined by the drug activity, the mode of delivery, and other factors and will likely be in the range from about 20% to up to 99.9% w/w. Thus, drug loading can vary between about 0.1% and 80% w/w, preferably 5-70% w/w.

According to a preferred embodiment, it has been found in the present work that the Tm of the phospholipid is critical in obtaining phospholipid-based dry powders that both flow well and are readily dispersible from a dry powder inhaler (DPI). The Tm of the modified lipid microparticles can be manipulated by varying the amount of polyvalent cations in the formulation.

Phospholipids from both natural and synthetic sources are compatible with the present invention and may be used in varying concentrations to form the structural matrix. Generally compatible phospholipids comprise those that have a gel to liquid crystal phase transition greater than about 40° C. Preferably the incorporated phospholipids are relatively long chain (i.e. $C_{16}$-$C_{22}$) saturated lipids and more preferably comprise saturated phospholipids, most preferably saturated phosphatidylcholines having acyl chain lengths of 16:0 or 18:0 (palmitoyl and stearoyl). Exemplary phospholipids useful in the disclosed stabilized preparations comprise, phosphoglycerides such as dipalmitoylphosphatidylcholine, disteroylphosphatidylcholine, diarachidoylphosphatidylcholine dibehenoylphosphatidylcholine, diphosphatidyl glycerol, short-chain phosphatidylcholines, long-chain saturated phosphatidylethanolamines, long-chain saturated phosphatidylserines, long-chain saturated phosphatidylglycerols, long-chain saturated phosphatidylinositols.

In addition to the phospholipid, a co-surfactant or combinations of surfactants, including the use of one or more in the liquid phase and one or more associated with the particulate compositions are contemplated as being within the scope of the invention. By "associated with or comprise" it is meant that the particulate compositions may incorporate, adsorb, absorb, be coated with or be formed by the surfactant. Surfactants include fluorinated and nonfluorinated compounds and are selected from the group consisting of saturated and unsaturated lipids, nonionic detergents, nonionic block copolymers, ionic surfactants and combinations thereof. In those embodiments comprising stabilized dispersions, such nonfluorinated surfactants will preferably be relatively insoluble in the suspension medium. It should be emphasized that, in addition to the aforementioned surfactants, suitable fluorinated surfactants are compatible with the teachings herein and may be used to provide the desired preparations.

Compatible nonionic detergents suitable as co-surfactants comprise: sorbitan esters including sorbitan trioleate (Span™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.) which is incorporated herein in its entirety. Preferred block copolymers include diblock and triblock copolymers of polyoxyethylene and polyoxypropylene, including poloxamer 188 (Pluronic™ F-68), poloxamer 407 (Pluronic™ F-127), and poloxamer 338. Ionic surfactants such as sodium sulfosuccinate, and fatty acid soaps may also be utilized.

Other lipids including glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate may also be used in accordance with the teachings of this invention.

It will further be appreciated that the particulate compositions according to the invention may, if desired, contain a combination of two or more active ingredients. The agents may be provided in combination in a single species of particulate composition or individually in separate species of particulate compositions. For example, two or more active agents may be incorporated in a single feed stock preparation and spray dried to provide a single particulate composition species comprising a plurality of active agents. Conversely, the individual actives could be added to separate stocks and spray dried separately to provide a plurality of particulate composition species with different compositions. These individual species could be added to the suspension medium or dry powder dispensing compartment in any desired proportion and placed in the aerosol delivery system as described below. Further, as alluded to above, the particulate compositions (with or without an associated agent) may be combined with one or more conventional (e.g. a micronized drug) active or bioactive agents to provide the desired dispersion stability or powder dispersibility.

Based on the foregoing, it will be appreciated by those skilled in the art that a wide variety of active agents may be incorporated in the disclosed particulate compositions. Accordingly, the list of preferred active agents above is exemplary only and not intended to be limiting. It will also be appreciated by those skilled in the art that the proper amount of agent and the timing of the dosages may be determined for the particulate compositions in accordance with already existing information and without undue experimentation.

In addition to the phospholipid and polyvalent cation, the microparticles of the present invention may also include a biocompatible, preferably biodegradable polymer, copolymer, or blend or other combination thereof. In this respect useful polymers comprise polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). Examples of polymeric resins that would be useful for the preparation of perforated ink microparticles include: styrene-butadiene, styrene-isoprene, styrene-acrylonitrile, ethylene-vinyl acetate, ethylene-acrylate, ethylene-acrylic acid, ethylene-methylacrylatate, ethylene-ethyl acrylate, vinyl-methyl methacrylate, acrylic acid-methyl methacrylate, and vinyl chloride-vinyl acetate. Those skilled in the art will appreciate that, by selecting the appropriate polymers, the delivery efficiency of the particulate compositions and/or the stability of the dispersions may be tailored to optimize the effectiveness of the active or agent.

Besides the aforementioned polymer materials and surfactants, it may be desirable to add other excipients to a particulate composition to improve particle rigidity, production yield, emitted dose and deposition, shelf-life and patient acceptance. Such optional excipients include, but are not limited to: coloring agents, taste masking agents, buffers, hygroscopic agents, antioxidants, and chemical stabilizers. Further, various excipients may be incorporated in, or added to, the particulate matrix to provide structure and form to the particulate compositions (i.e. microspheres such as latex particles). In this regard it will be appreciated that the rigidifying components can be removed using a post-production technique such as selective solvent extraction.

Other excipients may include, but are not limited to, carbohydrates including monosaccharides, disaccharides and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins and maltodextrins. Other excipients suitable for use with the present invention, including amino acids, are known in the art such as those disclosed in WO 95/31479, WO 96/32096, and WO 96/32149. Mixtures of carbohydrates and amino acids are further held to be within the scope of the present invention. The inclusion of both inorganic (e.g. sodium chloride, etc.), organic acids and their salts (e.g. carboxylic acids and their salts such as sodium citrate, sodium ascorbate, magnesium gluconate, sodium gluconate, tromethamine hydrochloride, etc.) and buffers is also contemplated. The inclusion of salts and organic solids such as ammonium carbonate, ammonium acetate, ammonium chloride or camphor are also contemplated.

Yet other preferred embodiments include particulate compositions that may comprise, or may be coated with, charged species that prolong residence time at the point of contact or enhance penetration through mucosae. For example, anionic charges are known to favor mucoadhesion while cationic charges may be used to associate the formed microparticulate with negatively charged bioactive agents such as genetic material. The charges may be imparted through the association or incorporation of polyanionic or polycationic materials such as polyacrylic acids, polylysine, polylactic acid and chitosan.

According to a preferred embodiment, the particulate compositions may be used in the form of dry powders or in the form of stabilized dispersions comprising a non-aqueous phase. Accordingly, the dispersions or powders of the present invention may be used in conjunction with metered dose inhalers (MDIs), dry powder inhalers (DPIs), atomizers, nebulizers or liquid dose instillation (LDI) techniques to provide for effective drug delivery. With respect to inhalation therapies, those skilled in the art will appreciate that the hollow and porous microparticles of the present invention are particularly useful in DPIs. Conventional DPIs comprise powdered formulations and devices where a predetermined dose of medicament, either alone or in a blend with lactose carrier particles, is delivered as an aerosol of dry powder for inhalation.

The medicament is formulated in a way such that it readily disperses into discrete particles with an MMD between 0.5 to 20 µm, preferably 0.5-5 µm, and are further characterized by an aerosol particle size distribution less than about 10 µm mass median aerodynamic diameter (MMAD), and preferably less than 5.0 µm. The mass median aerodynamic diameters of the powders will characteristically range from about 0.5-10 µm, preferably from about 0.5-5.0 µm MMAD, more preferably from about 1.0-4.0 µm MMAD.

The powder is actuated either by inspiration or by some external delivery force, such as pressurized air. Examples of DPIs suitable for administration of the particulate compositions of the present invention are disclosed in U.S. Pat. Nos. 5,740,794, 5,785,049, 5,673,686, and 4,995,385 and PCT application nos. 00/72904, 00/21594, and 01/00263, hereby incorporated in their entirety by reference. DPI formulations are typically packaged in single dose units such as those disclosed in the above mentioned patents or they employ reservoir systems capable of metering multiple doses with manual transfer of the dose to the device.

As discussed above, the stabilized dispersions disclosed herein may also be administered to the nasal or pulmonary air passages of a patient via aerosolization, such as with a metered dose inhaler. The use of such stabilized preparations provides for superior dose reproducibility and improved lung deposition as disclosed in WO 99/16422, hereby incorporated in its entirety by reference. MDIs are well known in the art and could easily be employed for administration of the claimed dispersions without undue experimentation. Breath activated MDIs, as well as those comprising other types of improvements which have been, or will be, developed are also compatible with the stabilized dispersions and present invention and, as such, are contemplated as being within the scope thereof. However, it should be emphasized that, in preferred embodiments, the stabilized dispersions may be administered with an MDI using a number of different routes including, but not limited to, topical, nasal, pulmonary or oral. Those skilled in the art will appreciate that, such routes are well known and that the dosing and administration procedures may be easily derived for the stabilized dispersions of the present invention.

Along with the aforementioned embodiments, the stabilized dispersions of the present invention may also be used in conjunction with nebulizers as disclosed in PCT WO 99/16420, the disclosure of which is hereby incorporated in its entirety by reference, in order to provide an aerosolized medicament that may be administered to the pulmonary air passages of a patient in need thereof. Nebulizers are well known in the art and could easily be employed for administration of the claimed dispersions without undue experimentation. Breath activated nebulizers, as well as those comprising other types of improvements which have been, or will be, developed are also compatible with the stabilized dispersions and present invention and are contemplated as being with in the scope thereof.

Along with DPIs, MDIs and nebulizers, it will be appreciated that the stabilized dispersions of the present invention may be used in conjunction with liquid dose instillation or LDI techniques as disclosed in, for example, WO 99/16421 hereby incorporated in its entirety by reference. Liquid dose instillation involves the direct administration of a stabilized dispersion to the lung. In this regard, direct pulmonary administration of bioactive compounds is particularly effective in the treatment of disorders especially where poor vascular circulation of diseased portions of a lung reduces the effectiveness of intravenous drug delivery. With respect to LDI the stabilized dispersions are preferably used in conjunction with partial liquid ventilation or total liquid ventilation. Moreover, the present invention may further comprise introducing a therapeutically beneficial amount of a physiologically acceptable gas (such as nitric oxide or oxygen) into the pharmaceutical microdispersion prior to, during or following administration.

Particularly preferred embodiments of the invention incorporate spray dried, hollow and porous particulate compositions as disclosed in WO 99/16419, hereby incorporated in its entirety by reference. Such particulate compositions comprise particles having a relatively thin porous wall defining a large internal void, although, other void containing or perforated structures are contemplated as well. In preferred embodiments the particulate compositions will further comprise an active agent.

Compositions according to the present invention typically yield powders with bulk densities less than 0.5 g/cm$^3$ or 0.3 g/cm$^3$, preferably less 0.1 g/cm$^3$ and most preferably less than 0.05 g/cm$^3$. By providing particles with very low bulk density, the minimum powder mass that can be filled into a unit dose container is reduced, which eliminates the need for carrier particles. That is, the relatively low density of the powders of the present invention provides for the reproducible administration of relatively low dose pharmaceutical compounds. Moreover, the elimination of carrier particles will potentially minimize throat deposition and any "gag" effect, since the large lactose particles will impact the throat and upper airways due to their size.

It will be appreciated that the particulate compositions disclosed herein comprise a structural matrix that exhibits, defines or comprises voids, pores, defects, hollows, spaces, interstitial spaces, apertures, perforations or holes. The absolute shape (as opposed to the morphology) of the perforated microstructure is generally not critical and any overall configuration that provides the desired characteristics is contemplated as being within the scope of the invention. Accordingly, preferred embodiments can comprise approximately microspherical shapes. However, collapsed, deformed or fractured particulates are also compatible.

In accordance with the teachings herein the particulate compositions will preferably be provided in a "dry" state. That is the microparticles will possess a moisture content that allows the powder to remain chemically and physically stable during storage at ambient temperature and easily dispersible. As such, the moisture content of the microparticles is typically less than 6% by weight, and preferably less 3% by weight. In some instances the moisture content will be as low as 1% by weight. Of course it will be appreciated that the moisture content is, at least in part, dictated by the formulation and is controlled by the process conditions employed, e.g., inlet temperature, feed concentration, pump rate, and blowing agent type, concentration and post drying.

Reduction in bound water leads to significant improvements in the dispersibility and flowability of phospholipid based powders, leading to the potential for highly efficient delivery of powdered lung surfactants or particulate composition comprising active agent dispersed in the phospholipid. The improved dispersibility allows simple passive DPI devices to be used to effectively deliver these powders.

Although the powder compositions are preferably used for inhalation therapies, the powders of the present invention can also be administered by other techniques known in the art, including, but not limited to intramuscular, intravenous, intratracheal, intraperitoneal, subcutaneous, and transdermal, either as dry powders, reconstituted powders, or suspensions.

As seen from the passages above, various components may be associated with, or incorporated in the particulate compositions of the present invention. Similarly, several techniques may be used to provide particulates having the desired morphology (e.g. a perforated or hollow/porous configuration), dispersibility and density. Among other methods, particulate compositions compatible with the instant invention may be formed by techniques including spray drying, vacuum drying, solvent extraction, emulsification or lyophilization, and combinations thereof. It will further be appreciated that the basic concepts of many of these techniques are well known in the prior art and would not, in view of the teachings herein, require undue experimentation to adapt them so as to provide the desired particulate compositions.

While several procedures are generally compatible with the present invention, particularly preferred embodiments typically comprise particulate compositions formed by spray drying. As is well known, spray drying is a one-step process that converts a liquid feed to a dried particulate form. With respect to pharmaceutical applications, it will be appreciated that spray drying has been used to provide powdered material for various administrative routes including inhalation. See, for example, M. Sacchetti and M. M. Van Oort in: Inhalation Aerosols: Physical and Biological Basis for Therapy, A. J. Hickey, ed. Marcel Dekkar, New York, 1996, which is incorporated herein by reference.

In general, spray drying consists of bringing together a highly dispersed liquid, and a sufficient volume of hot air to produce evaporation and drying of the liquid droplets. The preparation to be spray dried or feed (or feed stock) can be any solution, course suspension, slurry, colloidal dispersion, or paste that may be atomized using the selected spray drying apparatus. In preferred embodiments the feed stock will comprise a colloidal system such as an emulsion, reverse emulsion, microemulsion, multiple emulsion, particulate dispersion, or slurry. Typically the feed is sprayed into a current of warm filtered air that evaporates the solvent and conveys the dried product to a collector. The spent air is then exhausted with the solvent. Those skilled in the art will appreciate that several different types of apparatus may be used to provide the desired product. For example, commercial spray dryers manufactured by Buchi Ltd. or Niro Corp. will effectively produce particles of desired size.

It will further be appreciated that these spray dryers, and specifically their atomizers, may be modified or customized for specialized applications, i.e. the simultaneous spraying of two solutions using a double nozzle technique. More specifically, a water-in-oil emulsion can be atomized from one nozzle and a solution containing an anti-adherent such as mannitol can be co-atomized from a second nozzle. In other cases it may be desirable to push the feed solution though a custom designed nozzle using a high pressure liquid chromatography (HPLC) pump. Provided that microstructures comprising the correct morphology and/or composition are produced the choice of apparatus is not critical and would be apparent to the skilled artisan in view of the teachings herein. Examples of spray drying methods and systems suitable for making the dry powders of the present invention are disclosed in U.S. Pat. Nos. 6,077,543, 6,051, 256, 6,001,336, 5,985,248, and 5,976,574, hereby incorporated in their entirety by reference.

While the resulting spray-dried powdered particles typically are approximately spherical in shape, nearly uniform in size and frequently are hollow, there may be some degree of irregularity in shape depending upon the incorporated medicament and the spray drying conditions. In many instances dispersion stability and dispersibility of the particulate compositions appears to be improved if an inflating agent (or blowing agent) is used in their production as disclosed in WO 99/16419 cited above. Particularly preferred embodiments comprise an emulsion with the inflating agent as the disperse or continuous phase. The inflating agent is preferably dispersed with a surfactant solution, using, for instance, a commercially available microfluidizer at a pressure of about 5000 to 15,000 psi. This process forms an emulsion, preferably stabilized by an incorporated surfactant, typically comprising submicron droplets of water immiscible blowing agent dispersed in an aqueous continuous phase. The formation of such emulsions using this and other techniques are common and well known to those in the art. The blowing agent is preferably a fluorinated compound (e.g. perfluorohexane, perfluorooctyl bromide, perfluorooctyl ethane, perfluorodecalin, perfluorobutyl ethane) which vaporizes during the spray-drying process, leaving behind generally hollow, porous aerodynamically light microspheres. Other suitable liquid blowing agents include nonfluorinated oils, chloroform, Freons, ethyl acetate, alcohols and hydrocarbons. Nitrogen and carbon dioxide gases are also contemplated as a suitable blowing agent. Perfluorooctyl ethane is particularly preferred according to the invention.

Besides the aforementioned compounds, inorganic and organic substances which can be removed under reduced pressure by sublimation in a post-production step are also compatible with the instant invention. These sublimating compounds can be dissolved or dispersed as micronized crystals in the spray drying feed solution and include ammonium carbonate and camphor. Other compounds compatible with the present invention comprise rigidifying solid structures which can be dispersed in the feed solution or prepared in-situ. These structures are then extracted after the initial particle generation using a post-production solvent extraction step. For example, latex particles can be dispersed and subsequently dried with other wall forming compounds, followed by extraction with a suitable solvent.

Although the particulate compositions are preferably formed using a blowing agent as described above, it will be appreciated that, in some instances, no additional blowing agent is required and an aqueous dispersion of the medicament and/or excipients and surfactant(s) are spray dried directly. In such cases, the formulation may be amenable to process conditions (e.g., elevated temperatures) that may lead to the formation of hollow, relatively porous microparticles. Moreover, the medicament may possess special physicochemical properties (e.g., high crystallinity, elevated melting temperature, surface activity, etc.) that makes it particularly suitable for use in such techniques.

Regardless of which blowing agent is ultimately selected, it has been found that to compatible particulate compositions may be produced particularly efficiently using a Büchi mini spray drier (model B-191, Switzerland). As will be appreciated by those skilled in the art, the inlet temperature and the outlet temperature of the spray drier are not critical but will be of such a level to provide the desired particle size and to result in a product that has the desired activity of the medicament. In this regard, the inlet and outlet temperatures are adjusted depending on the melting characteristics of the formulation components and the composition of the feed stock. The inlet temperature may thus be between 60° C. and 170° C., with the outlet temperatures of about 40° C. to 120° C. depending on the composition of the feed and the desired particulate characteristics. Preferably these temperatures will be from 90° C. to 120° C. for the inlet and from 60° C. to 90° C. for the outlet. The flow rate which is used in the spray drying equipment will generally be about 3 ml per minute to about 15 ml per minute. The atomizer air flow rate will vary between values of 25 liters per minute to about 50 liters per minute. Commercially available spray dryers are well known to those in the art, and suitable settings for any particular dispersion can be readily determined through standard empirical testing, with due reference to the examples that follow. Of course, the conditions may be adjusted so as to preserve biological activity in larger molecules such as proteins or peptides.

Whatever components are selected, the first step in particulate production typically comprises feed stock preparation. If the phospholipid based particle is intended to act as a carrier for another active agent, the selected active agent is dissolved in a solvent, preferably water, to produce a concentrated solution. The polyvalent cation may be added to the active agent solution or may be added to the phospholipid emulsion as discussed below. The active agent may also be dispersed directly in the emulsion, particularly in the case of water insoluble agents. Alternatively, the active agent may be incorporated in the form of a solid particulate dispersion. The concentration of the active agent used is dependent on the amount of agent required in the final powder and the performance of the delivery device employed (e.g., the fine particle dose for a MDI or DPI). As needed, cosurfactants such as poloxamer 188 or span 80 may be dispersed into this annex solution. Additionally, excipients such as sugars and starches can also be added.

In selected embodiments a polyvalent cation-containing oil-in-water emulsion is then formed in a separate vessel. The oil employed is preferably a fluorocarbon (e.g., perfluorooctyl bromide, perfluorooctyl ethane, perfluorodecalin) which is emulsified with a phospholipid. For example, polyvalent cation and phospholipid may be homogenized in hot distilled water (e.g., 60° C.) using a suitable high shear mechanical mixer (e.g., Ultra-Turrax model T-25 mixer) at 8000 rpm for 2 to 5 minutes. Typically 5 to 25 g of fluorocarbon is added dropwise to the dispersed surfactant solution while mixing. The resulting polyvalent cation-containing perfluorocarbon in water emulsion is then processed using a high pressure homogenizer to reduce the particle size. Typically the emulsion is processed at 12,000 to 18,000 psi, 5 discrete passes and kept at 50 to 80° C.

The active agent solution and perfluorocarbon emulsion are then combined and fed into the spray dryer. Typically the two preparations will be miscible as the emulsion will preferably comprise an aqueous continuous phase. While the bioactive agent is solubilized separately for the purposes of the instant discussion it will be appreciated that, in other embodiments, the active agent may be solubilized (or dispersed) directly in the emulsion. In such cases, the active emulsion is simply spray dried without combining a separate active agent preparation.

In any event, operating conditions such as inlet and outlet temperature, feed rate, atomization pressure, flow rate of the drying air, and nozzle configuration can be adjusted in accordance with the manufacturer's guidelines in order to produce the required particle size, and production yield of the resulting dry particles. Exemplary settings are as follows: an air inlet temperature between 60° C. and 170° C.; an air outlet between 40° C. to 120° C.; a feed rate between 3 ml to about 15 ml per minute; and an aspiration air flow of 300 L/min. and an atomization air flow rate between 25 to 50 L/min. The selection of appropriate apparatus and processing conditions are well within the purview of a skilled artisan in view of the teachings herein and may be accomplished without undue experimentation. In any event, the use of these and substantially equivalent methods provide for the formation of hollow porous aerodynamically light microparticles with particle diameters appropriate for aerosol deposition into the lung. microstructures that are both hollow and porous, almost honeycombed or foam-like in appearance. In especially preferred embodiments the particulate compositions comprise hollow, porous spray dried microparticles.

Along with spray drying, particulate compositions useful in the present invention may be formed by lyophilization. Those skilled in the art will appreciate that lyophilization is a freeze-drying process in which water is sublimed from the composition after it is frozen. The particular advantage associated with the lyophilization process is that biologicals and pharmaceuticals that are relatively unstable in an aqueous solution can be dried without elevated temperatures (thereby eliminating the adverse thermal effects), and then stored in a dry state where there are few stability problems. With respect to the instant invention such techniques are particularly compatible with the incorporation of peptides, proteins, genetic material and other natural and synthetic macromolecules in particulate compositions without compromising physiological activity. Methods for providing lyophilized particulates are known to those of skill in the art and it would clearly not require undue experimentation to provide dispersion compatible microparticles in accordance with the teachings herein. The lyophilized cake containing a fine foam-like structure can be micronized using techniques known in the art to provide 3 to 10 μm sized particles. Accordingly, to the extent that lyophilization processes may be used to provide microparticles having the desired porosity and size they are in conformance with the teachings herein and are expressly contemplated as being within the scope of the instant invention.

Besides the aforementioned techniques, the particulate compositions or particles of the present invention may also be formed using a method where a feed solution (either emulsion or aqueous) containing wall forming agents is rapidly added to a reservoir of heated oil (e.g. perflubron or other high boiling FCs) under reduced pressure. The water and volatile solvents of the feed solution rapidly boils and are evaporated. This process provides a perforated structure from the wall forming agents similar to puffed rice or popcorn. Preferably the wall forming agents are insoluble in the heated oil. The resulting particles can then separated from the heated oil using a filtering technique and subsequently dried under vacuum.

Additionally, the particulate compositions of the present invention may also be formed using a double emulsion method. In the double emulsion method the medicament is first dispersed in a polymer dissolved in an organic solvent (e.g. methylene chloride, ethyl acetate) by sonication or homogenization. This primary emulsion is then stabilized by forming a multiple emulsion in a continuous aqueous phase containing an emulsifier such as polyvinylalcohol. Evaporation or extraction using conventional techniques and apparatus then removes the organic solvent. The resulting microspheres are washed, filtered and dried prior to combining them with an appropriate suspension medium in accordance with the present invention Whatever production method is ultimately selected for production of the particulate compositions, the resulting powders have a number of advantageous properties that make them particularly compatible for use in devices for inhalation therapies. In particular, the physical characteristics of the particulate compositions make them extremely effective for use in dry powder inhalers and in the formation of stabilized dispersions that may be used in conjunction with metered dose inhalers, nebulizers and liquid dose instillation. As such, the particulate compositions provide for the effective pulmonary administration of active agents.

In order to maximize dispersibility, dispersion stability and optimize distribution upon administration, the mean geometric particle size of the particulate compositions is preferably about 0.5-50 more preferably 1-20 μm and most preferably 0.5-5 μm. It will be appreciated that large particles (i.e. greater than 50 μm) may not be preferred in applications where a valve or small orifice is employed, since large particles tend to aggregate or separate from a suspension which could potentially clog the device. In especially preferred embodiments the mean geometric particle size (or diameter) of the particulate compositions is less than 20 μm or less than 10 μm. More preferably the mean geometric diameter is less than about 7 μm or 5 μm, and even more preferably less than about 2.5 μm. Other preferred embodiments will comprise preparations wherein the mean geometric diameter of the particulate compositions is between about 1 μm and 5 μm. In especially preferred embodiments the particulate compositions will comprise a powder of dry, hollow, porous microspherical shells of approximately 1 to 10 μm or 1 to 5 μm in diameter, with shell thicknesses of approximately 0.1 μm to approximately 0.5 μm. It is a particular advantage of the present invention that the particulate concentration of the dispersions and structural matrix components can be adjusted to optimize the delivery characteristics of the selected particle size.

Although preferred embodiments of the present invention comprise powders and stabilized dispersions for use in pharmaceutical applications, it will be appreciated that the particulate compositions and disclosed dispersions may be used for a number of non pharmaceutical applications. That is, the present invention provides particulate compositions which have a broad range of applications where a powder is suspended and/or aerosolized. In particular, the present invention is especially effective where an active or bioactive ingredient must be dissolved, suspended or solubilized as fast as possible. By increasing the surface area of the porous microparticles or by incorporation with suitable excipients as described herein, will result in an improvement in dispersibility, and/or suspension stability. In this regard, rapid dispersement applications include, but are not limited to: detergents, dishwasher detergents, food sweeteners, condiments, spices, mineral flotation detergents, thickening agents, foliar fertilizers, phytohormones, insect pheromones, insect repellents, pet repellents, pesticides, fungicides, disinfectants, perfumes, deodorants, etc.

The foregoing description will be more fully understood with reference to the following Examples. Such Examples, are, however, merely representative of preferred methods of practicing the present invention and should not be read as limiting the scope of the invention.

EXAMPLE I

Effect of Added Calcium Ions on the Tm of Spray-Dried Phospholipids

The effect of calcium ions on the gel-to-liquid crystal transition temperature (Tm) of spray-dried phospholipids was investigated. The resulting powders were examined visually for powder flow characteristics, characterized for Tm using a differential scanning calorimeter (DSC).

Dry lung surfactant particles comprising long-chain saturated phosphatidylcholines, PCs (e.g., dipalmitoylphosphatidylcholine, DPPC or distearoylphosphatidylcholine, DSPC) and varying amounts of calcium chloride were manufactured by an emulsion-based spray-drying process. Calcium levels were adjusted as mole ratio equivalents relative to the PC present, with Ca/PC (mol/mol)=0 to 1. Accordingly, 1 g of saturated phosphatidylcholine (Genzyme Corp, Cambridge, Mass.) and 0 to 0.18 g of calcium chloride dihydrate (Fisher Scientific Corp., Pittsburgh, Pa.) were dispersed in approximately 40 mL of hot deionized water (T=60-70° C.) using an Ultra-Turrax T-25 mixer at 8,000-10,000 rpm for 2 to 5 minutes. 18 g of perfluorooctyl ethane, PFOE (F-Tech, Tokyo, Japan) was then added dropwise during mixing at a rate of 2-5 ml/min. After the addition was complete, the emulsion was mixed for an additional period of not less than 4 minutes at 10,000-12,000 rpm. The resulting coarse emulsion was then homogenized under high pressure with an Avestin C-5 homogenizer (Ottawa, Canada) at 8,000-10,000 psi for 4 passes, and at 18,000-20,000 psi for a final pass.

The submicron fluorocarbon-in-water emulsion was then spray-dried with a Buchi B-191 Mini Spray-Drier (Flawil, Switzerland), equipped with a modified 2-fluid atomizer under the following conditions: inlet temperature=85° C.; outlet temperature=58°-61° C.; pump=1.9 ml $min^{-1}$; atomizer pressure=60-65 psig; atomizer flow rate=30-35 cm. The aspiration flow (69-75%) was adjusted to maintain an exhaust bag pressure=20-21 mbar.

The spray-dried phospholipid particles were collected using the standard Buchi cyclone separator. The volume-weighted mean geometric diameter (VMD) of the dry phospholipid particles was confirmed by laser diffraction (Sympatech Helos H1006, Clausthal-Zellerfeld, Germany), and ranged from 2.5 μm to 3.8 μm depending on the formulation.

The resulting dry phospholipid particles were also characterized using a model 2920 DSC (TA Instruments) and by a Karl Fisher moisture analyzer. Approximately 0.5 to 2 mg dry powder was weighed into aluminum sample pans and hermetically sealed. Each sample was analyzed using a modulated DSC mode under the following conditions: equilibration at −20° C., and 2° C./min ramp to 150° C. modulated+/−1° C. every 60 sec. The phospholipid Tm was defined as the peak maxima of the first endothermic transition from each reversing heat flow thermogram. For moisture analysis, approximately 50 mg powder was suspended in 1 mL of anhydrous dimethylforamide (DMF). The suspension was then injected directly into the titration cell and the moisture content was derived. The residual moisture content in the spray-dried DSPC particles is shown in Table Ia, and was found to decrease as a function of Ca/PC mole ratio. Tables Ib and Ic present the Tm values for the various spray-dried PC particles as a function of the Ca/PC ratio. Hydrated DSPC and DPPC liposomes exhibit Tm values of 58 and 42° C., respectively. Dramatic increases in Tm were observed following spray-drying, and with increases in calcium content. The powder formulations devoid of calcium ions were highly cohesive, while the formulations incorporating added calcium were free-flowing powders.

The present example illustrates that the hydration status of powdered phospholipid preparations greatly influences their inherent thermodynamic and physicochemical characteristics, i.e., Tm and flow properties. Increases in phospholipid Tm are believed to directly correlate with increases in thermal stability, which could lead to an enhancement in long-term storage stability. In addition, decreased moisture content may also lead to greater chemical stability.

TABLE Ia

Effect of Added Calcium on the Residual Moisture Content of Spray-Dried DSPC

| Ca/DSPC (mol/mol) | Water Content (%) |
|---|---|
| 0 | 2.9 |
| 0.25 | 1.9 |
| 0.50 | 1.4 |

TABLE Ib

Effect of Added Calcium on the Tm of Spray-dried DSPC

| Ca/DSPC (mol/mol) | Tm (° C.) |
|---|---|
| 0 (hydrated) | 58 |
| 0 | 79 |
| 0.25 | 85 |
| 0.5 | 98 |
| 1.0 | 126 |

TABLE Ic

Effect of Added Calcium on the Tm of Spray-dried DPPC

| Ca/DPPC (mol/mol) | Tm (° C.) |
|---|---|
| 0 (hydrated) | 42 |
| 0 | 63 |
| 0.25 | 69 |
| 0.5 | 89 |

EXAMPLE II

Effect of Added Magnesium Ions on Tm of Spray-Dried Phospholipids

Phospholipid particles stabilized with magnesium ions were prepared by an emulsion-based spray-drying technique. The emulsion feedstock was prepared according to the procedure described below. In the first step, 0.45 g of distearoylphosphatidylcholine, DSPC, and 0.126 g magnesium chloride hexahydrate (Fisher Scientific, Pittsburgh, Pa.) were dispersed in 41 g of hot deionized water (T=60 to 70° C.) using an Ultra-Turrax mixer (model T-25) at 10,000 rpm for 2 min. 17 g of perfluorooctyl ethane was then added drop wise at a rate of approximately 1-2 ml/min during mixing. After the fluorocarbon addition was complete, the emulsion was mixed for an additional period of not less than 4 minutes. The resulting coarse emulsion was then processed through a high pressure homogenizer (Avestin, Ottawa, Canada) at 18,000 psi for 5 passes, to yield a submicron fluorocarbon-in-water emulsion stabilized by a monolayer of DSPC. The emulsion was then spray-dried with a Buchi model B-191 Mini Spray-Drier under the following spray conditions: aspiration=69%, inlet temperature=85° C., outlet temperature=58° C., feed pump=1.9 mL min$^{-1}$, and atomizer flow rate=33 cm.

Differential scanning calorimetric analysis of the dry particles revealed the Tm for the DSPC in the powder was 88° C. as compared with 79° C. for neat DSPC (Table Ib). This foregoing example illustrates the effect ions such as magnesium have upon the thermodynamic properties of dry phospholipid particles.

EXAMPLE III

Preparation of Spray-Dried Lung Surfactant (ExoSurf®) Particles

Dry lung surfactant particles having the same components as ExoSurf® (Glaxo-Wellcome, Research Triangle Park, N.C.) were manufactured using a spray-drying process. To achieve this end, the osmotic NaCl component of Exosurf was replaced in one formulation by $CaCl_2$. Accordingly, 1.55 g of dipalmitoylphosphatidylcholine and 0.144 g of calcium chloride dihydrate or sodium chloride were dispersed in 50 mL of hot deionized water (T=60-70° C.) using an Ultra-Turrax T-25 mixer at 8,000-10,000 rpm for 2 min. 18.5 g of perfluorooctyl ethane was then added dropwise during mixing at a rate of 2-5 ml/min. After the addition was complete, the emulsion was mixed for an additional period of not less than 4 minutes at 10,000-12,000 rpm. The resulting coarse emulsion was then homogenized under high pressure with an Avestin C-5 homogenizer (Ottawa, Canada) at 8,000-10,000 psi for 4 passes, and at 18,000-20,000 psi for a final pass. In a separate flask, 0.12 g of Tyloxapol® was dispersed in 10 g of hot deionized water (T=60-70° C.). The Tyloxapol dispersion was then decanted into a vial that contained 0.174 g of cetyl alcohol. The vial was sealed and the cetyl alcohol was dispersed by placing it in a sonication bath for 15 minutes. The Tyloxapol/cetyl alcohol dispersion was added to the fluorocarbon emulsion and mixed for 5 min. The feed solution was then spray-dried with a Bucchi-191 Mini Spray-Drier, equipped with a modified 2-fluid atomizer under the following conditions: inlet temperature=85° C., outlet temperature=58°-61° C., pump=1.9 ml min$^{-1}$, atomizer pressure=60-65 psig, atomizer flow rate=30-35 cm. The aspiration flow (69-75%) was adjusted to maintain an exhaust bag pressure=20-21 mbar. A free flowing white powder was collected using the standard Buchi cyclone separator.

The spray-dried powders were manually filled into a proprietary blister package and heat-sealed. The filling procedure was performed in a humidity controlled glove box (RH<2%). All blister packages were numbered, then weighed before and after filling to determine the amount of powder loaded. The filled blister packages were stored in a desiccating box operated at <2% RH until use. The powders were then tested for dispersibility from a DPI described in U.S. Pat. No. 5,740,794.

Emitted Dose testing of the formulations was assessed following USP guidelines for inhalation products. The actuated dose was collected using a 30 L min$^{-1}$ flow rate held for 2 seconds onto a type A/E glass filter (Gelman, Ann Arbor, Mich.). The emitted dose was calculated gravimetrically knowing the blister weight, total blister fill weight, and net change in filter weight.

Dry powder containing sodium chloride exhibited poor powder flow, and did not aerosolize well. In contrast, the formulation in which calcium chloride was substituted for the sodium chloride yielded particles with good flow and excellent emitted dose character. The differences in dispersibility between the two formulations is further reflected in the standard deviations of the emitted dose. The foregoing example illustrates the ability of the present invention to alter and modulate the flow and emission properties of dry lipid particles through the inclusion of calcium ions.

TABLE II

Formulation of Highly Dispersible Dry Powder Lung Surfactant Preparations

| Dry Powder Formulation | Ca/DSPC (mol/mol) | Emitted Dose (%) |
|---|---|---|
| "Exosurf" | 0 | 10 ± 33 |
| "Exosurf" + Calcium | 0.5 | 87 ± 3 |

EXAMPLE IV

Thermal Stability of Spray-Dried Phospholipid Particles

In the current example, the thermal stability of the spray-dried phospholipid particles prepared in example I were assessed. Accordingly 50 mg of powder was transferred into 20 mL glass vials and stored in a vacuum oven at 100° C. for 1 hour. The volume-weighted mass median diameters (MMD) for the powders were determined using a SympaTech laser diffraction analyzer (HELOS H1006, Clausthal-Zellerfeld, Germany) equipped with a RODOS type T4.1 vibrating trough. Approximately 1-3 mg of powder was placed in the powder feeder, which was subsequently atomized through a laser beam using 1 bar of air pressure, 60 mbar of vacuum, 70% feed rate and 1.30 mm funnel gap. Data was collected over an interval of 0.4 s, with a 175 μm focal length, triggered at 1% obscuration. Particle size distributions were determined using a Fraünhofer model. The volume-weighted mean aerodynamic diameters (VMAD) for the powders were determined with a model 8050 Aerosizer®LD particle size analysis system (Amherst Process Instruments, Hadley, Mass.) equipped with an Aero-Sampler® chamber. Approximately 0.2 mg of powder was loaded into a specially designed DPI testing apparatus. In this test, the powder was aerosolized by actuating a propellant can containing HFA-134a through the loaded sample chamber. The design of this apparatus is such to mimic actuation from an active DPI device and to offer some insight into powder flowability or its ability to deaggregate. Narrow particle size distributions are preferred and are believed to be an indication of the powder's ability to deaggregate.

Table III depicts the thermal stability and changes in particle size (MMD and VMAD) for the various spray-dried DSPC particles as a function of Ca/DSPC (mol/mol) ratio. The thermal stability of the powders was found to increase with increasing calcium content. Significant structural and particle size changes were observed for the formulation devoid of calcium ions, as evidenced by particle sintering and large increases in MMD and VMAD. The addition of small amounts of calcium ions (Ca/DSPC=0.25) resulting in a significant improvement in thermal stability of the phospholipid particles. More surprising, the spray-dried phospholipid formulation enriched at Ca/DSPC ratio of 0.5 completely tolerated the accelerated storage conditions, as no significant changes had occurred as a result of storage at 100° C. for 1 hour. The above example further illustrates the enhanced thermal stability of spray-dried phospholipid particles afforded by the inclusion of calcium ions.

TABLE III

Aerosol characteristics of Spray-Dried DSPC Powders following Storage at 100° C. for 1 hour

| Ca/DSPC (mol/mol) | Tm (° C.) | Thermal Stability | $MMD_0$ (μm) | $VMAD_0$ (μm) | MMD (μm) | VMAD (μm) |
|---|---|---|---|---|---|---|
| 0 | 79 | Sintering at 5 min. | 3.3 | 2.1 | 5.7 | 4.1 |
| 0.25 | 85 | Sintering at 45 min | 3.4 | 1.8 | 4.5 | 2.1 |
| 0.5 | 98 | No Change | 3.6 | 1.7 | 3.5 | 1.8 |

EXAMPLE V

The Effect of Added Calcium Ions on pMDI Stability

The objective of this study was to examine the effect added calcium had on the physical stability of lipid-based pMDI suspensions to moisture. Budesonide powders were prepared by spray-drying a feed solution comprised of micronized drug particles suspended in the aqueous phase of a fluorocarbon-in-water emulsion. Accordingly, 0.8 g saturated egg phosphatidylcholine (EPC-3, Lipoid K G, Ludwigshafen, Germany) was dispersed in approximately 80 mL hot deionized water (T=80° C.) using an Ultra-Turrax mixer at 8000 rpm for 2 to 5 minutes. 20 g of perflubron (ϕ=0.09) was then added drop wise during mixing. After the addition was complete, the emulsion was mixed for an additional period of not less than 4 minutes. The resulting coarse emulsion was homogenized under high pressure with an Avestin C-5 homogenizer (Ottawa, Canada) at 18,000 psi for 5 passes. The resulting submicron emulsion was then combined with a second aqueous phase containing 1.33 g budesonide suspended in a solution comprising 0.4 g d-lactose monohydrate, and 0-0.134 g calcium chloride dissolved in approximately 30 g of deionized water. The combined solution was then mixed using an Ultra-Turrax mixer at 8000 rpm for 2 minutes to ensure dispersion of the budesonide particles. Hollow porous budesonide particles were prepared by spray-drying the dispersion with a B-191 Mini Spray-Drier (Büchi, Flawil, Switzerland) under the following spray conditions: aspiration=80%, inlet temperature=85° C., outlet temperature=57° C., feed pump=2.3 mL/min, total air flow=22.4 SCFM. Free flowing white powders were collected at the cyclone separator. Scanning electron microscopic (SEM) analysis showed the powders to be spherical and highly porous.

Approximately 40 mg of spray-dried budesonide particles were weighed into 10 ml aluminum cans, and crimp sealed (Pamasol 2005/10, Pfaffikon, Switzerland) with a DF30/50 ACT 50 μl metering valve (Valois of America, Greenwich, Conn.). The canisters were charged with 5 g HFA-134a (DuPont, Wilmington, Del.) propellant by overpressure through the valve stem (Pamasol 8808). To elucidate differences between the budesonide formulations, propellant preparations that were spiked with varying amounts of water (0 to 1100 ppm) were utilized. The amount of the propellant in the can was determined by weighing the can before and after the fill. The final powder concentration in propellant was ~0.8% w/w and formulated to provide a theoretical ex-valve dose of 100 μg budesonide per actuation. Powder dispersion was achieved by placing the canisters in a sonication bath for 15 min. The charged pMDIs were placed in quarantine for a period of 7 days at ambient conditions to allow the valve seals to seat.

For the purpose of this study the aerosol fine particle fraction, FPF (%<5.8 μm) was used to assess changes in suspension physical stability that had occurred as a result of the water activity. The budesonide pMDIs were tested using commonly accepted pharmaceutical procedures. The method utilized was compliant with the United State Pharmacopeia (USP) procedure (Pharmacopeial Previews (1996) 22:3065-3098). After 5 waste shots, 20 doses from the test pMDIs were actuated into an Andersen Impactor. The extraction from all the plates, induction port, and actuator were performed in closed containers with an appropriate amount of methanol:water (1:1, v/v). The filter was installed but not assayed, because the polyacrylic binder interfered with the analysis. Budesonide was quantified by measuring the absorption at 245 nm (Beckman DU640 spectrophotometer) and compared to an external standard curve with the extraction solvent as the blank. The FPF was calculated according to the USP method referenced above.

The effect of added calcium ions on the physical stability of the budesonide pMDIs is depicted in FIG. 1. The physical stability of the budesonide pMDIs was found to increase with increasing calcium concentration. Surprisingly the tolerance of the budesonide pMDI suspension to moisture increased from approximately 400 ppm to nearly 700 ppm by the inclusion of 4% calcium chloride into the formulation.

This example illustrates the enhanced stability of phospholipid-based pMDI particles afforded by the presence of calcium ions. The ability of a pMDI formulation to tolerate increased levels of moisture will lead to an enhancement in their long-term storage stability. The presence of water fuels structural changes, which can lead to formation of liquid bridges between particles and/or recrystallization of components and changes in surface characteristics. The overall effect of moisture ingress for suspension pMDIs leads to particle coarsening and suspension instability, all of which can lead to product failure.

EXAMPLE VI

The Effect of Added Calcium Ions on Particle Morphology

The objective of this study was to examine the effect added calcium has upon the morphological character of spray-dried phospholipid particles. Scanning electron micrographic (SEM) images of the spray-dried distearoylphosphatidylcholine particles prepared in example I were taken. The powders were placed on double sticky carbon graphite that was affixed on labeled aluminum stubs. The samples were then sputter-coated with a 250-300 Å layer of gold/palladium. Samples were examined on a scanning electron microscope operated at an accelerating voltage of 20 Key, and a probe current of 250 pAmps. Photomicrographs were digitally captured at a 20,000× magnification.

The effect of calcium ion concentration on the morphology of spray-dried DSPC particles is illustrated in FIG. 1I. Formulations containing calcium ions had a highly porous sponge-like inflated morphology, whereas the neat DSPC particles appeared melted and collapsed. The hollow porous morphology is characterized by powders that flow and aerosolize well, whereas the collapsed morphology results in powders with poor flowability and dispersibility. No significant difference in morphology was observed as a result of calcium ion concentration, although the Ca/DSPC=0.25 formulation exhibited some degree of melted character as well. The decreased sensitivity of the powders with higher calcium content to melting and particle fusion is likely the result of the increased Tm values that allow for the powders to experience a higher drying temperature while maintaining the lipids in the gel state. The significant increases in Tm observed (Example I) lead to greater flexibility in spray-drying manufacture of these particles, and a significantly greater likelihood of achieving desired particle morphologies which are dependent on drying rates.

EXAMPLE VII

Preparation of Spray-Dried Budesonide Particles

Hollow porous budesonide particles were prepared by a two-step process. In the first step, 54 mg of budesonide (Vinchem, Chatham, N.J.), and 0.775 g of DSPC were dissolved in 2 ml of chloroform:methanol (2:1). The chloroform:methanol was then evaporated to obtain a thin film of the phospholipid/steroid mixture. The phospholipid/steroid mixture was then dispersed in 30.5 g of hot deionized water (T=60 to 70° C.) using an Ultra-Turrax mixer (model T-25) at 8000 rpm for 2 to 5 minutes. 12.8 g of perfluorooctyl ethane was then added dropwise during mixing. After the addition was complete, the emulsion was mixed for an additional period of not less than 4 minutes. The coarse emulsion was then passed through a high pressure homogenizer (Avestin, Ottawa, Canada) at 18,000 psi for 5 passes. The resulting submicron fluorocarbon-in-water with steroid solubilized in the lipid monolayer surrounding the droplets was utilized as the feedstock in for the second step, i.e. spray-drying on a B-191 Mini Spray-Drier (Büchi, Flawil, Switzerland). Calcium chloride (0 or 0.65 mg) was added in 2.5 g of water to the fluorocarbon-in-water emulsion immediately prior to spray drying. The following spray conditions were employed: aspiration=100%, inlet temperature=85° C., outlet temperature=60° C., feed pump=1.9 mL min$^{-1}$, atomizer pressure=60-65 prig, atomizer flow rate=30-35 cm. The aspiration flow (69-75%) was adjusted to maintain an exhaust bag pressure of 30-31 mbar. Free flowing white powders were collected using a standard cyclone separator.

The resulting dry budesonide particles were characterized using DSC. Each sample was analyzed in a modulated DSC mode under the following conditions: equilibration at −20° C., and 2° C./min ramp to 150° C. modulated+/−1° C. every 60 sec. The phospholipid Tm was defined as the peak maxima of the first endothermic transition from each reversing heat flow thermogram. The phospholipid Tm for DSPC particles without added calcium is 79° C. The addition of calcium ions in the budesonide formulation increased the Tm to 98° C. In addition, the powder formulations devoid of calcium had a cohesive flow character as compared to the calcium-enriched formulation.

The aerosol characteristics of the calcium containing formulation was examined in several passive dry powder inhaler devices (Eclipse®, Turbospin®, Cipla Rotahaler®, Glaxo Rotahaler®®, and Hovione FlowCaps®). The emitted dose was determined gravimetrically at comfortable inhalation flow rate (peak flow rate=20-62 L/min depending on the resistance of the device), and at a forced inhalation flow rate (peak flow rate 37-90 L/min). Under comfortable inhalation flow conditions the range of emitted doses were between 89 and 96% with a mean emitted dose of 94%. Under forced inhalation flow, the emitted dose varied between 94 and 103%, with a mean emitted dose of 99%. The fact that multiple devices with high and low resistance are able to effectively disperse the powders more or less independent of inspiratory flow rate speaks volumes to the dispersibility of the calcium containing budesonide powder tested.

The above example further illustrates the ability of the present powder engineering technology to effectively modulate the Tm through formulation changes. Increased (Tm's) are desired as they often indicate increased physical stability and improved powder dispersibility.

EXAMPLE VIII

Rapid Spreading of Spray-Dried DSPC Particles on an Air-Water Interface

The rapid spreading characteristics of the disclosed spray-dried phospholipid-based particles at the air/water interface are illustrated in Fig. III. Surface tension measurements were made on a Kruss K12 tensiometer at 25° C. using the Wilhemey plate technique. To measure surface tension, 20 mL of DI water or DSPC liposome dispersion was placed in the thermostatic beaker. The platinum plate was tared in the air and then dipped into the liquid and moved into the interface, after which measurements were taken. For spray-dried DSPC particle analysis, measurements for DI water were made and confirmed to be 72±1 mN/m. The glassware and plate were re-cleaned if the surface tension was not within expectation. Approximately 0.5 mg of dry DSPC crystal was sprinkled carefully onto the surface while the plate was dipped into the DI water. Measurements were started immediately after the powder was added. Care was taken to ensure dry powder did not adsorb to the plate. Measurements were ceased if any powder had contacted the plate surface. The equilibrium surface tension of distearoyl-phosphatidylcholine (DSPC) is ca. 22 mN/m. Aqueous based DSPC liposomes adsorbed very slowly at the air/water interface as evidenced by the fact that after 240 sec., the surface tension has not been significantly reduced. The slow adsorption for liposomes is due to the slow molecular diffusion of DSPC through the water phase, resulting from its extremely low solubility in water. Surprisingly, the adsorption of DSPC in the form of spray-dried DSPC particles is very fast, reducing the surface tension to equilibrium values within a few seconds. Moreover the inclusion of calcium ions had no effect on the spreading of surfactant properties of the DSPC particles. This rapid spreading and reduction of surface tension is indicative of what would likely occur upon contacting the spray-dried phospholipid particles with a wetted pulmonary membrane. Specifically, the present example provides a model for the effective delivery of synthetic lung surfactants and drugs to the lung.

EXAMPLE IX

Preparation of Nicotine Bitartrate Particles for pMDIs by Spray-Drying

Hollow porous nicotine bitartrate particles were prepared by a spray-drying technique with a B-191 Mini Spray-Drier (Büchi, Flawil, Switzerland) under the following spray conditions: aspiration: 80%, inlet temperature: 85° C.; outlet temperature: 56° C.; feed pump: 2.3 mL/min; air flow: 28 SCFM. The feed solution was prepared by mixing two solutions A and B immediately prior to spray drying.

Solution A: 5.2 g of hot water (T=50-60° C.) was used to dissolve 0.60 g of nicotine bitartrate (Sigma Chemicals, St.

Louis Mo.), 0.127 g d-l lactose (Sigma Chemicals, St. Louis Mo.), and 90 mg calcium chloride dihydrate (Fisher Scientific, Fair Lawn, N.J.).

Solution B: A fluorocarbon-in-water emulsion stabilized by phospholipid was prepared in the following manner. The phospholipid, 0.69 g SPC-3 (Lipoid K G, Ludwigshafen, Germany) was dispersed in 29 g of hot deionized water (T=60 to 70° C.) using an Ultra-Turrax mixer (model T-25) at 8000 rpm for 2 minutes (T=60-70° C.). 30.2 g of perfluorooctyl ethane (F-Tech, Japan) was added dropwise during mixing. After the fluorocarbon was added, the emulsion was mixed for a period of not less than 5 minutes at 10000 rpm. The resulting coarse emulsion was then passed through a high pressure homogenizer (Avestin, Ottawa, Canada) at 18,000 psi for 5 passes. Solutions A and B were combined and fed into the spray-dryer under the conditions described above. A free flowing white powder was collected at the cyclone separator. The geometric diameter of the nicotine bitartrate particles was confirmed by laser diffraction (Sympatech Helos H1006, Clausthal-Zellerfeld, Germany), where a volume weighted mean diameter (VMD) of 2.60 μm was found. Scanning electron microscopy (SEM) analysis showed the powders to be spherical and porous. Differential scanning calorimetry analysis of the dry particles (TA Instruments) revealed the Tm for the nicotine bitartrate in the powder to be 62° C., which is similar to what is observed for spray-dried neat material.

EXAMPLE X

Preparation of Phospholipid-Based Particles Containing Nicotine Bitartrate by Spray-Drying Hollow porous nicotine bitartrate particles were prepared by a spray-drying technique with a B-191 Mini Spray-Drier (Büchi, Flawil, Switzerland) under the following spray conditions: aspiration: 80%, inlet temperature: 85° C.; outlet temperature: 57° C.; feed pump: 2.3 mL/min; total air flow: 22.4 SCFM.

A fluorocarbon-in-water emulsion stabilized by phospholipid was first prepared. The phospholipid, 0.45 g SPC-3 (Lipoid K G, Ludwigshafen, Germany), was homogenized in 30 g of hot deionized water (T=60 to 70° C.) using an Ultra-Turrax mixer (model T-25) at 8000 rpm for 2 (T=60-70° C.). 15 g of perfluorooctyl ethane (F-Tech, Japan) was added dropwise at a rate of approximately 1-2 ml/min during mixing. After the fluorocarbon was added, the emulsion was mixed for a period of not less than 4 minutes. The resulting coarse emulsion was then processed through a high pressure homogenizer (Avestin, Ottawa, Canada) at 18,000 psi for 5 passes.

The emulsion was decanted into a beaker containing 8 mg sodium phosphate monobasic (Spectrum Chemicals, Gardena, Calif.) and 90 mg calcium chloride dihydrate (Fisher Scientific, Fair Lawn, N.J.). The emulsion was allowed to stir for approximately 5 min. The emulsion was then decanted into a beaker containing 0.225 g nicotine bitartrate (Sigma Chemicals, St. Louis Mo.) and was stirred for 5 minutes. The feed solution was fed into the spray-dryer under the conditions described above. A free flowing white powder was collected at the cyclone separator. The nicotine bitartrate particles had a volume-weighted mean aerodynamic diameter of 1.47 μm as determined by a time-of-flight analytical method (Aerosizer, Amherst Process Instruments, Amherst, Mass.). The geometric diameter of the nicotine bitartrate particles was determined by laser diffraction (Sympatech Helos H1006, Clausthal-Zellerfeld, Germany), where a volume weighted mean diameter (VMD) of 2.95 μm was found. Scanning electron microscopy (SEM) analysis showed the powders to be spherical and highly porous. Differential scanning calorimetry analysis of the dry particles (TA Instruments) revealed the Tm for the nicotine bitartrate in the powder was approximately 85° C.

This foregoing example illustrates the ability of the present powder engineering technology to effectively modulate the Tm through formulation changes

EXAMPLE XI

The preparation of lung surfactant powders with and without the use of blowing agents was investigated. The resultant powders were characterized as to aerosol properties.

Preparation of Powders

The annex solutions were prepared by mixing calcium or sodium chloride, cetyl alcohol, tyloxapol (Sigma), and Infasurf (ONY Inc.) as described in Table IV in a 20 ml glass vial to which was added an amount of hot deionized water (70° C.) (approximately 0.54 g of sodium chloride were used instead of calcium chloride in lots 1843-HS-03 and 04). The mixture was vortexed until all solids were fully dissolved. One lot, 1843-HS-04 used 200 ml ethanol as a solvent.

The emulsions were prepared by adding DPPC into a beaker to which was added an amount of 70° C. deionized water. The mixture was mixed in a mixer on low speed for approximately 2-3 minutes. When a blowing agent was used, PFOE was weighed out into a small flask and added dropwise into the DPPC/water mixture. The PFOE was added slowly over the course of 1-2 minutes and the mixture was then allowed to continue mixing for an additional 1-2 minutes. Emulsion details are listed in Table IV.

When a blowing agent was used, the DPPC/water/PFOE mixture was then immediately removed from the mixer and run through a homogenizer four times at 10,000-13,000 psi. The sample was then run through a homogenizer a fifth time at 13,000-17,000 psi.

The annex solution was then added to the DPPC/water or DPPC/water/PFOE emulsion with continued stirring on a hot plate set to the lowest temperature. The mixtures were kept at approximately 50° C. during spray drying, which was done at the conditions listed in Table V.

TABLE IV

Annex/Emulsion Formulation and Spray Drying Conditions

| | | | | Emulsion | | | Annex Solution | | | | | |
|---|---|---|---|---|---|---|---|---|---|---|---|---|
| Lot # | Atom. Press. (psi) | Out Temp, C. | Flow rate (ml/min) | DPPC (g) | PFOE (g) | Hot* DI Water (g) | Calcium Chloride (g) | Tyloxapol (g) | Cetyl Alcohol (g) | Hot* DI Water (g) | Infasurf (g) | Water (g), From Infasurf |
| 1843-HS-01 | 60 | 60 | 2.5 | 1.560 | 18.5 | 40.42 | 0.144 | 0.120 | 0.174 | 20 | | |
| 1843-HS-03 | 60 | 58 | 2.5 | 1.234 | 18.5 | 50 | | 0.092 | 0.138 | 10 | | |

TABLE IV-continued Annex/Emulsion Formulation and Spray Drying Conditions

| Lot # | Atom. Press. (psi) | Out Temp, C. | Flow rate (ml/min) | Emulsion DPPC (g) | Emulsion PFOE (g) | Emulsion Hot* DI Water (g) | Annex Solution Calcium Chloride (g) | Annex Solution Tyloxapol (g) | Annex Solution Cetyl Alcohol (g) | Annex Solution Hot* DI Water (g) | Annex Solution Infasurf (g) | Annex Solution Water (g), From Infasurf |
|---|---|---|---|---|---|---|---|---|---|---|---|---|
| 1843-HS-04 | 70 | 43/44 | 5.0 | 1.236 | | 50 (cold) | | 0.093 | 0.138 | | | |
| 1843-HS-26 | 70 | 60 | 5.0 | 1.554 | | 180 | 0.145 | 0.120 | 0.176 | 20 | | |
| 1843-HS-35 | 56 | 59 | 2.5 | 0.937 | 14.0 | 35 | 0.043 | | | | 0.420 | 12 |
| 1843-HS-38 | 60 | 55 | 2.5 | 0.227 | 8.0 | 10 | 0.044 | | | | 0.630 | 18 |
| 1843-HS-50 | 56 | 57 | 2.5 | 1.555 | | 180 | 0.145 | 0.128 | 0.177 | 20 | | |
| 1843-HS-51 | | 50 | 1.5 | 1.165 | | 130 | 0.109 | 0.092 | 0.132 | 20 | | |
| 1843-HS-55 | 50 | 50 | 1.5 | 0.937 | | 140 | 0.043 | | | | 0.420 | 12 |
| 1843-HS-64 | 50 | 50 | 1.5 | 0.230 | | 88.2 | 0.044 | | | | 0.630 | 18 |
| 1843-HS-67 | 50 | 43 | 1.5 | 0.091 | | 78 | 0.091 | | | | 0.420 | 12 |
| 1843-HS-69 | 70 | 60 | 5.0 | 0.092 | | 48 | 0.091 | | | | 0.420 | 12 |
| 1843-HS-70 | 50 | 35 | 1.5 | 0.090 | | 48 | 0.090 | | | | 0.420 | 12 |
| 1843-HS-77 | 60 | 43 | 2.5 | 1.540 | 18.2 | 50 | 0.146 | | | 10 | | |
| 1843-HS-78 | 50 | 35 | 1.5 | 0.150 | | 48 | 0.030 | | | | 0.420 | 12 |
| 1876-HS-88 | 60 | 44 | 2.5 | 0.775 | 9.2 | 25 | 0.080 | 0.065 | 0.087 | 5 | | |
| 1876-HS-90 | 70 | 60 | 5.0 | 0.775 | 9.3 | 25 | 0.088 | 0.064 | 0.088 | 5 | | |
| 1876-HS-92 | 60 | 60 | 2.5 | 0.776 | 9.3 | 25 | 0.072 | 0.060 | 0.087 | 5 | | |
| 1959-HS-36 | 60 | 59 | 2.5 | 0.227 | 8.0 | 10 | 0.043 | | | | 0.630 | 18 |
| 1959-HS-39 | 70 | 57 | 5 | 0.200 | 8.0 | 10 | 0.075 | | | | 0.630 | 18 |
| 1959-HS-50 | 60 | 60 | 2.5 | 0.200 | 8.0 | 10 | 0.074 | | | | 0.630 | 18 |
| 1959-HS-51 | 70 | 57 | 5 | 0.212 | 9.0 | 60.35 | 0.074 | | | | 0.630 | 18 |

TABLE V

Aerosol Characteristics

| Lot # | Yield | Lipid: CaCl | Fill Weight | % Moisture | % ED | SD | % RSD | % Left | % Collected | MMAD | % <3.3 mm | aero-sizer | MMD (SYMPA) |
|---|---|---|---|---|---|---|---|---|---|---|---|---|---|
| 1843-HS-01 | 43.0 | 2 | 2.2 | 4.453 | 86.7 | 2.15 | 2.5 | 2.00 | 90.81 | 3.43 | 46 | 1.287 | 2.83 |
| 1843-H3-03 | 36.0 | No CaCl | 2.2 | 2.205 | 10 | 3.28 | 32.7 | 17.98 | 16.80 | 5.5 | 14 | | |
| 1843-HS-04 | 19.0 | No CaCl | 5.0 | 1.235 | 7.3 | 2.18 | 30.0 | 30.54 | 10.89 | — | — | | |
| 1843-HS-26 | 35.4 | 2 | 5.0 | 5.563 | 66.26 | 7.15 | 10.8 | 4.05 | 69.16 | 3.65 | 44 | | |
| 1843-HS-26 | 35.4 | 2 | 2.2 | — | 82.44 | 4.11 | 5.0 | 11.07 | 92.70 | 2.90 | 57 | | — |
| 1843-HS-35 | 36.5 | 5.78 | 2.2 | 3.722, 2.89KF | 81.63 | 3.04 | 3.7 | 3.9 | 84.98 | 4.25 | 29 | 2.683/ 2.980 | 3.84/ 3.89 |
| 1843-HS-38 | 29.0 | 3.57 | 2.2 | 3.04 | 83.35 | 2.93 | 3.5 | 3.25 | 86.16 | 4.14 | 33 | 2.799 | 3.93 |
| 1843-HS-50 | 27.3 | 2 | not filled | — | — | — | — | — | — | — | — | — | — |
| 1843-HS-51 | 40.7 | 2 | 2.2 | 3.344 | 85.77 | 2.83 | 3.3 | 9.10 | 94.37 | 3.22 | 51 | | |
| 1843-HS-51 | 40.7 | 2 | 5.0 | — | 76.09 | 5.33 | 7.0 | 4.19 | 79.41 | 3.85 | 42 | | — |
| 1843-HS-55 | 58.0 | 5.78 | 2.2 | 2.058 | 67.87 | 10.67 | 15.7 | 5.66 | 71.85 | 3.45 | 46 | | |
| 1843-HS-64 | 11.5 | 1.79 | not filled | — | — | — | — | — | — | — | — | — | — |
| 1843-HS-67 | 27.8 | 1 | not filled | — | — | — | — | — | — | — | — | — | — |
| 1843-HS-69 | 11.6 | 1 | not filled | — | — | — | — | — | — | — | — | — | — |
| 1843-HS-70 | 40.4 | 1 | 2.2 | 3.254 | 54.55 | 5.05 | 9.3 | 8.29 | 59.54 | 3.51 | 45 | | |
| 1843-HS-78 | 52.0 | 3.40 | 2.2 | 2.237, 2.89KF | 69.87 | 11.72 | 16.8 | 2.78 | 71.77 | 3.74 | 39 | 3.07 | 3.98 |
| 1876-HS-88 | 51.0 | 3.57 | 2.2 | 5.050 | 83.71 | 8.69 | 10.4 | 7.47 | 90.45 | 3.57 | 45 | | 2.76/2.80/ 2.74 |
| 1876-HS-90 | 52.8 | 3.57 | 2.2 | 4.871 | 91.88 | 4.15 | 4.5 | 6.87 | 98.67 | 2.94 | 56 | | 2.16/ 2.16 |
| 1876-HS-92 | 47.3 | 3.57 | 2.2 | 5.066 | 93.31 | 2.58 | 2.8 | 5.13 | 98.40 | 3.28 | 50 | | 2.32/ 2.26 |
| 1959-HS-36 | 39.4 | 3.57 | 2.2 | 2.828 | 69.36 | 10.77 | 15.5 | 2.69 | 71.29 | 3.73 | 41 | — | 2.94/ 2.86 |
| 1959-HS-39 | 72.8 | 2 | 2.2 | | 83.52 | 3.06 | 3.7 | 3.33 | 86.46 | 3.63 | 43 | — | 2.68/ 2.67 |
| 1959-HS-50 | 23.3 | 2 | not filled | 3.150 | — | — | — | — | — | — | — | — | — |
| 1959-HS-51 | 72.7 | 2 | 2.2 | 4.954 | 85.19 | 1.66 | 2 | 2.11 | 83.5 | 3.71 | 43 | — | 2.36/ 2.44 |

EXAMPLE XII

Leuprolide Acetate Particles

A single feed solution is prepared under defined conditions. The feed solution is comprised of leuprolide acetate in the aqueous phase of a fluorocarbon-in-water emulsion. The emulsion composition is listed in Table VI below. Accordingly, DSPC and calcium chloride dihydrate are dispersed in approximately 400 mL SWFI (T=60-70 C) using an Ultra-Turrax T-50 mixer at 8000 rpm for 2 to 5 minutes. The perflubron is then added drop wise during mixing. After the addition is complete, the emulsion is mixed for an additional period of not less than 5 minutes at 10,000 rpm. The resulting coarse emulsion is then homogenized under high pressure with an Avestin C-5 homogenizer (Ottawa, Canada) at 19,000 psi for 5 discrete passes. The emulsion is transferred to the Potent Molecule Laboratory for Leuprolide Acetate addition and spray drying.

TABLE VI

Leuprolide Acetate Emulsion Composition

| Emulsion Components | Amount (grams) | % solids |
|---|---|---|
| DSPC | 7.33 | 73% |
| Calcium Chloride | 0.67 | 7% |
| Perflubron | 200 | NA |
| SWFI | 400 | NA |
| Leuprolide Acetate | 2.00 | 20% |

Aerosol Data:

Deposition analysis is performed using a multi-stage liquid impinger (MSLI). The apparatus consists of four concurrent stages and a terminal filter, each containing an aliquot of appropriate solvent for Leuprolide Acetate analysis. Deposition and emission data is reported in Table VII below.

TABLE VII

Leuprolide Acetate Aerosol Data

| Lot# | XB2316 |
|---|---|
| Device | Turbospin |
| Flow Rate | 60 Lpm |
| Emitted Dose | 96% |
| n = | 20 |
| MMAD | 2.40 |
| S4-Filter | 70% |
| n = | 4 |

EXAMPLE XIII

PTH Feed Solution Preparation

A single feed solution is prepared under defined conditions. The feed solution is comprised of parathyroid hormone in the aqueous phase of a fluorocarbon-in-water emulsion. The emulsion composition is listed in Table VIII below. Accordingly, DSPC and calcium chloride dihydrate are dispersed in approximately 40 mL SWFI (T=60-70 C) using an Ultra-Turrax T-50 mixer at 8000 rpm for 2 to 5 minutes. The perfluorooctylethane is then added drop wise during mixing. After the addition is complete, the emulsion is mixed for an additional period of not less than 5 minutes at 10,000 rpm. The resulting coarse emulsion is then homogenized under high pressure with an Avestin C-5 homogenizer (Ottawa, Canada) at 19,000 psi for 5 discrete passes. The active drug is added to the emulsion and subsequently spray dried after mixing for a period of not less than 10 minutes.

TABLE VIII

Parathyroid Hormone Emulsion Composition

| Emulsion Components | Amount (grams) | % solids |
|---|---|---|
| DSPC | 0.825 | 82.5% |
| Calcium Chloride | 0.075 | 7.5% |
| Perfluorooctylethane(PFOE) | 28 | NA |
| SWFI | 40 | NA |
| Parathyroid Hormone | 0.100 | 10% |

Aerosol Data:

Deposition analysis is performed using an Anderson Cascade Impactor. The apparatus consists of seven concurrent stages and a terminal filter. Aerosol deposition is measured gravimetrically and is reported in Table IX below.

TABLE IX

Parathyroid Hormone Aerosol Data

| Lot# | 2193-1 |
|---|---|
| Device | Turbospin |
| Flow Rate | 30 Lpm |
| MMAD | 2.67 |
| S4-Filter | 59% |
| n = | 2 |

EXAMPLE XIV

Preparation of Metered Dose Inhalers Containing Nicotine Bitartrate Particles 50 mg of nicotine bitartrate particles prepared in Examples IX, and X were weighed into 10 ml aluminum cans, crimp sealed a DF30/50 RCU-20cs 50 µl valve (Valois of America, Greenwich, Conn.) and charged with HFA-134a (DuPont, Wilmington, Del.) propellant by overpressure through the stem. A Pamasol (Pfaffikon, Switzerland) model 2005 small scale production plant complete with a model 2008 propellant pump was used for this purpose. The amount of the propellant in the can was determined by weighing the can before and after the fill. The final powder concentration in propellant was 0.5% w/w and formulated to provide an approximate emitted dose of 110 µg nicotine bitartrate.

EXAMPLE XV

Andersen Impactor Test for Assessing Nicotine Bitartrate pMDI Performance

The MDIs were tested using commonly accepted pharmaceutical procedures. The method utilized was compliant with the United State Pharmacopeia (USP) procedure (Pharmacopeial Previews (1996) 22:3065-3098) incorporated herein by reference. After 5 waste shots, 20 doses from the test pMDIs were actuated into an Andersen Impactor.

Extraction Procedure.

The extraction from all the plates, induction port, and actuator were performed in closed containers with an appropriate amount of methanol:water (1:1, v/v). The filter was installed but not assayed, because the polyacrylic binder interfered with the analysis. The mass balance and particle size distribution trends indicated that the deposition on the filter was negligibly small.

Quantitation Procedure.

Nicotine bitartrate was quantitated by measuring the absorption at 258 nm (Beckman DU640 spectrophotometer) and compared to an external standard curve with the extraction solvent as the blank.

Calculation Procedure.

For each MDI, the mass of the drug in the stem (component-3), actuator (-2), induction port (-1) and plates (0-7) were quantified as described above. The Fine Particle Dose and Fine Particle Fraction was calculated according to the USP method referenced above. Throat deposition was defined as the mass of drug found in the induction port and on plates 0 and 1. The mean mass aerodynamic diameters (MMAD) and geometric standard diameters (GSD) were evaluated by fitting the experimental cumulative function with log-normal distribution by using two-parameter fitting routine. The results of these experiments are presented in subsequent examples.

EXAMPLE XVI

Andersen Cascade Impactor Results for Nicotine Bitartrate pMDI Formulations

The results of the cascade impactor tests for the nicotine bitartrate pMDIs prepared according to Example XIV are shown below in Table X.

TABLE X

Nicotine Bitartrate pMDIs

| | MMAD (GSD) μm | Fine particle fraction, % | Fine Particle Dose, μg |
|---|---|---|---|
| Nicotine/SPC-3/CaCl$_2$/Lactose | 3.6 (2.0) | 70 | 74 |
| Nicotine/SPC-3/CaCl$_2$/NaPhosphate | 3.0 (1.9) | 73 | 80 |

Both pMDI preparations were observed by visual inspection to have excellent suspension stability, where little or no creaming or sedimentation occurred over 1 hour. The lactose containing formulations had a slightly larger MMAD and lower FPF and FPD as compared with the sodium phosphate formulation. The reduction in aerosol performance for the lactose formulation could be due to increased water content as evidenced in the reduced Tm.

The invention has now been described in detail for purposes of clarity and understanding. However, it will be appreciated that certain changes and modifications may be practiced within the scope of the appended claims.

The invention claimed is:

1. A particulate composition for delivery to the pulmonary system, the particulate composition comprising:
dry particles, wherein each particle comprises an active agent, a phospholipid, and a polyvalent cation, wherein the particles have a mass median diameter of 0.5 to 5 microns, and wherein the particulate composition is characterized by being deliverable at an emitted dose in a dry powder inhaler of at least 54.55%.

2. A composition according to claim 1 wherein the particles comprise a mass median aerodynamic diameter of less than 10 microns.

3. A composition according to claim 2 wherein the aerodynamic diameter is 0.5 to 5 microns.

4. A composition according to claim 1 wherein the particles are spray dried particles.

5. A composition according to claim 1 wherein the polyvalent cation is present at a molar ratio of cation:phospholipid of 0.25 to 1.0.

6. A composition according to claim 1 wherein the polyvalent cation is present at a molar ratio of cation:phospholipid of about 0.5.

7. A composition according to claim 1 wherein the polyvalent cation is present in the form of calcium chloride.

8. A composition according to claim 1 wherein the active agent is selected from the group consisting of an antibiotic, antibody, antiviral agent, anti-epileptic, analgesic, anti-inflammatory agent and bronchodilator.

9. A composition according to claim 1 wherein the active agent comprises one or more of insulin, calcitonin, erythropoietin (EPO), Factor VIII, Factor IX, ceredase, cerezyme, cyclosporine, granulocyte colony stimulating factor (GCSF), alpha-1 proteinase inhibitor, elcatonin, granulocyte macrophage colony stimulating factor (GMCSF), growth hormone, human growth hormone (hGH), growth hormone releasing hormone (GHRH), heparin, low molecular weight heparin (LMWH), interferon alpha, interferon beta, interferon gamma, interleukin-2, luteinizing hormone releasing hormone (LHRH), leuprolide, somatostatin, somatostatin analogs including octreotide, vasopressin analog, follicle stimulating hormone (FSH), immunoglobulin, insulin-like growth factor, insulintropin, interleukin-1 receptor antagonist, interleukin-3, interleukin-4, interleukin-6, macrophage colony stimulating factor (M-CSF), nerve growth factor, parathyroid hormone (PTH), thymosin alpha 1, IIb/IIIa inhibitor, alpha-1 antitrypsin, respiratory syncytial virus antibody, cystic fibrosis transmembrane regulator (CFTR) gene, deoxyribonuclease (Dnase), bactericidal/permeability increasing protein (BPI), anti-CMV antibody, interleukin-1 receptor, 13-cis retinoic acid, nicotine, nicotine bitartrate, gentamicin, ciprofloxacin, amphotericin, amikacin, tobramycin, pentamidine isethionate, albuterol sulfate, metaproterenol sulfate, beclomethasone dipropionate, triamcinolone acetamide, budesonide acetonide, ipratropium bromide, flunisolide, fluticasone, fluticasone propionate, salmeterol xinofoate, formeterol fumarate, cromolyn sodium, ergotamine tartrate and analogues, agonists and antagonists thereof.

10. A composition according to claim 1 wherein the active agent comprises tobramycin.

11. A composition according to claim 1 wherein the active agent comprises ciproflaxcin.

12. A composition according to claim 1 wherein the active agent comprises amphotericin.

13. A composition according to claim 1 wherein a particulate composition bulk density is less than 0.05 g/cm$^3$.

14. A composition according to claim 1 wherein the phospholipid is a zwitterionic phospholipid.

15. A composition according to claim 1 wherein the phospholipid comprises one or more of dipalmitoylphosphatidylcholine, disteroylphosphatidylcholine, diarachidoylphosphatidylcholine, dibehenoylphosphatidylcholine, diphosphatidyl glycerol, short-chain phosphatidylcholines, long-chain saturated phosphatidylethanolamines, long-chain saturated phosphatidylserines, long-chain saturated phosphatidylglycerols, and long-chain saturated phosphatidylinositols.

16. A composition according to claim 1 wherein the particles further comprise an additional excipient.

17. A composition according to claim 1 wherein the particles further comprise an additional active agent.

18. A unit dose package comprising a reservoir containing a unit dose of a particulate composition according to claim 1.

19. A unit dose package according to claim 18 wherein the unit dose package is insertable into a dry powder inhaler.

* * * * *